(12) United States Patent
Wythes et al.

(10) Patent No.: US 10,968,242 B2
(45) Date of Patent: Apr. 6, 2021

(54) CYCLOPENTANE-BASED MODULATORS OF STING (STIMULATOR OF INTERFERON GENES)

(71) Applicant: PFIZER INC., New York, NY (US)

(72) Inventors: Martin James Wythes, Solana Beach, CA (US); Indrawan James McAlpine, San Diego, CA (US); Ryan Patman, San Diego, CA (US); Eugene Yuanjin Rui, San Diego, CA (US); Andreas Maderna, Walnut Creek, CA (US); Mehran Jalaie, San Diego, CA (US); Ketan S. Gajiwala, San Diego, CA (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 16/702,738

(22) Filed: Dec. 4, 2019

(65) Prior Publication Data

US 2020/0102334 A1 Apr. 2, 2020

Related U.S. Application Data

(63) Continuation of application No. 16/297,910, filed on Mar. 11, 2019, now Pat. No. 10,538,542.

(60) Provisional application No. 62/643,467, filed on Mar. 15, 2018, provisional application No. 62/666,204, filed on May 3, 2018, provisional application No. 62/742,532, filed on Oct. 8, 2018, provisional application No. 62/809,990, filed on Feb. 25, 2019.

(51) Int. Cl.

| A61K 31/7084 | (2006.01) |
|---|---|
| A61K 47/68 | (2017.01) |
| A61P 35/00 | (2006.01) |
| C07H 21/02 | (2006.01) |
| C07H 21/04 | (2006.01) |
| C07F 9/6574 | (2006.01) |
| C07H 19/213 | (2006.01) |

(52) U.S. Cl.
CPC ...... C07F 9/65744 (2013.01); A61K 47/6801 (2017.08); A61P 35/00 (2018.01); C07H 19/213 (2013.01)

(58) Field of Classification Search
CPC ..... A61K 31/7084; A61K 47/68; A61P 35/00; C07H 21/02; C07H 21/04; C07F 9/6574
See application file for complete search history.

(56) References Cited

FOREIGN PATENT DOCUMENTS

| WO | 91/11172 A1 | 8/1991 |
| WO | 94/02518 A1 | 2/1994 |
| WO | 98/55148 A1 | 12/1998 |
| WO | 2015/185565 A1 | 12/2015 |
| WO | 2016/120305 A1 | 8/2016 |

OTHER PUBLICATIONS

Bala et al., "PLGA Nanoparticles in Drug Delivery: The State of the Art", Critical Reviews in Therapeutic Carrier Systems, 21(5), 387-422 (2004).
Barber, "STING: infection, inflammation and cancer", Nature Reviews Immunology, 15, 760-770, 2015.
Cheng et al., "Relationship Between the Inhibition Constant (K1) and the Concentration of Inhibitor Which Causes 50 Per Cent Inhibition (I50) of an Enzymatic Reaction*", Biochemical Pharmacology, 22, 3099-3108, 1973.
Deardorff et al., "A Highly Enantioselective Hydrolysis of CIS-3,5-Diacetoxycyclopent-1-ENE. An Enzymatic Preparation of 3(R)-Acetoxy-5(S)-Hydroxycyclopent-1-ENE", Tetrahedron Letters, 27(11), 12-55-1256, 1986.
Gaffney et al., "One-Flask Synthesis of c-di-GMP and the [Rp,Rp] and [Rp, Sp] Thiophosphate Analogues", Organic Letters, 12(14), 3269-3271, 2010.
Haleblian, "Characterization of Habits and Crystalline Modification of Solids and Their Pharmaceutical Application", Journal of Pharmaceutical Sciences, 64(8), 1269-1288, 1975.
Hughes, "Nanostructure-mediated drug delivery", Nanomedicine: Nanotechnology, Biology & Medicine, 1, 22-30, 2005.
Zhao et al., "Thiophosphate Analogs of C-di-GMP: Impact on Polymorphism", Nucleosides, Nucleotides and Nucleic Acids, 28, 352-378, 2009.
McCune et al., "Active Specific Immunotherapy With Tumor Cells and Corynebacterium Parvum. A Phase I Study". Cancer, 43:1619-1623, 1979.
Trost et al., "A Short Enantioselective Synthesis of Carbanucleosides", Agnew. Chem. Int. Ed. Engel., 35(13/14), 1569-1572, 1996.

(Continued)

*Primary Examiner* — Brenda L Coleman
(74) *Attorney, Agent, or Firm* — Victoria C. Summers

(57) ABSTRACT

Compounds of the general formula (I):

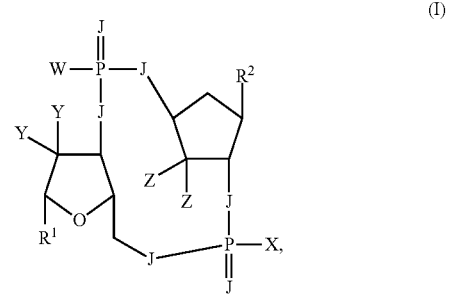

or a pharmaceutically acceptable salt thereof, processes for the preparation of these compounds, compositions containing these compounds, and the uses of these compounds.

6 Claims, No Drawings

(56) References Cited

OTHER PUBLICATIONS

International Search Report and the Written Opinion of the International Searching Authority, PCT/IB2019/052009 dated May 15, 2019.
Che et al., "Structural Flexibility and Conformation Features of Cyclic Dinucleotides in Aqueous Solutions" The Journal of Physical Chemistry, 2016, pp. 2670-2680, 120.
Corrales, et al., "Direct Activation of STING in the Tumor Microenvironment Leads to Potent and Systemic Tumor Regression and Immunity", Cell Reports, 2015, pp. 1018-1030, 11.
Fuertes, et al., "Host type I IFN signals are required for antitumor CD8+ T cell responses through CD8alpha+ dendritic cells", The Journal of Experimental Medicine, 2011, pp. 2005-2016, 208(10).
Harding, et al., "Mitotic progression following DNA damage enables pattern recognition within micronuclei", Nature, 2017, pp. 466-480, 548.
Sivick, et al., "Magnitude of Therapeutics STING Activation Determines CD8+ T Cell-Mediated Anti-tumor Immunity", Cell Reports, 2018, pp. 3074-3085, 25.
Sivick, et al., "Magnitude of Therapeutics STING Activation Determines CD8+ T Cell-Mediated Anti-tumor Immunity", Cell Reports Correction, 2018, pp. 3074-3085, e1-e5, 25.
Vanpouille-Box, "DNA exonuclease Trex1 regulates radiotherapy-induced tumor immunogenicity", Nature Communications, 2017, pp. 1-15.
Woo, et al, "STING-Dependent Cytosolic DNA Sensing Mediates Innate Immune Recognition of Immunogenic Tumors", Immunity, 2014, pp. 830-842, 41.

CYCLOPENTANE-BASED MODULATORS OF STING (STIMULATOR OF INTERFERON GENES)

CROSS-REFERENCE TO RELATED APPLICATIONS

This Application is a continuation application from U.S. Non-Provisional application Ser. No. 16/297,910, filed on Mar. 11, 2019, now issued as U.S. Pat. No. 10,538,542, which claims the benefit of U.S. Provisional Application No. 62/643,467, filed on Mar. 15, 2018 and U.S. Provisional Application No. 62/666,204, filed on May 3, 2018 and U.S. Provisional Application No. 62/742,532, filed on Oct. 8, 2018, and U.S. Provisional Application No. 62/809,990, filed on Feb. 25, 2019, each of which is incorporated by reference herein in its entirety.

FIELD OF THE INVENTION

This invention relates to novel cyclopentane-based activators of STING (Stimulator of Interferon Genes) useful in the treatment of abnormal cell growth, such as cancer, in mammals. This invention also relates to a method of using such compounds in the treatment of abnormal cell growth in mammals, especially humans, and to pharmaceutical compositions as anticancer agents.

BACKGROUND OF THE INVENTION

The innate immune system is the first line of defense which is initiated by pattern recognition receptors (PRRs) upon detection of ligands from pathogens as well as damage associated molecular patterns. A growing number of these receptors have been identified, which now includes sensors of double stranded DNA and unique nucleic acids called cyclic dinucleotides (CDNs). Activation of PRRs leads to up regulation of genes involved in the inflammatory response, including type 1 interferons (IFNs), proinflammatory cytokines and chemokines which suppress pathogen replication and facilitate adaptive immunity.

The adaptor protein STING, also know as TMEM 173, has been identified as a central signalling molecule in the innate immume sensing pathway in response to cytosolic nucleic acids. Activation of STING results in up-regulation of IRF3 and NFκB pathways leading to induction of INF-β and other cytokines. STING is critical for responses to cytosolic DNA from pathogens or of host origin, and in responce to CDNs, sometime referred to second messengers. G. N. Barber, "Sting: infection, inflammation and cancer," *Nat. Rev. Immun.*, 2015, 15, pp 760.

CDNs were first identified as bacterial messengers responsible for controlling numerous responses in prokaryotic cells. Bacterial CDNs, such as c-di-GMP are symmetrical molecules characterized by two 3',5' phosphodiester linkages. Direct activation of STING by bacterial CDNs has recently been confirmed through X-ray crystallography. Bacterial CDNs have consequently attracted interest as potential vaccine adjuvants.

More recently, the respose to cytosolic DNA has been shown to involve generation of endogenous CDNs by an enzyme called cyclic guanine adenine synthase (cGAS), producing a novel mammalian CDN signalling molecule identified as cyclic guanine adenine monophosphate (cGAMP), which binds to and activates STING. Interaction of cGAMP with STING has also been demonstrated by X-ray crystallography. Unlike bacterial CDNs, cGAMP is an unsymmetrical molecule characterised by its mixed 2',5' and 3',5' phosphodiester linkages. Like bacterial CDNs, cGAMP activates STING leading to induction of type 1 INFs:

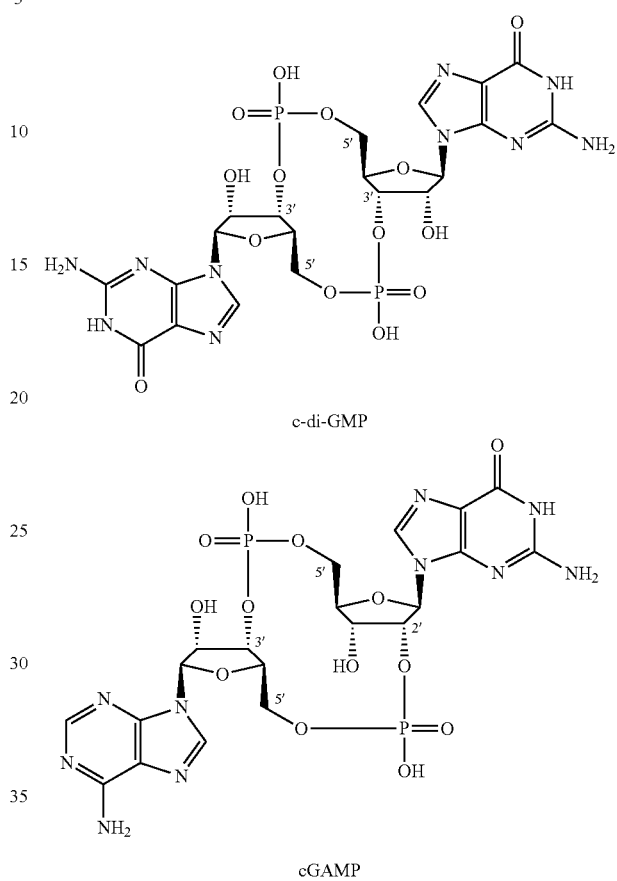

c-di-GMP cGAMP

The role of type 1 INFs in response to invading pathogens is well established. Recombinant IFNα was the first approved biological therapeutic and has become an important therapy in viral infections and in cancer. INFs are also know to be potent modulators of the immune response, acting on cells of the immune system.

Given its role in regulating various biological processes, STING is an attractive target for modulation with small molecules. Nevertheless, to date, few effective STING activators have been developed or have entered the clinic.

SUMMARY OF THE INVENTION

Administration of a small molecule compound which could stimulate the innate immune response, including the activation of type 1 INF and other cytokines, could become an important strategy for the treatment and prevention of human diseases including viral infections and cancer. This type of immunomodulatory strategy has the potential to identify compounds which may be useful not only in infectious diseases but also cancer, allergic diseases, and as vaccine adjuvants.

Certain compounds of the invention have been shown to bind to STING and to induce type 1 INF and other cytokines and co-stimulatory factors on incubation with human dendritic cells (DCs) and peripheral blood mononucleocytes (PBMCs). Compounds which induce human INFs may be useful in the treatment of various disorders, for example the treatment of allergic diseases and other inflammatory conditions. Certain compounds of the invention may bind to STING but act as antagonists and these could be useful in the treatment of various autoimmune diseases.

It is envisioned that targeting STING with activating or inhibiting agents may be a promising approach for treating diseases and conditions in which modulation of the type 1 INF pathway is beneficial, including inflammatory diseases, allergic and autoimmune diseases, infectious diseases, cancer and as vaccine adjuvants.

Each of the embodiments of the non-CDN compounds of the present invention described below can be combined with any other embodiment of the compounds of the present invention described herein not inconsistent with the embodiment with which it is combined. Furthermore, each of the embodiments below describing the invention envisions within its scope pharmaceutically acceptable salts of the compounds of the invention. Accordingly, the phrase "or a pharmaceutically acceptable salt thereof" is implicit in the description of all compounds described herein.

The invention includes embodiments wherein there is provided a compound of formula (I):

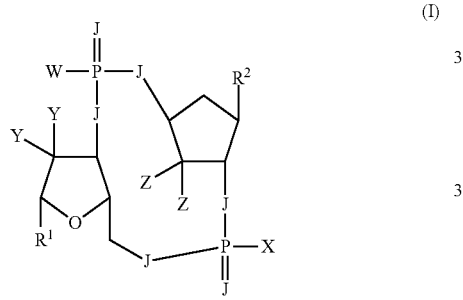

(I)

or a pharmaceutically acceptable salt thereof, wherein each J is independently oxygen (O) or sulfur (S);
$R^1$ is selected from:

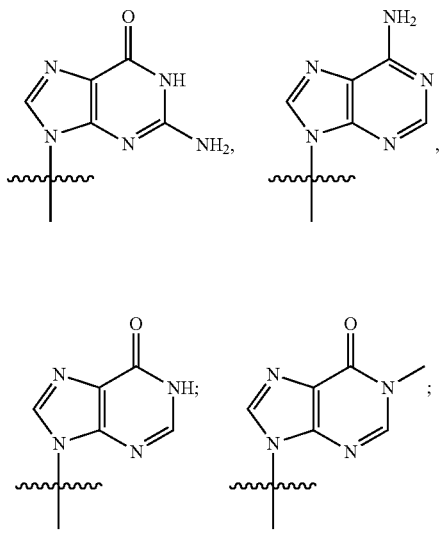

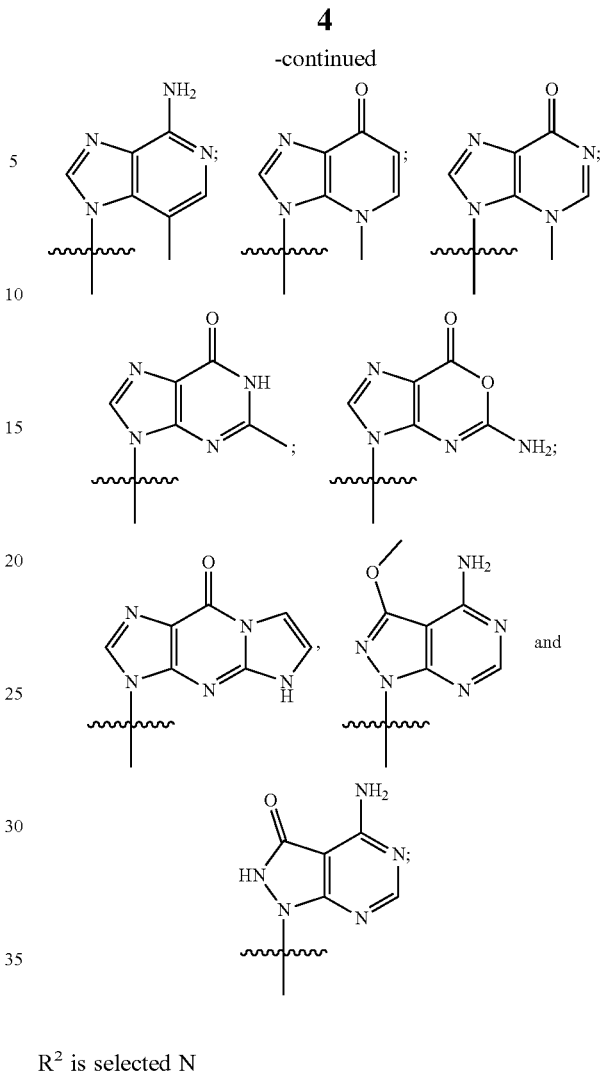

$R^2$ is selected N

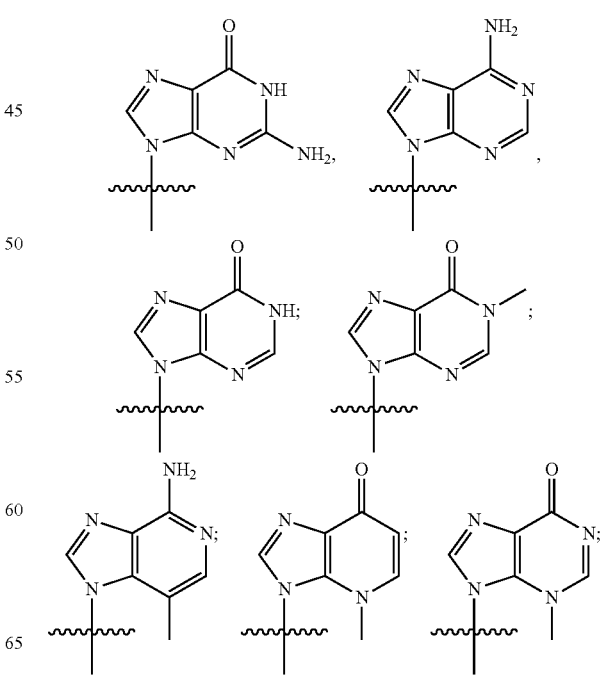

-continued

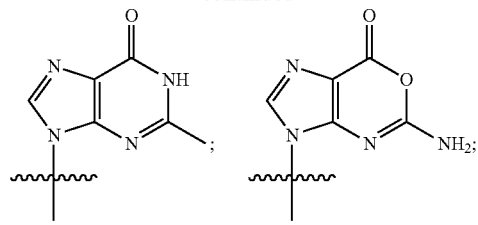

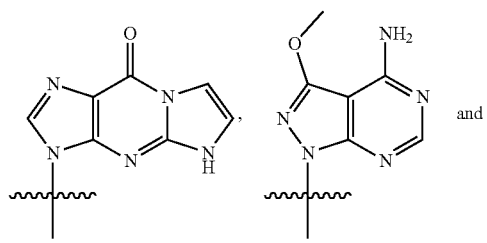

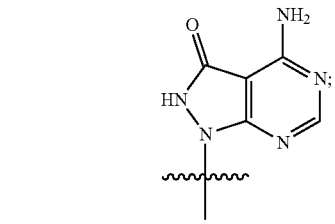

W is OH, SH, O⁻M⁺ or S⁻M⁺, where M⁺ represents a cationic counter-ion;

X is OH, SH, O⁻M⁺ or S⁻M⁺, where M⁺ represents a cationic counter-ion;

each Y is independently selected from hydrogen, halogen, $C_1$-$C_6$ alkyl, substituted $C_1$-$C_6$ alkyl, $N(R^3)_2$, and $OR^4$, or the two Y substituents join to form a 3-5 membered spirocyclic ring system comprising 0-1 heteroatoms;

each Z is independently selected from hydrogen, halogen, $C_1$-$C_6$ alkyl, substituted $C_1$-$C_6$ alkyl, $N(R^3)_2$, and $OR^4$, or the two Z substituents join to form a 3-5 membered spirocyclic ring system comprising 0-1 heteroatoms; and $R^3$ and $R^4$ are each independently hydrogen or $C_1$-$C_6$ alkyl.

The invention also includes embodiments wherein there is provided a compound of formula (II) (which is a sub-set of formula (I)):

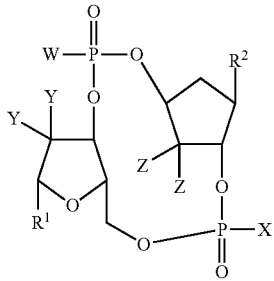

(II)

or a pharmaceutically acceptable salt thereof, wherein $R^1$ is selected from:

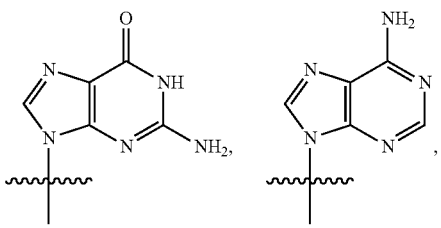

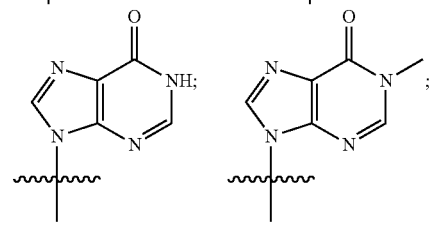

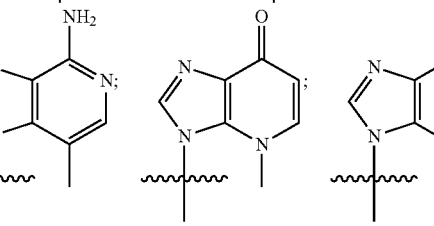

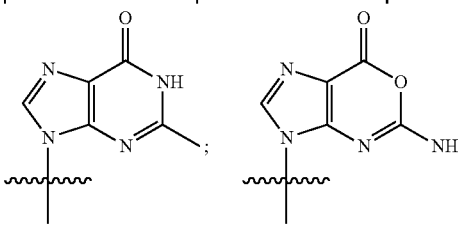

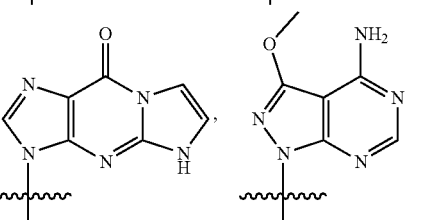

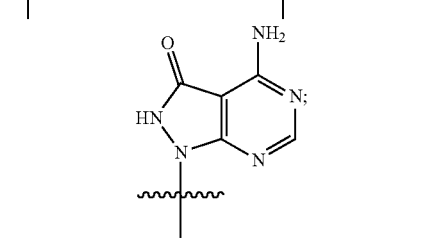

$R^2$ is selected from:

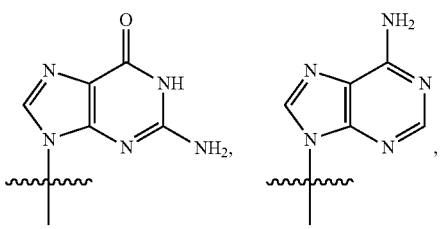

-continued

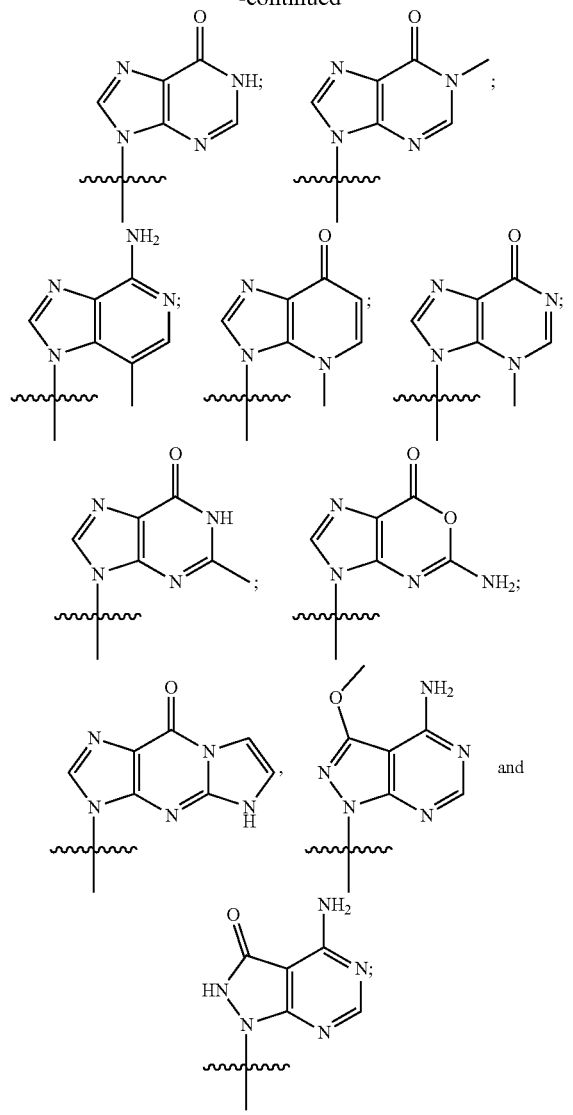

and

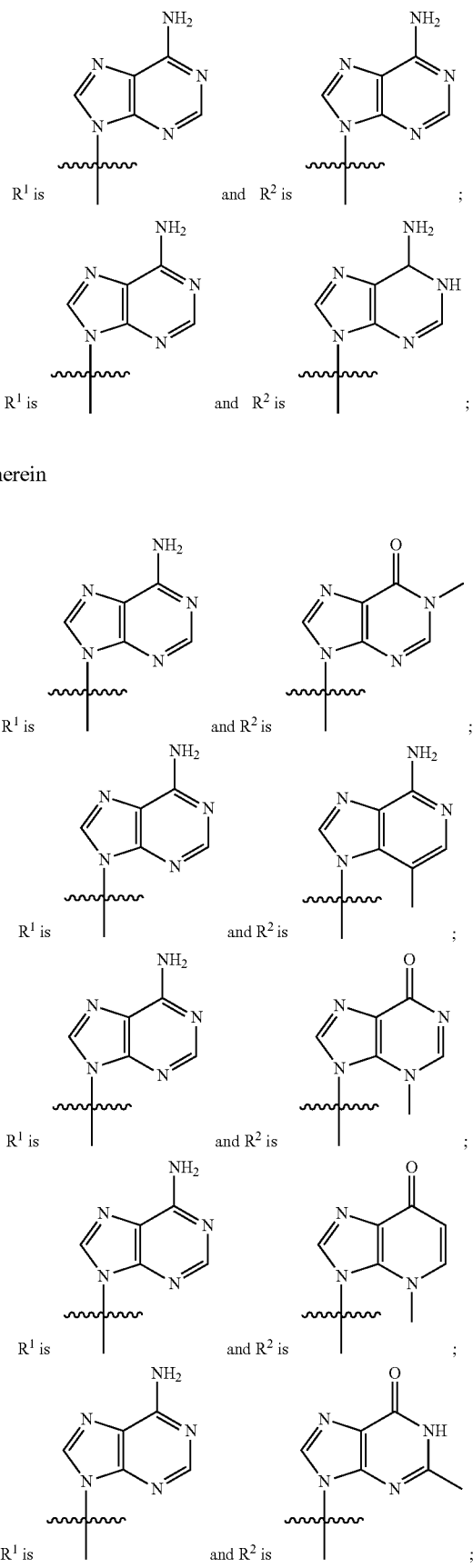

wherein

W is OH, SH, O⁻M⁺ or S⁻M⁺, where M⁺ represents a cationic counter-ion;
X is OH, SH, O⁻M⁺ or S⁻M⁺, where M⁺ represents a cationic counter-ion;
each Y is independently selected from hydrogen, halogen, $C_1$-$C_6$ alkyl, substituted $C_1$-$C_6$ alkyl, $N(R^3)_2$, and $OR^4$, or the two Y substituents join to form a 3-5 membered spirocyclic ring system comprising 0-1 heteroatoms;
each Z is independently selected from hydrogen, halogen, $C_1$-$C_6$ alkyl, substituted $C_1$-$C_6$ alkyl, $N(R^3)_2$, and $OR^4$, or the two Z substituents join to form a 3-5 membered spirocyclic ring system comprising 0-1 heteroatoms; and
$R^3$ and $R^4$ are each independently hydrogen or $C_1$-$C_6$ alkyl.

Other embodiments of the invention include compounds of formula (I) and/or formula (II) wherein M⁺ is selected from the group consisting of sodium, potassium, calcium, ammonium, triethylammonium, trimethylammonium and magnesium. Other counter ions are also useful and are included within the scope of the invention. Note that each counter-ion M⁺ may be the same, or in some embodiments may be different from one another.

Various combinations of bases $R^1$ and $R^2$ are embodied by the invention. Thus in certain embodiments

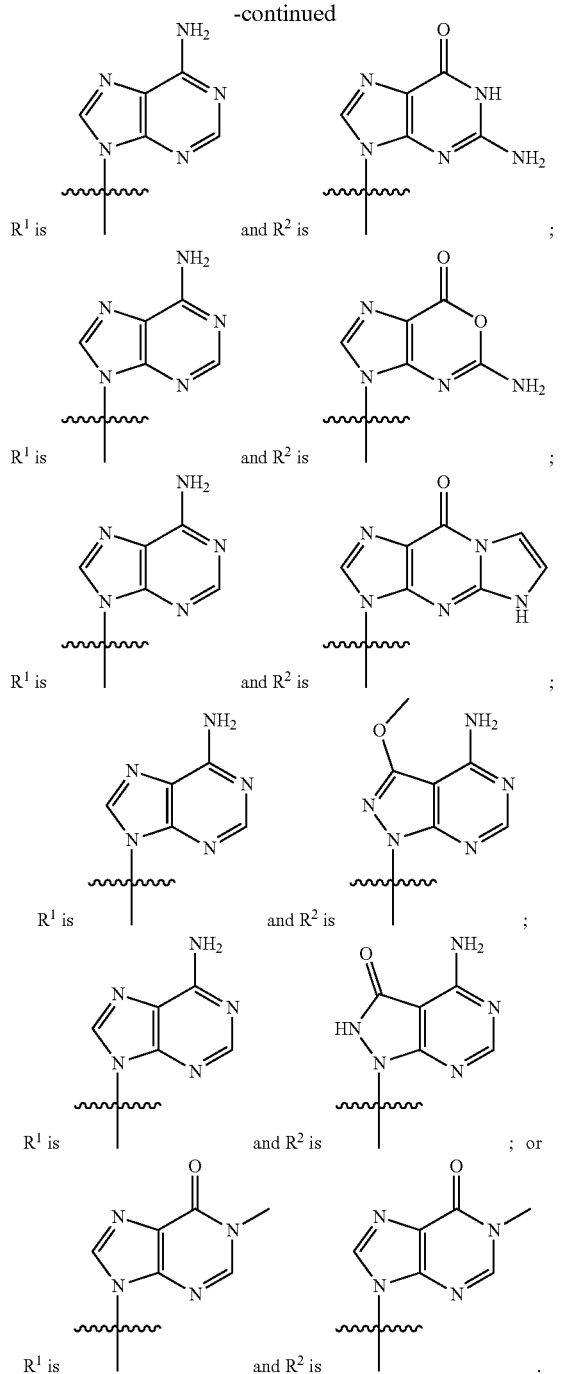

Other bases ($R^1$ and $R^2$), and other combinations of bases, are also included within the present invention.

Additional embodiments of the invention include those where one or both Y is/are halogen. This includes embodiments where one Y is hydrogen and the other Y is a halogen. In certain of these embodiments the halogen(s) is/are fluorine.

Additional embodiments of the invention include those where one Z is hydrogen and the other Z is $OR^4$. In certain of these embodiments one or more $R^4$ is H (hydrogen) and thus at least one Z is OH.

Additional embodiments of the invention include those where W is —SH and X is —SH.

Additional embodiments of the invention include those where W is —OH and X is —OH.

Further embodiments of the invention include a compound selected from:

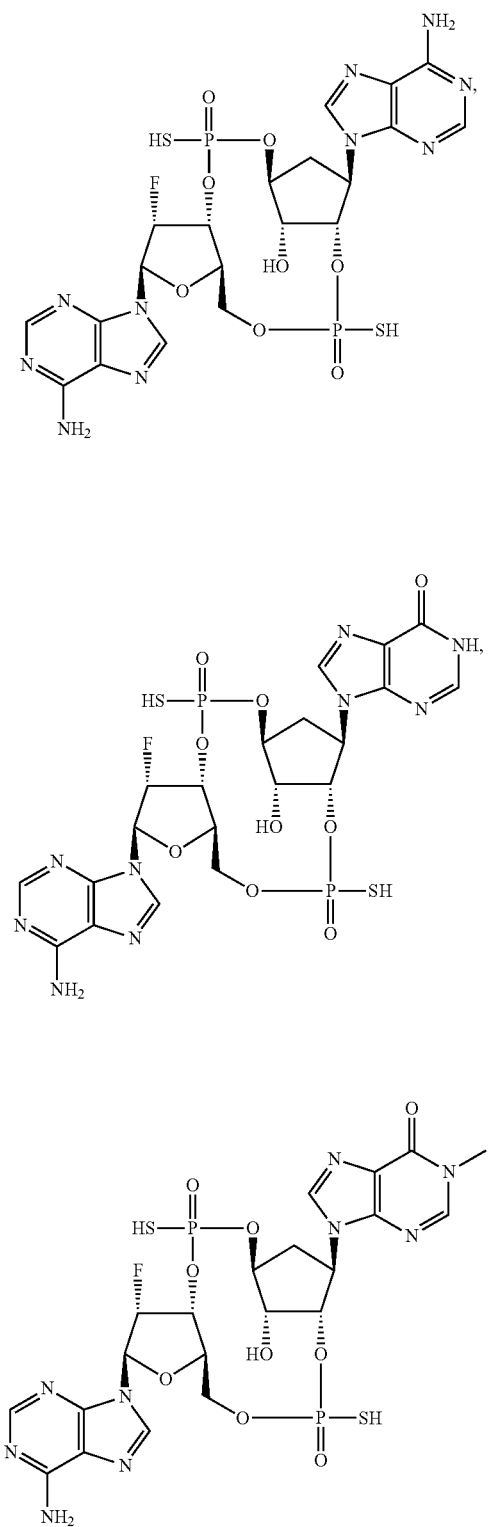

11
-continued
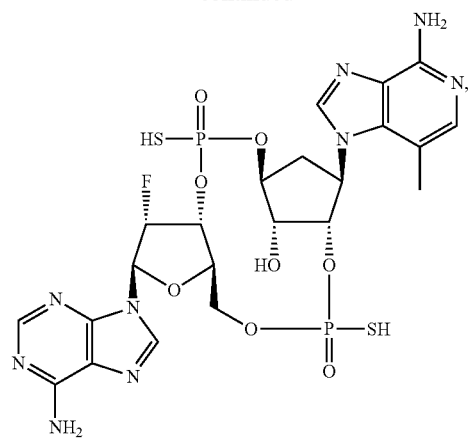
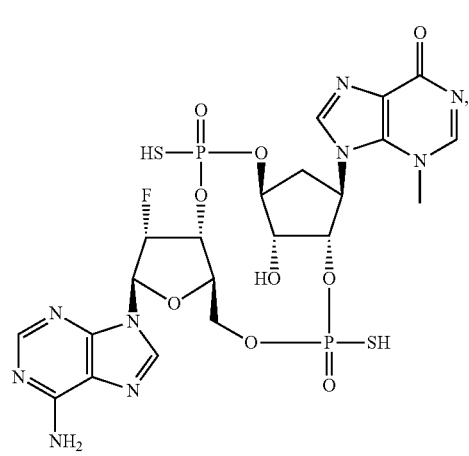
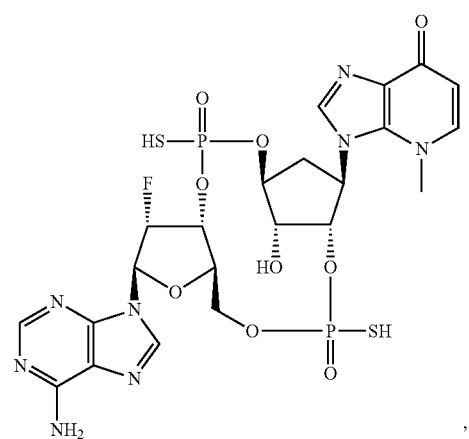
12
-continued
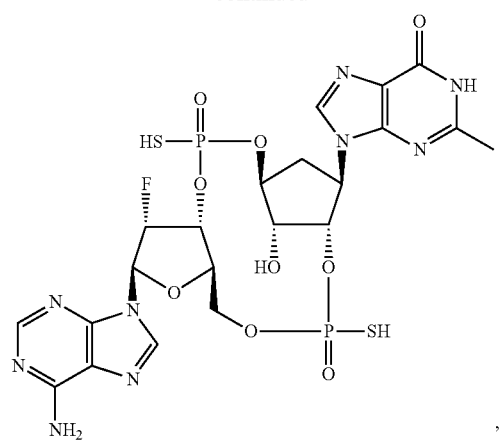
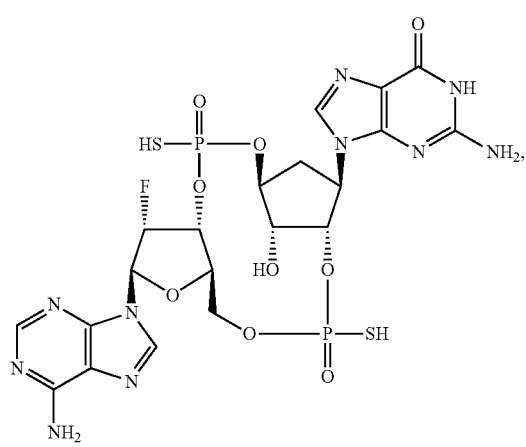
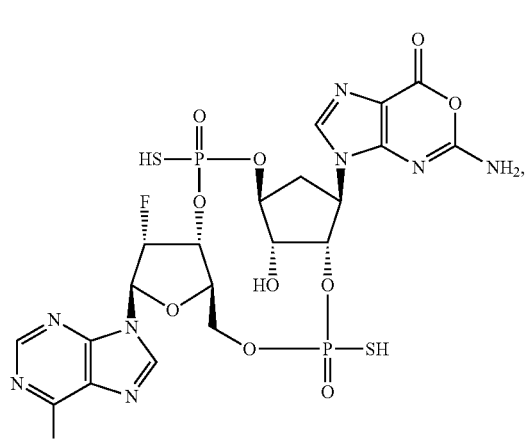

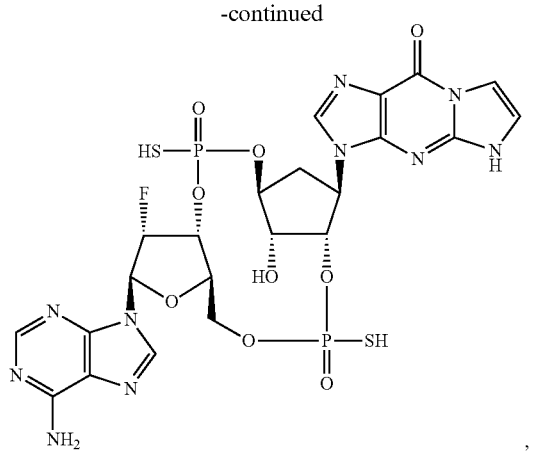
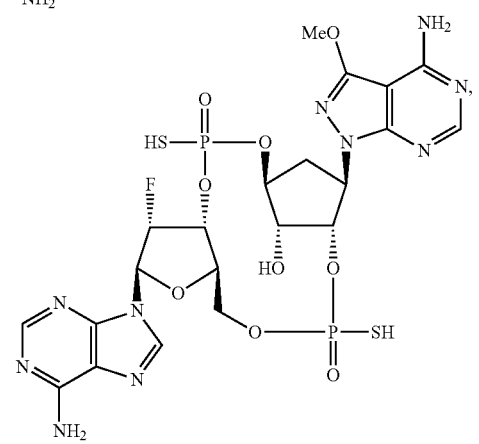
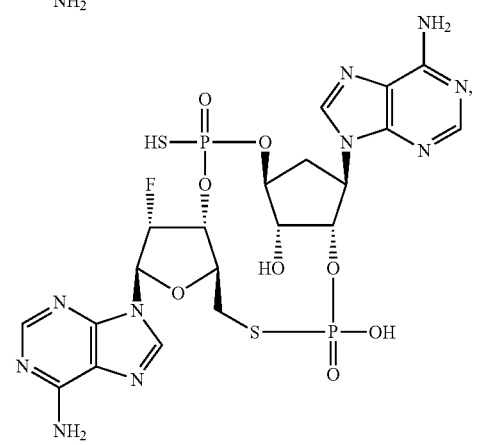
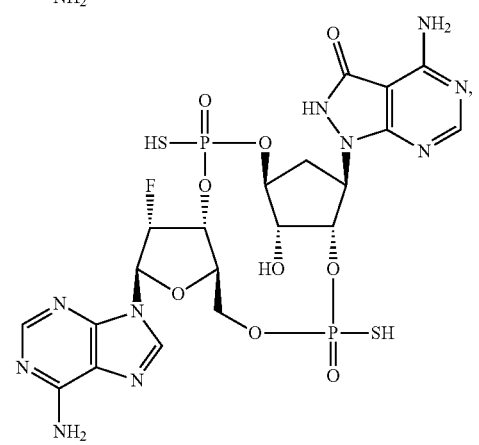
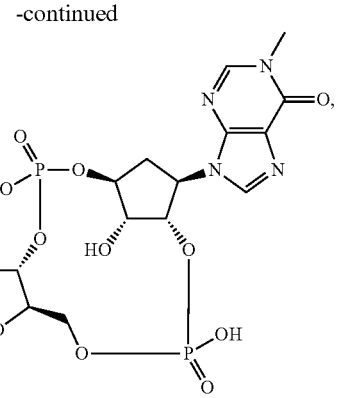
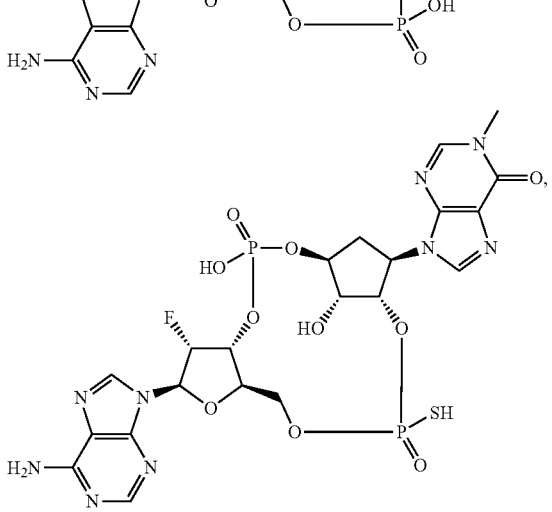
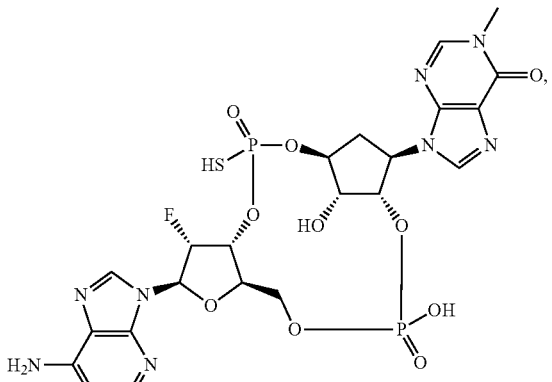
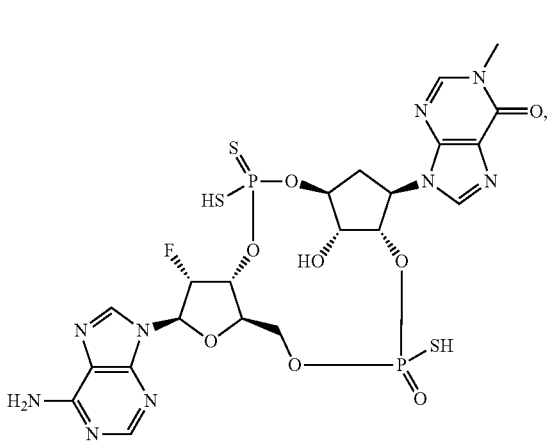

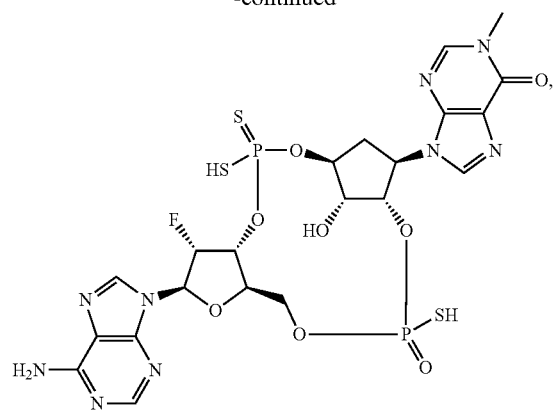
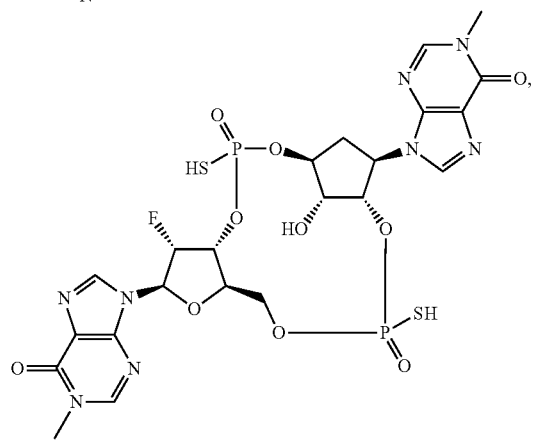
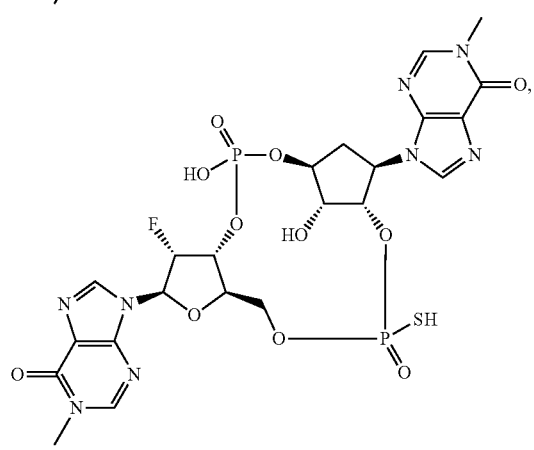
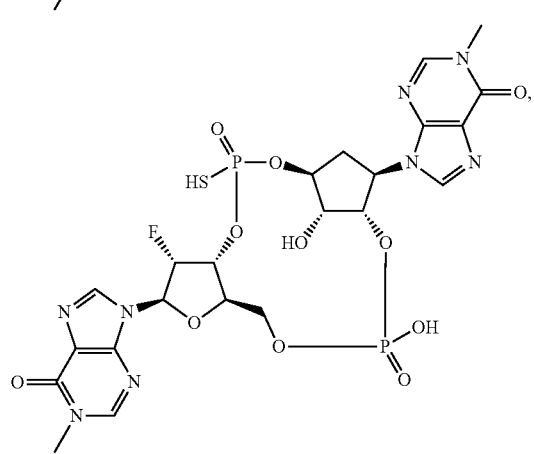
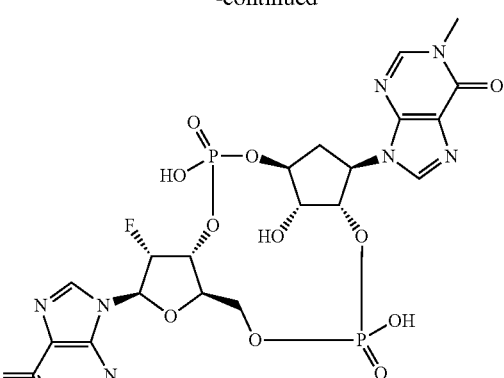
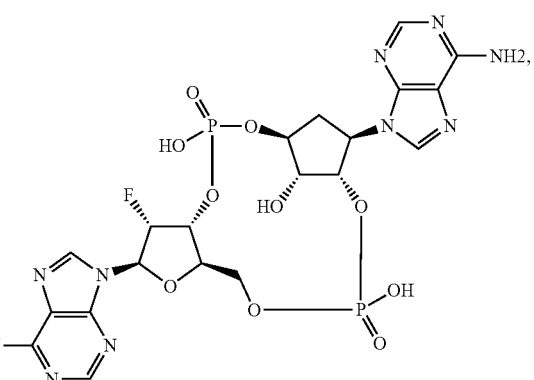
or a pharmaceutically acceptable salt thereof.
Further embodiments of the invention include a compound selected from:
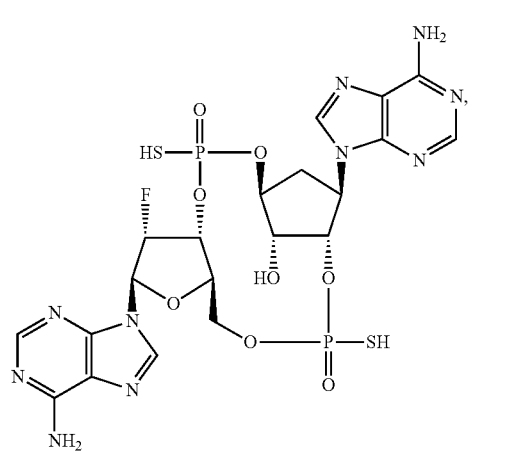

17
-continued
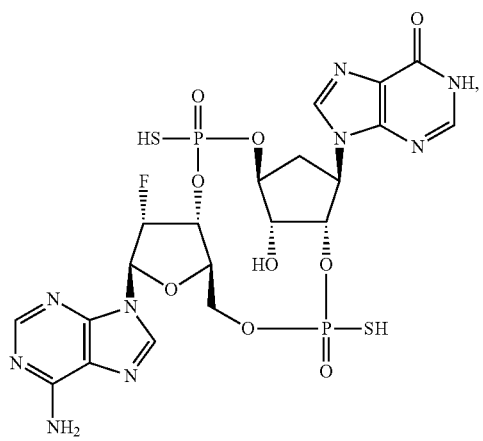
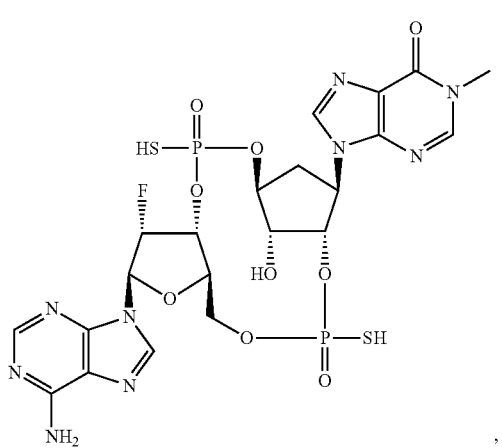
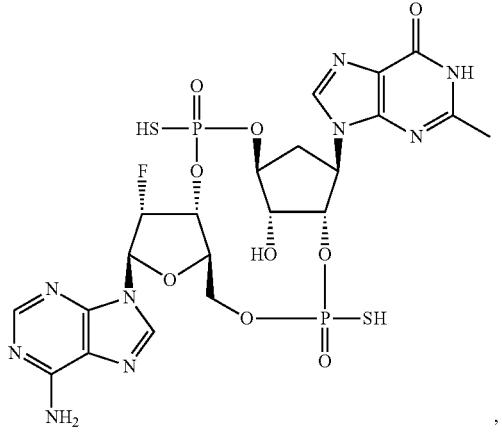
18
-continued
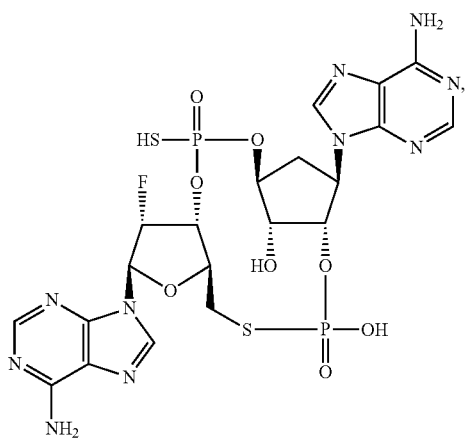
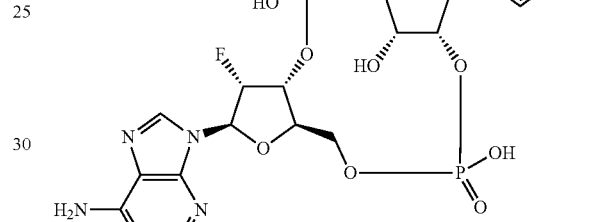
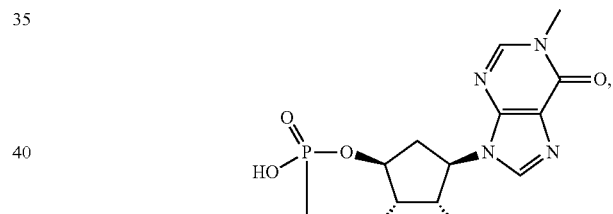
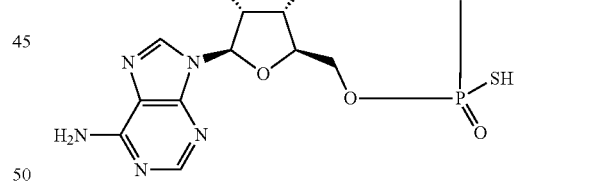
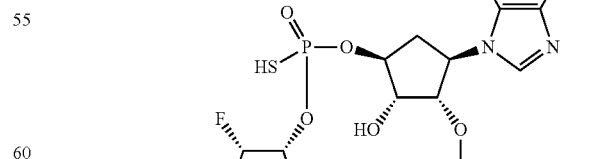
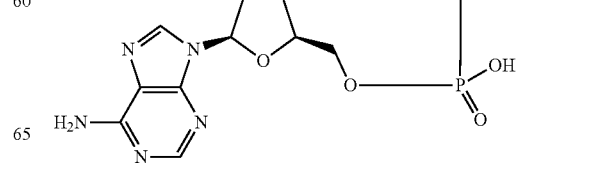

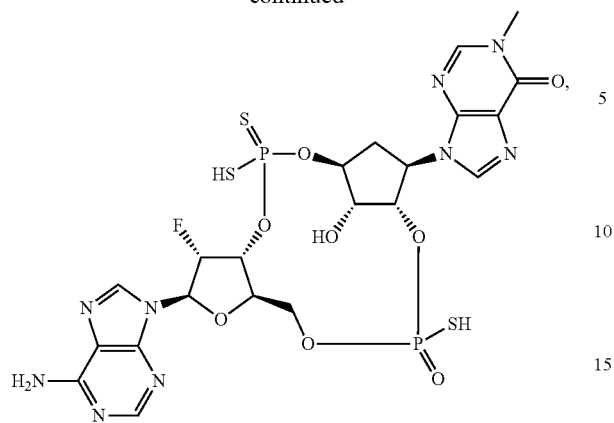
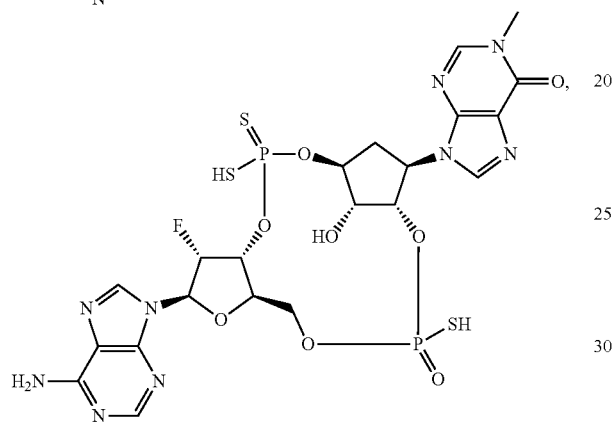
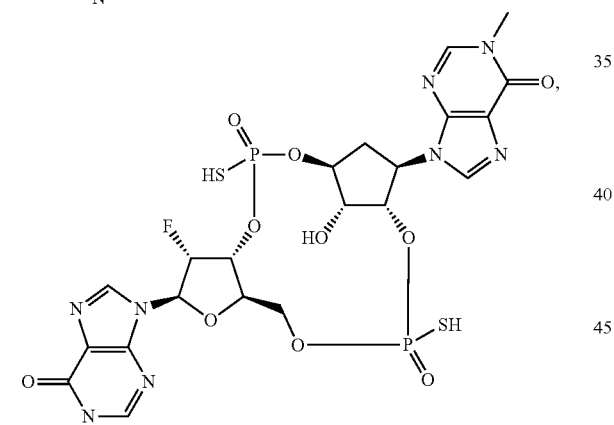
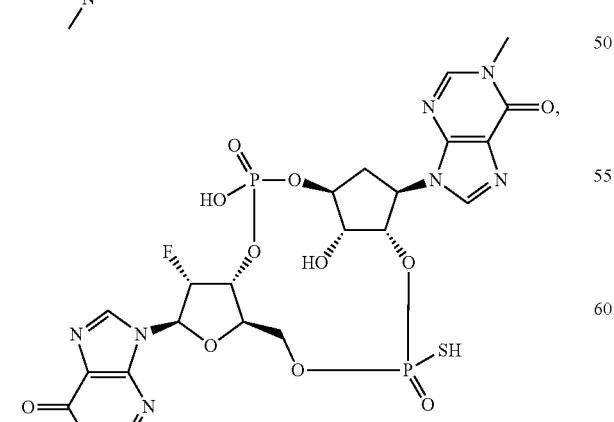
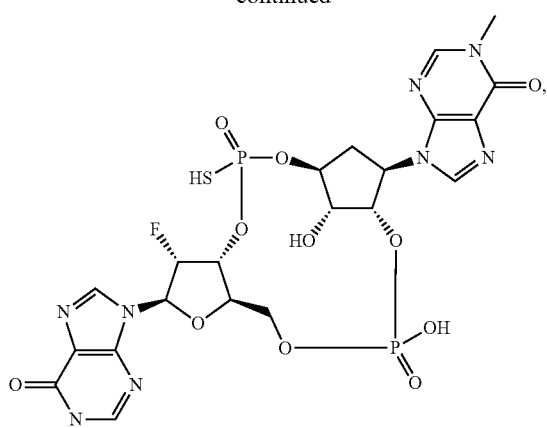
or a pharmaceutically acceptable salt thereof.
Further embodiments of the invention include a compound selected from:

21
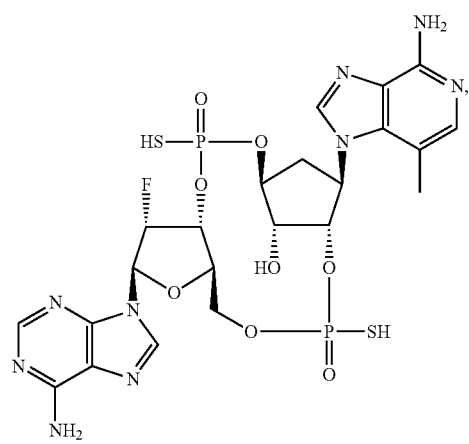
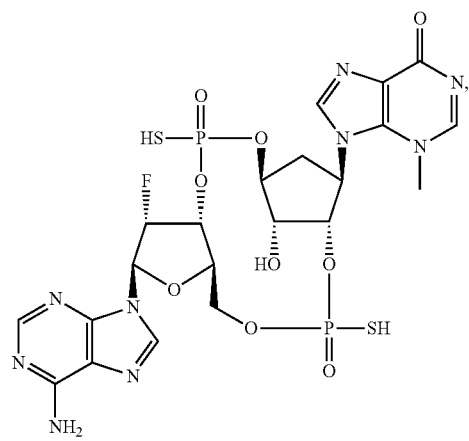
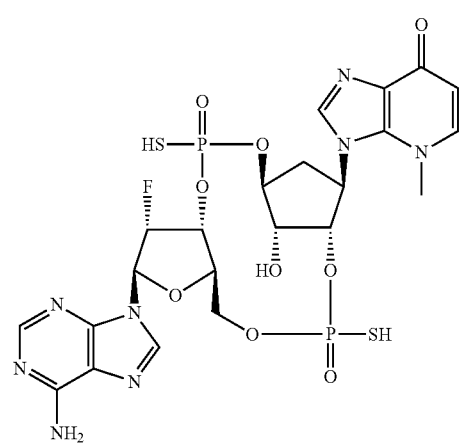
22
-continued
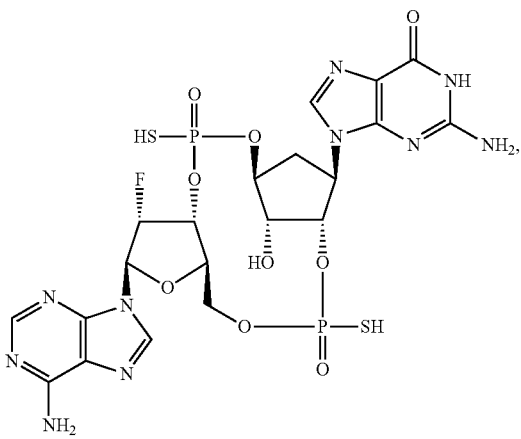
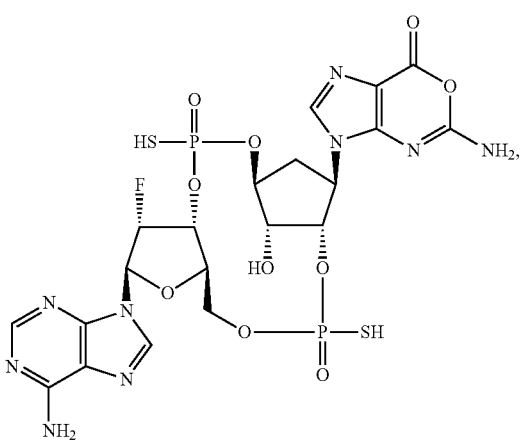
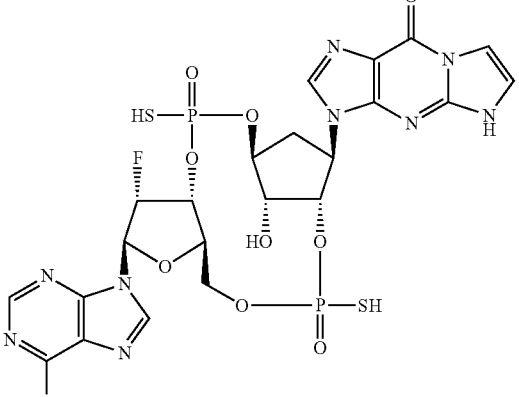

-continued

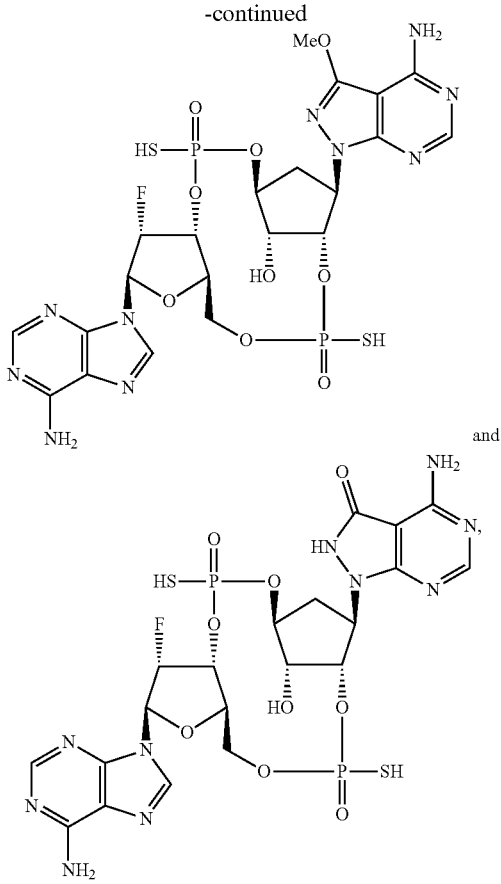

and or a pharmaceutically acceptable salt thereof.

Further embodiments of the invention include a pharmaceutical composition comprising a compound or salt as described herein, or a pharmaceutically acceptable salt thereof, and a pharmaceutically acceptable carrier. Optionally, such compositions may comprise a compound or salt as described herein which is a component of an antibody-drug conjugate; and/or may comprise a compound as described herein which is a component of a particle-based delivery system.

Also embodied in the invention is a method of treating abnormal cell growth in a mammal, the method comprising administering to the mammal a therapeutically effective amount of a compound or salt as described herein. This method may (or may not) employ a compound or salt as described herein as a component of an antibody-drug conjugate, or as a component of a particle-based delivery system. In such embodiments the abnormal cell growth may be cancer. If the abnormal cell growth is cancer, the cancer to be treated may be lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, or pituitary adenoma.

Also embodied in the invention is the use of a compound or salt as described herein for the preparation of a medicament useful in the treatment of abnormal cell growth in a mammal. In such embodiments the abnormal cell growth may be cancer. If the abnormal cell growth is cancer, the cancer to be treated may be lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, or pituitary adenoma.

Further still, embodiments of the invention include those where there is provided a method of upregulating the activity of STING in a mammal, comprising the step of administering to said mammal an effective amount of a compound or salt as described herein; and/or a method of increasing interferon-beta levels in a mammal, comprising the step of administering to said mammal an effective amount of a compound or salt as described herein.

Definitions

Unless otherwise stated, the following terms used in the specification and claims have the meanings discussed below. Variables defined in this section, such as R, X, n and the like, are for reference within this section only, and are not meant to have the same meaning as may be used outside of this definitions section. Further, many of the groups defined herein can be optionally substituted. The listing in this definitions section of typical substituents is exemplary and is not intended to limit the substituents defined elsewhere within this specification and claims.

"Alkenyl" refers to an alkyl group, as defined herein, consisting of at least two carbon atoms and at least one carbon-carbon double bond. Representative examples include, but are not limited to, ethenyl, 1-propenyl, 2-propenyl, 1-, 2-, or 3-butenyl, and the like. "Alkenylene" refers to a di-valent form of alkenyl.

"Alkoxy" refers to —O-alkyl where alkyl is preferably $C_1$-$C_8$, $C_1$-$C_7$, $C_1$-$C_6$, $C_1$-$C_5$, $C_1$-$C_4$, $C_1$-$C_3$, $C_1$-$C_2$ or $C_1$ alkyl.

"Alkyl" refers to a saturated aliphatic hydrocarbon radical including straight chain and branched chain groups of 1 to 20 carbon atoms ("$(C_1$-$C_{20})$alkyl"), preferably 1 to 12 carbon atoms ("$(C_1$-$C_{12})$alkyl"), more preferably 1 to 8 carbon atoms ("$(C_1$-$C_8)$alkyl"), or 1 to 6 carbon atoms ("$(C_1$-$C_6)$alkyl"), or 1 to 4 carbon atoms ("$(C_1$-$C_4)$alkyl"). Examples of alkyl groups include methyl, ethyl, propyl, 2-propyl, n-butyl, iso-butyl, tert-butyl, pentyl, neopentyl, and the like. Alkyl may be substituted or unsubstituted. Typical substituent groups include cycloalkyl, aryl, heteroaryl, heteroalicyclic, hydroxy, alkoxy, aryloxy, mercapto, alkylthio, arylthio, cyano, halogen, carbonyl, thiocarbonyl, O-carbamyl, N-carbamyl, O-thiocarbamyl, N-thiocarbamyl, C-amido, N-amido, C-carboxy, O-carboxy, nitro, silyl, amino and —NR$^x$R$^y$, where R$^x$ and R$^y$ are for example hydrogen, alkyl, cycloalkyl, aryl, carbonyl, acetyl, sulfonyl, trifluoromethanesulfonyl and, combined, a five- or six-member heteroalicyclic ring. "Haloalkyl" for instance (C$_1$-C$_8$)haloalkyl, refers to an alkyl having one or more, halogen substituents. "Alkylene" refers to a di-valent form of alkyl.

"Alkynyl" refers to an alkyl group, as defined herein, consisting of at least two carbon atoms and at least one carbon-carbon triple bond. Representative examples include, but are not limited to, ethynyl, 1-propynyl, 2-propynyl, 1-, 2-, or 3-butynyl, and the like. "Alkynylene" refers to a di-valent form of alkynyl.

"Amino" refers to an —NR$^x$R$^y$ group, wherein R$^x$ and R$^y$ are both hydrogen.

"Cyano" refers to a —C≡N group. Cyano may be expressed as CN.

"(C$_3$-C$_5$)cycloalkyl" refers to a 3 to 5 member all-carbon monocyclic ring. Examples, without limitation, of cycloalkyl groups are cyclopropane, cyclobutane, cyclopentane, and cyclopentene. Typical substituent groups include alkyl, alkoxy, cyano, halo, carbonylC-carboxy, O-carboxy, O-carbamyl, N-carbamyl, amino and —NR$^x$R$^y$, with R$^x$ and R$^y$ as defined above. Illustrative examples of cycloalkyl are derived from, but not limited to, the following: ▷ and ☐.

"Halogen" or the prefix "halo" refers to fluoro, chloro, bromo and iodo. Preferably halogen refers to fluoro or chloro.

"Heteroatom" refers to an atom selected from the group consisting of O, N, Si, S and/or P, and wherein the nitrogen and sulfur atoms may optionally be oxidized.

"Heterocyclyl" refers to a monocyclic or fused ring system having 3 to 12 ring atoms containing one, two, three or four ring heteroatoms selected from N, O, and S(O)$_n$ (where n is 0, 1 or 2), and 1-9 carbon atoms The rings may also have one or more double bonds. However, the rings do not have a completely conjugated pi-electron system. Preferred heterocycles include (C$_2$-C$_6$)heterocycles in accordance with the definition above. Examples of suitable saturated heteroalicyclic groups include, but are not limited to:

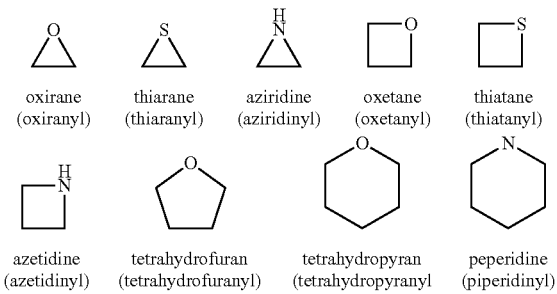

oxirane (oxiranyl)  thiarane (thiaranyl)  aziridine (aziridinyl)  oxetane (oxetanyl)  thiatane (thiatanyl)

azetidine (azetidinyl)  tetrahydrofuran (tetrahydrofuranyl)  tetrahydropyran (tetrahydropyranyl)  peperidine (piperidinyl)

The heterocyclyl group is optionally substituted with one or two substituents independently selected from halo, lower alkyl.

"Hydroxy" or "hydroxyl" refers to an —OH group.

"In vitro" refers to procedures performed in an artificial environment such as, e.g., without limitation, in a test tube or culture medium.

"In vivo" refers to procedures performed within a living organism such as, without limitation, a mouse, rat, rabbit and/or human.

"Optional" or "optionally" means that the subsequently described event or circumstance may but need not occur, and that the description includes instances where the event or circumstance occurs and instances in which it does not. For example, "heterocycle group optionally substituted with an alkyl group" means that the alkyl may but need not be present, and the description includes situations where the heterocycle group is substituted with an alkyl group and situations where the heterocycle group is not substituted with the alkyl group.

"Organism" refers to any living entity comprised of at least one cell. A living organism can be as simple as, for example, a single eukariotic cell or as complex as a mammal, including a human being.

A "pharmaceutically acceptable excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

As used herein, the term "pharmaceutically acceptable salt" refers to those salts which retain the biological effectiveness and properties of the parent compound. Such salts include:

(i) acid addition salts, which can be obtained by reaction of the free base of the parent compound with inorganic acids such as hydrochloric acid, hydrobromic acid, nitric acid, phosphoric acid, sulfuric acid, and perchloric acid and the like, or with organic acids such as acetic acid, oxalic acid, (D) or (L) malic acid, maleic acid, methanesulfonic acid, ethanesulfonic acid, p-toluenesulfonic acid, salicylic acid, tartaric acid, citric acid, succinic acid or malonic acid and the like; or (ii) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, trialkylamonium and the like.

A "pharmaceutical composition" refers to a mixture of one or more of the compounds described herein, or physiologically/pharmaceutically acceptable salts, solvates, hydrates or prodrugs thereof, with other chemical components, such as physiologically/pharmaceutically acceptable carriers and excipients. The purpose of a pharmaceutical composition is to facilitate administration of a compound to an organism.

As used herein, a "physiologically/pharmaceutically acceptable carrier" refers to a carrier or diluent that does not cause significant irritation to an organism and does not abrogate the biological activity and properties of the administered compound.

"Therapeutically effective amount" refers to that amount of the compound being administered which will relieve to some extent one or more of the symptoms of the disorder being treated. In reference to the treatment of cancer, a therapeutically effective amount refers to that amount which has at least one of the following effects:

(1) reducing the size of the tumor;
(2) inhibiting (that is, slowing to some extent, preferably stopping) tumor metastasis;
(3) inhibiting to some extent (that is, slowing to some extent, preferably stopping) tumor growth, and
(4) relieving to some extent (or, preferably, eliminating) one or more symptoms associated with the cancer.

"Treat", "treating" and "treatment" refer to a method of alleviating or abrogating a cellular disorder and/or its attendant symptoms. With regard particularly to cancer, these terms simply mean that the life expectancy of an individual affected with a cancer will be increased or that one or more of the symptoms of the disease will be reduced.

DETAILED DESCRIPTION

General schemes for synthesizing the compounds of the invention can be found in the Examples section herein.

Unless indicated otherwise, all references herein to the inventive compounds include references to salts, solvates, hydrates and complexes thereof, and to solvates, hydrates and complexes of salts thereof, including polymorphs, stereoisomers, and isotopically labeled versions thereof.

Pharmaceutically acceptable salts include acid addition and base salts (including disalts).

Suitable acid addition salts are formed from acids which form non-toxic salts. Examples include the acetate, aspartate, benzoate, besylate, bicarbonate/carbonate, bisulphate/sulfate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulfate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts.

Suitable base salts are formed from bases which form non-toxic salts. Examples include the aluminum, arginine, benzathine, calcium, choline, diethylamine, diolamine, glycine, lysine, magnesium, meglumine, olamine, potassium, sodium, tromethamine and zinc salts. For a review on suitable salts, see "Handbook of Pharmaceutical Salts: Properties, Selection, and Use" by Stahl and Wermuth (Wiley-VCH, Weinheim, Germany, 2002), the disclosure of which is incorporated herein by reference in its entirety.

A pharmaceutically acceptable salt of the inventive compounds can be readily prepared by mixing together solutions of the compound and the desired acid or base, as appropriate. The salt may precipitate from solution and be collected by filtration or may be recovered by evaporation of the solvent. The degree of ionization in the salt may vary from completely ionized to almost non-ionized.

The compounds of the invention may exist in both unsolvated and solvated forms. The term 'solvate' is used herein to describe a molecular complex comprising the compound of the invention and one or more pharmaceutically acceptable solvent molecules, for example, ethanol. The term 'hydrate' is employed when the solvent is water. Pharmaceutically acceptable solvates in accordance with the invention include hydrates and solvates wherein the solvent of crystallization may be isotopically substituted, e.g. $D_2O$, $d_6$-acetone, $d_6$-DMSO.

Also included within the scope of the invention are complexes such as clathrates, drug-host inclusion complexes wherein, in contrast to the aforementioned solvates, the drug and host are present in stoichiometric or non-stoichiometric amounts. Also included are complexes of the drug containing two or more organic and/or inorganic components which may be in stoichiometric or non-stoichiometric amounts. The resulting complexes may be ionized, partially ionized, or non-ionized. For a review of such complexes, see J Pharm Sci, 64 (8), 1269-1288 by Haleblian (August 1975), the disclosure of which is incorporated herein by reference in its entirety.

Also within the scope of the invention are polymorphs, prodrugs, and isomers (including optical, geometric and tautomeric isomers) of the inventive compounds Derivatives of compounds of the invention which may have little or no pharmacological activity themselves but can, when administered to a patient, be converted into the inventive compounds, for example, by hydrolytic cleavage. Such derivatives are referred to as 'prodrugs'. Further information on the use of prodrugs may be found in 'Pro-drugs as Novel Delivery Systems, Vol. 14, ACS Symposium Series (T Higuchi and W Stella) and 'Bioreversible Carriers in Drug Design', Pergamon Press, 1987 (ed. E B Roche, American Pharmaceutical Association), the disclosures of which are incorporated herein by reference in their entireties.

Prodrugs in accordance with the invention can, for example, be produced by replacing appropriate functionalities present in the inventive compounds with certain moieties known to those skilled in the art as 'pro-moieties' as described, for example, in "Design of Prodrugs" by H Bundgaard (Elsevier, 1985), the disclosure of which is incorporated herein by reference in its entirety.

Some examples of prodrugs in accordance with the invention include:

(i) where the compound contains a carboxylic acid functionality —(COOH), an ester thereof, for example, replacement of the hydrogen with $(C_1-C_8)$alkyl;

(ii) where the compound contains an alcohol functionality (—OH), an ether thereof, for example, replacement of the hydrogen with $(C_1-C_6)$alkanoyloxymethyl; and (iii) where the compound contains a primary or secondary amino functionality (—$NH_2$ or —NHR where R≠H), an amide thereof, for example, replacement of one or both hydrogens with $(C_1-C_{10})$alkanoyl.

Further examples of replacement groups in accordance with the foregoing examples and examples of other prodrug types may be found in the aforementioned references.

Finally, certain inventive compounds may themselves act as prodrugs of other of the inventive compounds.

Compounds of the invention containing one or more asymmetric carbon and/or phosphorous atoms can exist as two or more stereoisomers. Where the compounds according to this invention have at least one chiral center, they may accordingly exist as enantiomers. Where the compounds possess two or more chiral centers, they may additionally exist as diastereomers. Similarly, where a compound of the invention contains a cyclopropyl group or other cyclic group where chirality exists, and alkenyl or alkenylene group, geometric cis/trans (or Z/E) isomers are possible. Where the compound contains, for example, a keto or oxime group or an aromatic moiety, tautomeric isomerism ('tautomerism') can occur. A single compound may exhibit more than one type of isomerism.

Included within the scope of the invention are all stereoisomers, geometric isomers and tautomeric forms of the inventive compounds, including compounds exhibiting more than one type of isomerism, and mixtures of one or more thereof. Also included are acid addition or base salts wherein the counterion is optically active, for example, D-lactate or L-lysine, or racemic, for example, DL-tartrate or DL-arginine.

Cis/trans isomers may be separated by conventional techniques well known to those skilled in the art, for example, chromatography and fractional crystallization.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC) or supercritical fluid chromatography (SFC).

Alternatively, the racemate (or a racemic precursor) may be reacted with a suitable optically active compound, for example, an alcohol, or, in the case where the compound contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer(s) by means well known to one skilled in the art.

Stereoisomeric conglomerates may be separated by conventional techniques known to those skilled in the art; see, for example, "Stereochemistry of Organic Compounds" by E L Eliel (Wiley, New York, 1994), the disclosure of which is incorporated herein by reference in its entirety.

The invention also includes isotopically-labeled compounds of the invention, wherein one or more atoms is replaced by an atom having the same atomic number, but an atomic mass or mass number different from the atomic mass or mass number usually found in nature. Examples of isotopes suitable for inclusion in the compounds of the invention include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulfur, such as $^{35}$S. Certain isotopically-labeled compounds of the invention, for example, those incorporating a radioactive isotope, are useful in drug and/or substrate tissue distribution studies. The radioactive isotopes tritium, $^3$H, and carbon-14, $^{14}$C, are particularly useful for this purpose in view of their ease of incorporation and ready means of detection. Substitution with heavier isotopes such as deuterium, $^2$H, may afford certain therapeutic advantages resulting from greater metabolic stability, for example, increased in vivo half-life or reduced dosage requirements, and hence may be preferred in some circumstances. Substitution with positron emitting isotopes, such as $^{11}$C, $^{18}$F, $^{15}$O and $^{13}$N, can be useful in Positron Emission Topography (PET) studies for examining substrate receptor occupancy.

Isotopically-labeled compounds of the invention can generally be prepared by conventional techniques known to those skilled in the art or by processes analogous to those described herein, using an appropriate isotopically-labeled reagent in place of the non-labeled reagent otherwise employed.

Pharmaceutically acceptable solvates in accordance with the invention include those wherein the solvent of crystallization may be isotopically substituted, e.g. $D_2O$, $d_6$-acetone, $d_6$-DMSO.

Compounds of the invention intended for pharmaceutical use may be administered as crystalline or amorphous products, or mixtures thereof. They may be obtained, for example, as solid plugs, powders, or films by methods such as precipitation, crystallization, freeze drying, spray drying, or evaporative drying. Microwave or radio frequency drying may be used for this purpose.

The compounds can be administered alone or in combination with one or more other compounds of the invention. Generally, they will be administered as a formulation in association with one or more pharmaceutically acceptable excipients. The term "excipient" is used herein to describe any ingredient other than the compound(s) of the invention. The choice of excipient will to a large extent depend on factors such as the particular mode of administration, the effect of the excipient on solubility and stability, and the nature of the dosage form.

The compositions described herein can be administered to a host, either alone or in combination with a pharmaceutically acceptable excipient, in an amount sufficient to induce, modify, or stimulate an appropriate immune response. The immune response can comprise, without limitation, specific immune response, non-specific immune response, both specific and non-specific response, innate response, primary immune response, adaptive immunity, secondary immune response, memory immune response, immune cell activation, immune cell proliferation, immune cell differentiation, and cytokine expression. In certain embodiments, the compositions are administered in conjunction with one or more additional compositions including vaccines intended to stimulate an immune response to one or more predetermined antigens; adjuvants; CTLA-4 and PD-1 pathway antagonists, lipids, liposomes, chemotherapeutic agents, immunomodulatory cell lines, etc.

In some aspects of the invention, the methods described herein further include a step of treating a subject with an additional form of therapy. In some aspects, the additional form of therapy is an additional anti-cancer therapy including, but not limited to, chemotherapy, radiation, surgery, hormone therapy, and/or additional immunotherapy.

The disclosed STING modulatory compounds may be administered as an initial treatment, or for treatment of cancers that are unresponsive to conventional therapies. In addition, the disclosed STING modulatory compounds may be used in combination with other therapies (e.g., surgical excision, radiation, additional anti-cancer drugs etc.) to thereby elicit additive or potentiated therapeutic effects and/or reduce cytotoxicity of some anti-cancer agents. The STING modulatory compounds of the invention may be co-administered or co-formulated with additional agents, or formulated for consecutive administration with additional agents in any order.

The STING modulatory compounds the invention may be used in combination with other therapeutic agents including, but not limited to, therapeutic antibodies, ADCs, immuno-modulating agents, cytotoxic agents, and cytostatic agents. A cytotoxic effect refers to the depletion, elimination and/or the killing of a target cells (i.e., tumor cells). A cytotoxic agent refers to an agent that has a cytotoxic and/or cytostatic effect on a cell. A cytostatic effect refers to the inhibition of cell proliferation. A cytostatic agent refers to an agent that has a cytostatic effect on a cell, thereby inhibiting the growth and/or expansion of a specific subset of cells (i.e., tumor cells). An immunomodulating agent refers to an agent that stimulates the immune response though the production of cytokines and/or antibodies and/or modulating T cell function thereby inhibiting or reducing the growth of a subset of cells (i.e., tumor cells) either directly or indirectly by allowing another agent to be more efficacious.

For combination therapies, the STING modulatory compounds are administered within any time frame suitable for performance of the intended therapy. Thus, the single agents may be administered substantially simultaneously (i.e., as a single formulation or within minutes or hours) or consecutively in any order. For example, single agent treatments may be administered within about 1 year of each other, such as within about 10, 8, 6, 4, or 2 months, or within 4, 3, 2 or 1 week(s), or within about 5, 4, 3, 2 or 1 day(s).

The disclosed combination therapies may elicit a synergistic therapeutic effect, i.e., an effect greater than the sum of their individual effects or therapeutic outcomes. For example, a synergistic therapeutic effect may be an effect of at least about two-fold greater than the therapeutic effect elicited by a single agent, or the sum of the therapeutic effects elicited by the single agents of a given combination, or at least about five-fold greater, or at least about ten-fold greater, or at least about twenty-fold greater, or at least about fifty-fold greater, or at least about one hundred-fold greater. A synergistic therapeutic effect may also be observed as an increase in therapeutic effect of at least 10% compared to the therapeutic effect elicited by a single agent, or the sum of the therapeutic effects elicited by the single agents of a given combination, or at least 20%, or at least 30%, or at least 40%, or at least 50%, or at least 60%, or at least 70%, or at least 80%, or at least 90%, or at least 100%, or more. A synergistic effect is also an effect that permits reduced dosing of therapeutic agents when they are used in combination.

The compositions may be administered before, after, and/or together with an additional therapeutic or prophylactic composition or modality. These include, without limitation, B7 costimulatory molecule, interleukin-2, interferon-γ, GM-CSF, CTLA-4 antagonists, OX-40/OX-40 ligand, CD40/CD40 ligand, sargramostim, levamisol, vaccinia virus, Bacille Calmette-Guerin (BCG), liposomes, alum, Freund's complete or incomplete adjuvant, detoxified endotoxins, mineral oils, surface active substances such as lipolecithin, pluronic polyols, polyanions, peptides, and oil or hydrocarbon emulsions. Carriers for inducing a T cell immune response which preferentially stimulate a cytolytic T cell response versus an antibody response are preferred, although those that stimulate both types of response can be used as well. In cases where the agent is a polypeptide, the polypeptide itself or a polynucleotide encoding the polypeptide can be administered. The carrier can be a cell, such as an antigen presenting cell (APC) or a dendritic cell. Antigen presenting cells include such cell types as macrophages, dendritic cells and Bcells. Other professional antigen-presenting cells include monocytes, marginal zone Kupffer cells, microglia, Langerhans' cells, interdigitating dendritic cells, follicular dendritic cells, and T cells. Facultative antigen-presenting cells can also be used. Examples of facultative antigen presenting cells include astrocytes, follicular cells, endothelium and fibroblasts. The carrier can be a bacterial cell that is transformed to express the polypeptide or to deliver a polynucleotide which is subsequently expressed in cells of the vaccinated individual. Adjuvants, such as aluminium hydroxide or aluminum phosphate, can be added to increase the ability of the vaccine to trigger, enhance, or prolong an immune response. Additional materials, such as cytokines, chemokines, and bacterial nucleic acid sequences, like CpG, a toll-like receptor (TLR) 9 agonist as well as additional agonists for TLR 2, TLR 4, TLR 5, TLR 7, TLR 8, TLR9, including lipoprotein, LPS, monophosphoryl lipid A, lipoteichoic acid, imiquimod, resiquimod, and in addition retinoic acid-inducible gene I (RIG-I) agonists such as poly I:C, used separately or in combination with the described compositions are also potential adjuvants. Other representative examples of adjuvants include the synthetic adjuvant QS-21 comprising a homogeneous saponin purified from the bark of *Quillaja saponaria* and *Colynebacterium parvum* (McCune et al., Cancer, 1979; 43:1619). It will be understood that the adjuvant is subject to optimization. In other words, the skilled artisan can engage in routine experimentation to determine the best adjuvant to use.

Pharmaceutical compositions suitable for the delivery of compounds of the invention and methods for their preparation will be readily apparent to those skilled in the art. Such compositions and methods for their preparation can be found, for example, in 'Remington's Pharmaceutical Sciences', 19th Edition (Mack Publishing Company, 1995), the disclosure of which is incorporated herein by reference in its entirety.

The compounds of the invention may be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular, subcutaneous and intratumoral. Suitable devices for parenteral administration include needle (including micro needle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilization, may readily be accomplished using standard pharmaceutical techniques well known to those skilled in the art.

The solubility of compounds of the invention used in the preparation of parenteral solutions may be increased by the use of appropriate formulation techniques, such as the incorporation of solubility-enhancing agents. Formulations for parenteral administration may be formulated to be immediate and/or modified release. Modified release formulations include delayed-, sustained-, pulsed-, controlled-, targeted and programmed release. Thus compounds of the invention may be formulated as a solid, semi-solid, or thixotropic liquid for administration as an implanted depot providing modified release of the active compound. Examples of such formulations include drug-coated stents and PLGA microspheres.

Nanoparticles also represent drug delivery systems suitable for most administration routes. Over the years, a variety of natural and synthetic polymers have been explored for the preparation of nanoparticles, of which Poly(lactic acid) (PLA), Poly(glycolic acid) (PGA), and their copolymers (PLGA) have been extensively investigated because of their biocompatibility and biodegradability. Nanoparticles and other nanocarriers act as potential carries for several classes of drugs such as anticancer agents, antihypertensive agents, immunomodulators, and hormones; and macromolecules such as nucleic acids, proteins, peptides, and antibodies. See, e.g., Crit. Rev. Ther. Drug Carrier Syst. 21:387-422, 2004; Nanomedicine: Nanotechnology, Biology and Medicine 1:22-30, 2005.

The compositions of the present invention may comprise, or be administered together with, one or more additional pharmaceutically active components such as adjuvants, lipids, interbilayer crosslinked multilamellar vesicles, biodegradable poly(D, L-lactic-co-glycolic acid) [PLGA]-based or poly anhydride-based nanoparticles or microparticles, and nanoporous particle-supported lipid bilayers such as liposomes, CTLA-4 and PD-1 pathway Antagonists, PD-1 pathway blocking agents, inactivated bacteria which induce innate immunity (e.g., inactivated or attenuated *Listeria* monocytogenes), compositions which mediate innate immune activation via Toll-like Receptors (TLRs), (NOD)-like receptors (NLRs), Retinoic acid inducible gene-based (RIG)-I-like receptors (RLRs), C-type lectin receptors (CLRs), pathogenassociated molecular patterns ("PAMPs"), chemotherapeutic agents, and the like.

The compounds and compositions of the present invention may be administered as a component of an antibody-drug conjugate or other targeted delivery modality.

Topical Administration

Compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubilizer. Most commonly used for these purposes are alpha-, beta- and gamma-cyclodextrins, examples of which may be found in PCT Publication Nos. WO 91/11172, WO 94/02518 and WO 98/55148, the disclosures of which are incorporated herein by reference in their entireties.

Dosage: The amount of the active compound administered will be dependent on the subject being treated, the severity of the disorder or condition, the rate of administration, the disposition of the compound and the discretion of the prescribing physician. One possible dosage is in the range of about 0.001 to about 100 mg per kg body weight, administered daily, every other day, every third day, every fourth day, every fifth day, every sixth day, weekly, every other week, monthly, or on other dosing schedules. In some instances, dosage levels below the lower limit of the aforesaid range may be more than adequate, while in other cases still larger doses may be used without causing any harmful side effect, with such larger doses typically divided into several smaller doses for administration throughout the day.

Kit-of-Parts: Inasmuch as it may desirable to administer a combination of active compounds, for example, for the purpose of treating a particular disease or condition, it is within the scope of the present invention that two or more pharmaceutical compositions, at least one of which contains a compound in accordance with the invention, may conveniently be combined in the form of a kit suitable for coadministration of the compositions. Thus the kit of the invention includes two or more separate pharmaceutical compositions, at least one of which contains a compound of the invention, and means for separately retaining said compositions, such as a container, divided bottle, or divided foil packet. An example of such a kit is the familiar blister pack used for the packaging of tablets, capsules and the like.

The kit of the invention is particularly suitable for administering different dosage forms, for example, oral and parenteral, for administering the separate compositions at different dosage intervals, or for titrating the separate compositions against one another. To assist compliance, the kit typically includes directions for administration and may be provided with a memory aid.

EXAMPLES

General Methods
Synthetic Experimental Procedures:

Experiments were generally carried out under inert atmosphere (nitrogen or argon), particularly in cases where oxygen- or moisture-sensitive reagents or intermediates were employed. Commercial solvents and reagents were generally used without further purification and dried over molecular sieves (generally Sure-Seal™ products from the Aldrich Chemical Company, Milwaukee, Wis.). Mass spectrometry data is reported from either liquid chromatography-mass spectrometry (LC-MS), atmospheric pressure chemical ionization (APCI), electrospray ionization (ESI) or liquid chromatography-Time of Flight (LC-TOF) methods. Chemical shifts for nuclear magnetic resonance (NMR) data are expressed in parts per million (ppm) referenced to residual peaks from the deuterated solvents employed.

For syntheses referencing procedures in other Examples or Methods, reaction Protocol (length of reaction and temperature) may vary. In general, reactions were followed by thin layer chromatography, LC-MS or HPLC, and subjected to work-up when appropriate. Purifications may vary between experiments: in general, solvents and the solvent ratios used for eluents/gradients were chosen to provide appropriate retention times. Unless otherwise specified, reverse phase HPLC fractions were concentrated via lyophilization/freeze-drying. Intermediate and final compounds were stored at (0° C.) or room temperature in closed vials or flasks under nitrogen. Compound names were generated with Chemdraw or ACD Labs software.

Abbreviations for solvents and/or reagents are based on American Chemical Society guidelines and are highlighted below:
Ac=Acetyl; Boc=N-tert-butoxycarbonyl; BTT=Benzylthiotetrazole; CDI=N,N'-Carbonyldiimidazole; DCA=Dichloroacetic acid; DCC=1,3-Dicyclohexylcarbodiimide; DCE=Dichloroethane; DCM=Dichloromethane; DDTT=(E)-N,N-Dimethyl-N'-(3-sulfanylidene-3H-1,2,4-dithiazol-5-yl)methanimidamide; DEA=N,N-Diethylamine; DIBAL-H=Diisobutylaluminium hydride; DIPEA=N,N-Diisopropylethylamine; DMA=Dimethylacetamide; DMAP=4-Dimethylaminopyridine;
DME=Dimethoxyethane; DMF=N,N-Dimethylformamide; DMOCP=2-chloro-5,5-dimethyl-1,3,2-dioxaphosphinane 2-oxide; DMSO=Dimethyl sulfoxide; DMT=Dimethoxytrityl; DMTCl=Dimethoxytrityl chloride; DPPA=Diphenylphosphoryl azide; EDCI=1-Ethyl-3-(3-dimethylaminopropyl)carbodiimide; EtOAc=Ethyl acetate; ETT=Ethylthiotetrazole;
Fmoc=Fluorenylmethyloxycarbonyl; h=hour; HATU=o-(7-azabenzotriazol-1-yl)-N,N,N',N'-te-trametyluronium hexafluorophosphate; HBTU=N,N,N',N'-Tetramethyl-O-(1H-benzotriazol-1-yl)uronium hexafluorophosphate; HOAc=Acetic acid; HOAt=1-Hydroxy-7-azabenzotriazole; HOBt=1-Hydroxybenzotriazole hydrate; LDA=Lithium diisopropylamide; Me=Methyl; MTBE=Methyl tert-butyl ether; n-BuLi=n-Butyllithium; NBS=N-Bromosuccinimide; NMM=N-methyl morpholine; NMO=N-methyl morpholine N-oxide; Ph=Phenyl; PivCl=Pivaloyl chloride; PPTS=Pyridinium p-Toluenesulfonate; p-TsOH=p-Toluenesulfonic acid; rt=room temperature; TEAB=Tetraethylammonium Bromide; TBAI=Tetrabutylammonium Iodide; TBS=tert-Butyldimethylsilyl; TBSCl=tert-Butyldimethylsilyl Chloride; TEA=Triethylamine; Tf=Trifluoromethanesulfonate;

TFA=Trifluoroacetic acid; THF=Tetrahydrofuran; and TPTU=O-(2-Oxo-1(2H)pyridyl)-N,N,N,'N'-tetramethyluronium tetrafluoroborate.

General Scheme

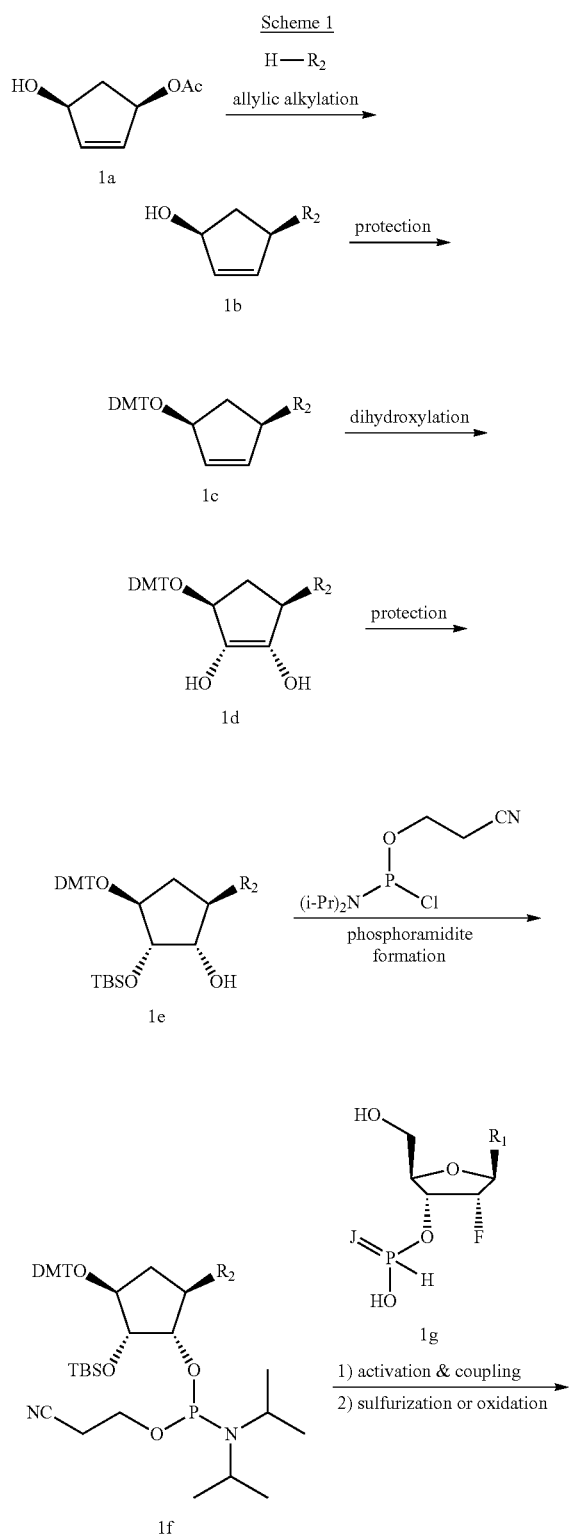

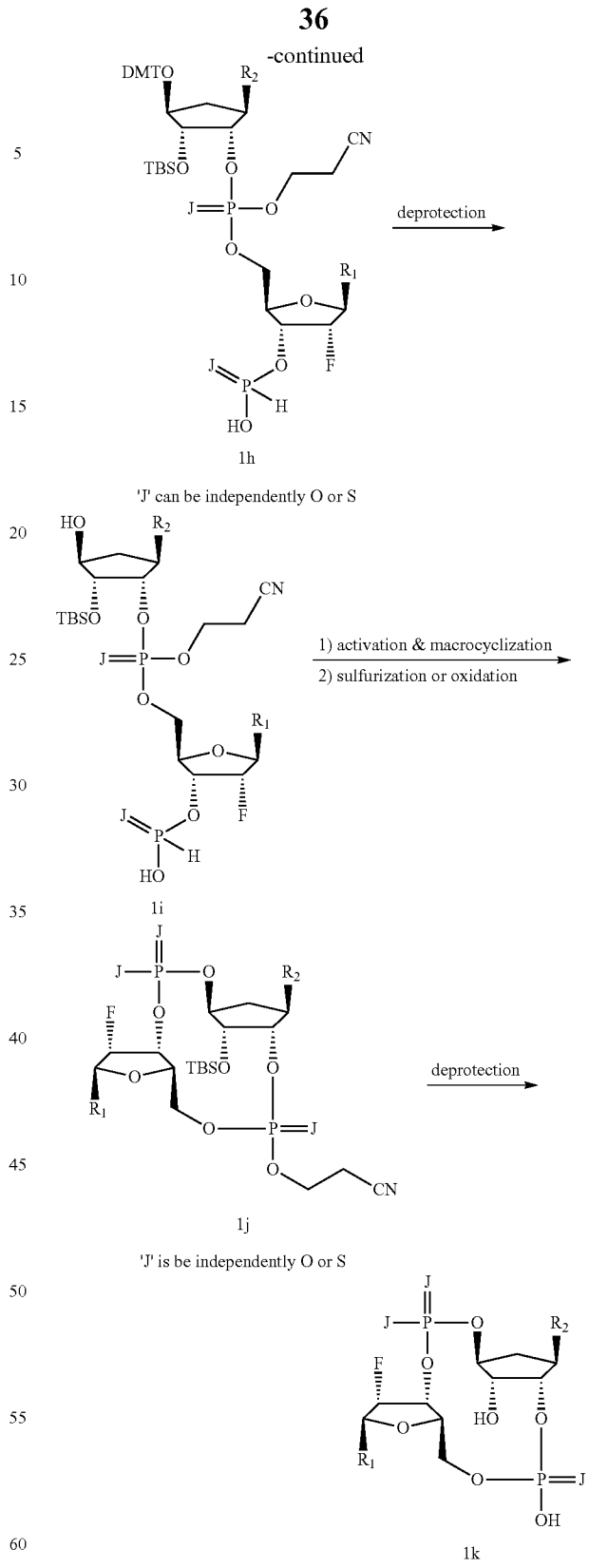

In general, the synthesis of the cyclopentane-based STING activators can be analogized to the routes used to make the appropriate macrocycles found in the synthesis of cyclic dinucleotides (Gaffney B. L., et. al.; *Organic Letters* 2010 12(14) 3269-3271).

As exemplified in Scheme 1, the chiral allylic acetate 1a can be purchased or synthesized (Deardorff D., et. al.; Tetrahedron Letters 1986 27(11) 1255-1256). An allylic alkylation can be performed with a nitrogen contain heterocycle or nucleobase to form compounds such as 1b (Trost, B., et. al.; *Angew. Chem. Int. Ed.* 1996, 35 1569-1572). These reactions are typically run using a palladium catalyst, a phosphine ligand and basic condition. Other metal catalyst and ligand combination can also be employed to achieve the same transformation. Typically, protection of the allylic alcohol, 1b, with a dimethoxytrityl (DMT) group is achieved using dimethoxytrityl chloride (DMTCl) and a base to give compounds such as 1c. The double bond of 1c is typically dihydroxylated with catalytic osmium tetroxide and N-methylpiperidine N-oxide to give compounds such as 1d. Other dihydroxylating reagents such as permanganate or ruthenium tetroxide may be used to do the same transformation. Typically, mono-protection of the compounds such as 1d can be achieved using tetrabutyldimethylsilyl choride (TBSCl) with tetrazole or tetrabutyldimethylsilyl trifluoromethanesulfonate (TBSOTf) and base to give compounds such as 1e. Phosphoramidites such as compound 1f are typically made from compounds such as 1e when treated with 3-((chloro(diisopropylamino)phosphanyl)oxy)propanenitrile and base. H-phosphonates and thio-H-phosphonates such as compound 1g are generally made from the appropriately protected nucleoside and a mixed anhydride of phosphonic acid followed by sulfurization if necessary. The protecting group is removed to reveal the primary alcohol 1g. Coupling of compounds such as 1g and 1f generally occur after phosphoramidites such as 1f are treated with acidic activators. The resulting coupled material is then sulfurized with sulfurizing agents such as DDTT, 3H-benzodithiol-3-one or similar reagent to produce thiophosphonates such as 1h. Otherwise the coupled material can be oxidized with reagents such as t-butyl peroxide or similar oxidants to produce phosphates such as 1h. Compounds such as 1h can be treated with mild acid such as dichloroacetic acid to reveal compounds such as 1i. H-phosphonate compounds such as 1i can be activated with reagents such as DMOCP to affect macrocyclization which then can be sulfurized by reagents such as 3H-benzodithiol-3-one to generate cyclic thiophosphonates such as 1j or oxidized with reagents such as t-butylperoxide to generate cyclic phosphates such as 1j. After the appropriate deprotection conditions, cyclic dithiophosphonates, diphosphates or mixed thiophosphonate-phosphate compounds such as 1k can be generated. Compounds at every step may be purified by standard techniques such as column chromatography, crystallization, reverse phase HPLC or SFC. If necessary, separation of the diastereomers of 1k may be carried out under standard methods known in the art such as chiral SFC or HPLC to afford single diastereomers. Note that "A" denotes carbon (also bound to hydrogen or a substituent) or nitrogen.

Example 1

Synthesis of (4S,6R,7S,11aR,13R,14R,14aR,15R)-6,13-bis(6-amino-9H-purin-9-yl)-14-fluoro-2,9-disulfanyloctahydro-11H-4,7-methanofuro[3,2-d][1,3,7,9,2,8]tetraoxadiphosphacyclotridecin-15-ol 2,9-dioxide

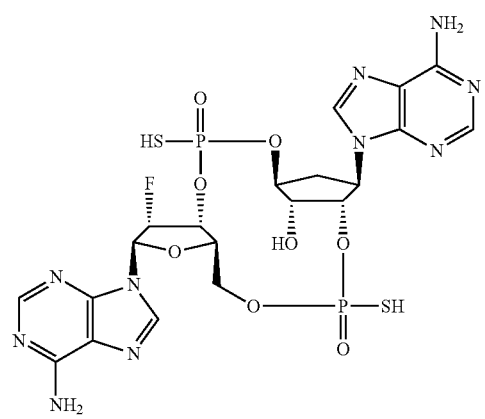 [SMILES: Nc1ncnc2c1ncn2[C@@H]1C[C@@H]2OP(=O)(S)O[C@H]3[C@@H](F)[C@H](n4cnc5c(N)ncnc54)O[C@@H]3COP(=O)(S)O[C@@H]1[C@@H]2O]

Scheme A

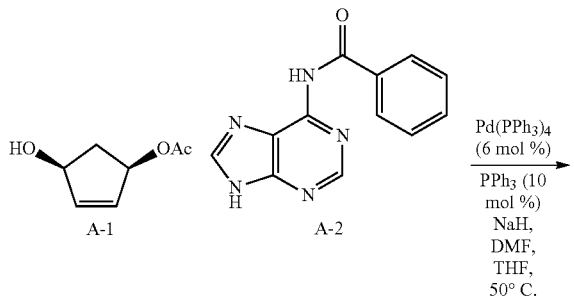

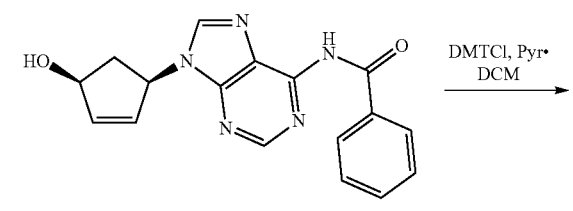

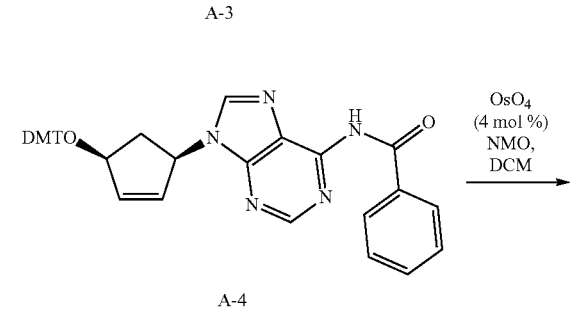

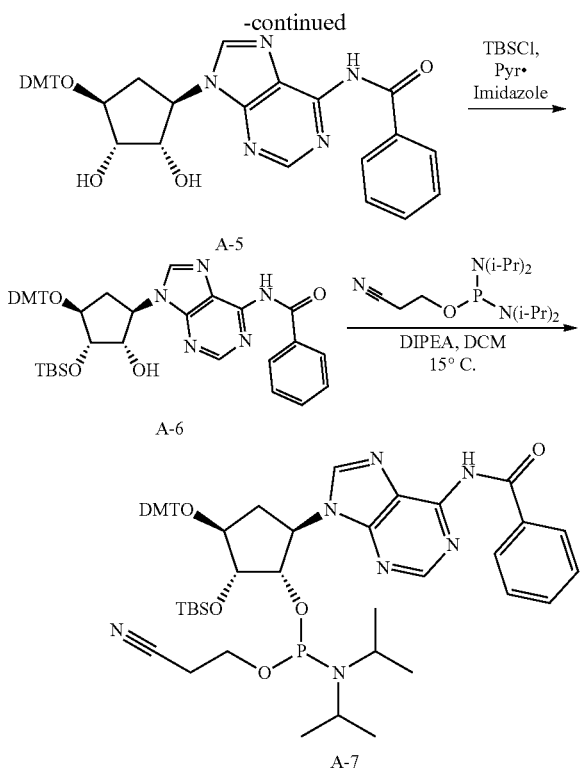

Step 1: Synthesis of N-(9-((1R,4S)-4-hydroxycyclopent-2-en-1-yl)-9H-purin-6-yl)benzamide (A-3)

To an oven dried round bottom flask (flask A), equipped with a magnetic stirbar and purged with N$_2$, was added A-1 (8330 mg, 34.8 mmol) and DMF (50 mL). To the solution was added NaH (60 wt % dispersion in mineral oil, 1530 mg, 38.3 mmol) under N$_2$. To a second round bottom flask (flask B), equipped with a magnetic stirbar and purged with N$_2$, was added A-2 (4950 mg, 34.8 mmol), Pd(PPh$_3$)$_4$ (2490 mg, 2.16 mmol), PPh$_3$ (913 mg, 3.48 mmol), and THF (50 mL). After 30 min, the solution in flask A was transferred to flask B. Flask B was then placed in an oil bath and heated at 50° C. under N$_2$ for 12 hours. The reaction mixture was quenched with H$_2$O (100 mL) and transferred to a separatory funnel with EtOAc. The phases were separated and the aqueous phase was extracted with EtOAc (100 mL×2) and DCM/MeOH (5:1, 100 mL×5). The combined organic extracts were concentrated under vacuum. The crude residue thus obtained was purified via flash column chromatography (240 g SiO$_2$, Isco, 9% MeOH/DCM to afford A-3 (19.7 g, 88%) as a yellow solid. LCMS [M+H]=322 observed; $^1$H NMR (400 MHz, DMSO-d6) δ ppm=11.18 (s, 1H), 8.79-8.73 (m, 1H), 8.45-8.38 (m, 1H), 8.05 (br d, J=7.5 Hz, 2H), 7.73-7.51 (m, 4H), 6.30-6.20 (m, 1H), 6.07 (br d, J=5.4 Hz, 1H), 5.61 (br dd, J=3.9, 5.2 Hz, 1H), 5.38 (d, J=6.2 Hz, 1H), 4.81-4.72 (m, 1H), 3.02-2.91 (m, 1H), 1.79 (td, J=4.5, 13.8 Hz, 1H).

Step 2: Synthesis of N-(9-((1R,4S)-4-(bis(4-methoxyphenyl)(phenyl)methoxy)cyclopent-2-en-1-yl)-9H-purin-6-yl)benzamide (A-4)

To a round bottom flask, equipped with a magnetic stirbar, was added A-3 (19.7 g, 61.3 mmol) and anhydrous pyridine (50 mL). The solution was concentrated to dryness under vacuum and further dried under high vacuum for 1 h. The flask was purged with N$_2$ followed by the addition of anhydrous pyridine (150 mL) and DMTCl (23.9 g, 70.5 mmol). The reaction was stirred at 9° C. under N$_2$ for 12 hours. The reaction was quenched with H$_2$O and transferred to a separatory funnel with EtOAc. The phases were separated and the aqueous phase was extracted with EtOAc (200 mL×2). The organic extracts were washed with brine (100 mL×2), dried (Na$_2$SO$_4$), filtered, and concentrated under vacuum. The crude residue thus obtained was purified via flash column chromatography (240 g SiO$_2$, Isco, 100% EtOAc) to afford A-4 (29.2 g, 76%) as a yellow solid. LCMS [M+H]=624 observed; $^1$H NMR (400 MHz, CHLOROFORM-d) δ ppm=8.94 (br s, 1H), 8.79 (s, 1H), 8.26 (s, 1H), 8.03 (br d, J=7.5 Hz, 2H), 7.64-7.59 (m, 1H), 7.57-7.47 (m, 4H), 7.44-7.36 (m, 4H), 7.35-7.28 (m, 2H), 7.26-7.20 (m, 1H), 6.87-6.81 (m, 4H), 5.90 (dd, J=1.5, 5.5 Hz, 1H), 5.65 (td, J=1.8, 5.5 Hz, 1H), 5.56-5.48 (m, 1H), 4.78-4.71 (m, 1H), 3.80 (d, J=1.0 Hz, 6H), 2.58-2.47 (m, 1H), 1.56 (td, J=3.6, 14.7 Hz, 1H).

Step 3: Synthesis of N-(9-((1R,2S,3S,4S)-4-(bis(4-methoxyphenyl)(phenyl)methoxy)-2,3-dihydroxycyclopentyl)-9H-purin-6-yl)benzamide (A-5)

To round bottom flask, equipped with a magnetic stirbar, was added A-4 (29.2 g, 46.8 mmol), DCM (300 mL), and H$_2$O (18 mL). To the yellow solution was added NMO (16.5 g, 140 mmol) and OsO$_4$ (4% in t-BuOH, 20.8 g, 3.28 mmol). The reaction was stirred at 16° C. for 5 hours. The reaction was then transferred to a separatory funnel with DCM (50 mL) and quenched with saturated Na$_2$SO$_3$ (100 mL). The phases were separated and the organic phase was washed with brine (100 mL), dried (Na$_2$SO$_4$), filtered, and concentrated under vacuum. The crude residue thus obtained was purified via flash column chromatography (120 g SiO$_2$, Isco, 3% MeOH/DCM to 5% MeOH/DCM) to afford A-5 (24.9 g, 80%) as a yellow solid. LCMS [M+H]=658 observed; $^1$H NMR (400 MHz, CHLOROFORM-d) δ ppm=9.09 (br s, 1H), 8.78-8.59 (m, 1H), 8.02 (br d, J=7.3 Hz, 2H), 7.93-7.85 (m, 1H), 7.60 (br dd, J=4.8, 6.3 Hz, 1H), 7.56-7.39 (m, 5H), 7.39-7.27 (m, 6H), 7.25-7.19 (m, 1H), 6.84 (br d, J=8.8 Hz, 4H), 5.69 (br s, 1H), 4.65 (br d, J=7.0 Hz, 2H), 4.16 (br d, J=1.3 Hz, 1H), 3.92 (br s, 1H), 3.78 (d, J=2.0 Hz, 6H), 3.72 (t, J=4.5 Hz, 2H), 2.95 (br s, 1H), 2.45-2.33 (m, 2H), 1.94-1.75 (m, 1H).

Step 4: Synthesis of N-(9-((1R,2S,3S,4S)-4-(bis(4-methoxyphenyl)(phenyl)methoxy)-3-((tert-butyldimethylsilyl)oxy)-2-hydroxycyclopentyl)-9H-purin-6-yl)benzamide (A-6)

To an oven dried round bottom flask, equipped with a magnetic stirbar and cooled under N$_2$, was added A-5 (4.12 g, 6.264 mmol), DCM (200 mL), Et$_3$N (3170 mg, 31.3 mmol) and TBSOTf (2.49 mg, 9.4 mmol) at 0° C. dropwise. The ice bath was removed and the reaction was stirred under N$_2$ at 20° C. for 12 hours. At this stage, starting material was still detected by LCMS and an additional aliquot of TBSOTf (2485 mg, 9.4 mmol) was added to the mixture at 0° C. dropwise. The ice bath was removed and the reaction mixture was stirred under N$_2$ at 20° C. for 12 hours. The reaction was quenched with MeOH (15 mL). The solution was transferred to a separatory funnel with DCM and further diluted with H$_2$O. The phases were separated and the organic phase was washed with 1 portion H$_2$O, 1 portion brine, dried ($Na_2SO_4$), filtered, and concentrated under vacuum. The crude residue was purified via flash column chromatography (40 g $SiO_2$, Isco, 40% EtOAc/Pet. Ether to 50% EtOAc/Pet. Ether) to afford A-6 (1.29 g, 26%) as a white solid. LCMS [M+H]=772 observed; $^1$H NMR (400 MHz, CHLOROFORM-d) δ ppm=8.95 (s, 1H), 8.78 (s, 1H), 8.09 (s, 1H), 8.05-7.98 (m, 2H), 7.64-7.57 (m, 1H), 7.56-7.47 (m, 3H), 7.56-7.47 (m, 1H), 7.44-7.34 (m, 4H), 7.33-7.28 (m, 2H), 7.26-7.19 (m, 1H), 6.88-6.79 (m, 4H), 4.76 (dd, J=5.6, 11.7 Hz, 1H), 4.70-4.62 (m, 1H), 4.38 (br s, 1H), 4.10-4.06 (m, 1H), 3.78 (d, J=1.3 Hz, 6H), 2.98 (d, J=8.8 Hz, 1H), 2.17 (s, 1H), 0.99 (br dd, J=4.6, 15.2 Hz, 1H), 0.93-0.85 (m, 9H), 0.14 (s, 3H), 0.03 (s, 3H).

Step 5: Synthesis of (1S,2R,3S,5R)-5-(6-benzamido-9H-purin-9-yl)-3-(bis(4-methoxyphenyl)(phenyl)methoxy)-2-((tert-butyldimethylsilyl)oxy)cyclopentyl (2-cyanoethyl) diisopropylphosphoramidite (A-7)

To an oven dried round bottom flask, equipped with a magnetic stibar and purged with $N_2$, was added A-6 (8.80 g, 11.4 mmol), DIPEA (14.7 g, 114 mmol), and anhydrous DCM (320 mL). To the solution was added 3-((chloro(diisopropylamino)phosphanyl)oxy)propanenitrile (13.5 g, 57.0 mmol) at 15° C. under $N_2$. The reaction was stirred at 15° C. for 4 hours. The reaction was quenched with sat. $NaHCO_3$ (120 mL) and transferred to a separatory funnel with DCM (50 mL). The phases were separated and the organic phase was washed with brine (100 mL), dried ($Na_2SO_4$), and concentrated under vacuum. The crude residue thus obtained was purified via flash column chromatography (120 g $SiO_2$, Isco, 40% EtOAc/Pet. Ether to 60% EtOAc/Pet. Ether) twice to afford A-7 (8.57 g, 77%) as a light yellow solid. LCMS [M+H]=972 observed; $^1$H NMR (400 MHz, CHLOROFORM-d) δ ppm=8.91 (d, J=11.3 Hz, 1H), 8.79 (d, J=4.0 Hz, 1H), 8.22-8.13 (m, 1H), 8.08-7.98 (m, 2H), 7.65-7.58 (m, 1H), 7.52 (q, J=7.2 Hz, 4H), 7.44-7.35 (m, 4H), 7.31 (dt, J=1.4, 7.5 Hz, 2H), 7.25-7.21 (m, 1H), 6.84 (td, J=2.0, 9.0 Hz, 4H), 5.15-5.00 (m, 1H), 4.99-4.79 (m, 1H), 4.31-3.98 (m, 2H), 3.78 (s, 6H), 3.76-3.57 (m, 2H), 3.50-3.34 (m, 2H), 2.60 (t, J=6.3 Hz, 1H), 2.52-2.25 (m, 2H), 1.33-1.14 (m, 1H), 1.11 (d, J=6.8 Hz, 3H), 1.02 (t, J=7.4 Hz, 6H), 0.85 (s, 9H), 0.79 (d, J=6.8 Hz, 3H), 0.11 (d, J=11.8 Hz, 3H), −0.06 (d, J=0.8 Hz, 3H); $^{31}$P NMR (162 MHz, CHLOROFORM-d) δ ppm=149.67 (s, 1P), 147.94 (s, 1P).

Scheme B

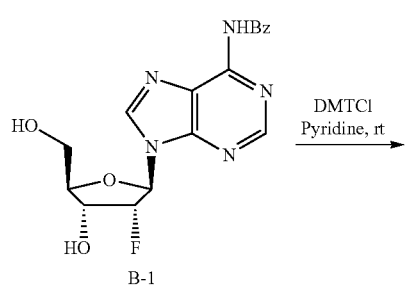

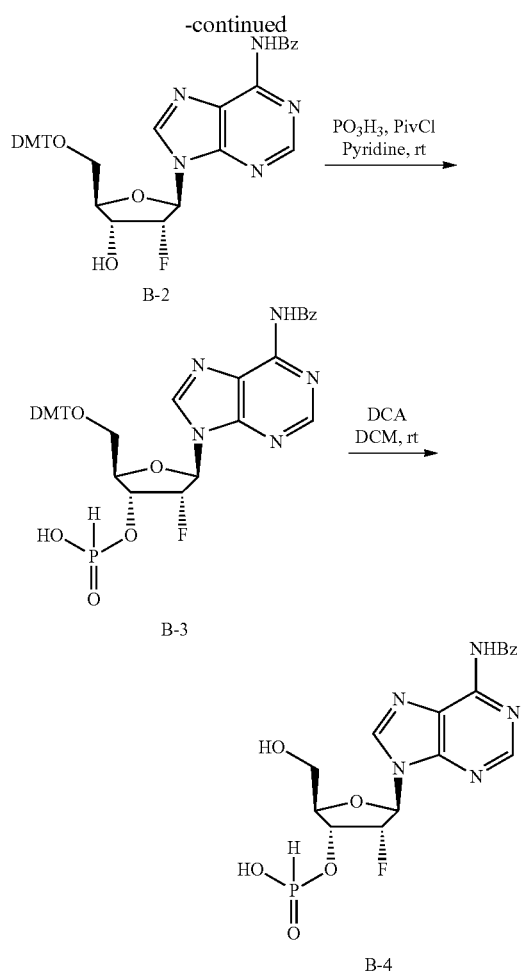

Step 1: Synthesis of N-(9-((2R,3R,4R,5R)-5-((bis(4-methoxyphenyl)(phenyl)methoxy)methyl)-3-fluoro-4-hydroxytetrahydrofuran-2-yl)-9H-purin-6-yl)benzamide (B-2)

To a round bottom flask, equipped with a magnetic stirbar, was added commercially available N-(9-((2R,3R,4R,5R)-3-fluoro-4-hydroxy-5-(hydroxymethyl)tetrahydrofuran-2-yl)-9H-purin-6-yl)benzamide B-1 (42.00 g, 37.50 mmol) and co-evaporated with anhydrous pyridine three times. The residue was re-dissolved in pyridine (70 mL) followed by the addition of DMTCl (13.98 g, 41.25 mmol) at 0° C. The mixture was stirred at 25° C. for 12 h. The reaction mixture was concentrated under reduced pressure. The residue was diluted with DCM (200 mL) and washed with three (200 mL) portions of saturated aqueous $NaHCO_3$. The organic layer was dried over $Na_2SO_4$ (25.00 g), filtered and concentrated under reduced pressure. The crude residue was purified by flash column chromatography ($SiO_2$, 85% Pet. ether/EtOAc to 100% EtOAc) to afford B-2 (68.7 g, 85%) as a white solid which was used in the next step without further purification. LCMS [M+H]=676 observed.

Step 2: Synthesis of (2R,3R,4R,5R)-5-(6-benzamido-9H-purin-9-yl)-2-((bis(4-methoxyphenyl)(phenyl)methoxy)methyl)-4-fluorotetrahydrofuran-3-yl hydrogen phosphonate (B-3)

Note: Six reactions were carried out in parallel. To a round bottom flask, equipped with a magnetic stirbar, was added phosphonic acid (21.8 g, 266 mmol) and co-evaporated with anhydrous pyridine (60 mL) three times. The residue was dissolved in anhydrous pyridine (180 mL) with mild heating (30° C.). To the solution was added B-2 (12.0 g, 17.8 mmol) at 30° C. after which the solution thus obtained was cooled to 0° C. To this mixture was added 2,2-dimethylpropanoyl chloride (21.4 g, 177 mmol) dropwise at 0° C. The mixture was warmed to 30° C. and stirred for 12 h. The six reactions were combined. The reaction mixture was quenched with 1M TEAB (1200 mL) and transferred to a separatory funnel. The solution was extracted with three (1000 mL) portions EtOAc. The combined organic extracts were washed with 0.5M TEAB (500 mL), brine (500 mL), dried over Na$_2$SO$_4$ (35.0 g), filtered and concentrated under vacuum. The crude residue was purified by flash column chromatography (SiO$_2$, 2% MeOH/DCM to 5% MeOH/DCM, 1% TEA) to remove major impurities and afford B-3 (100.0 g, crude) as a white solid which was used in the next step without further purification. LCMS [M−H]=738 observed.

Step 3: Synthesis of (2R,3R,4R,5R)-5-(6-benzamido-9H-purin-9-yl)-4-fluoro-2-(hydroxymethyl)tetrahydrofuran-3-yl hydrogen phosphonate (B-4)

Note: Five reactions were carried out in parallel. To a round bottom flask, equipped with a magnetic stir bar, was added B-3 (20.0 g, 27.0 mmol) and a solution of DCA (17.4 g, 135 mmol) in DCM (200 mL) and was added. The mixture was stirred at 25° C. for 0.5 h. The five reactions were combined. The solid product in reaction mixture was filtered and triturated with DCM (300 mL) to afford B-4 (40.0 g, 63%) as a white solid. LCMS [M+H]=438 observed; $^1$H NMR (400 MHz, DMSO-d6) δ ppm=11.95-10.65 (m, 1H), 8.78 (s, 1H), 8.73 (s, 1H), 8.05 (d, J=7.3 Hz, 2H), 7.71-7.61 (m, 1H), 7.61-7.49 (m, 2H), 6.69 (s, 1H), 6.46 (dd, J=3.1, 16.6 Hz, 1H), 5.82 (td, J=3.4, 51.7 Hz, 1H), 5.30-5.16 (m, 1H), 4.31-4.20 (m, 1H), 3.80 (dd, J=2.8, 12.2 Hz, 1H), 3.67 (dd, J=3.7, 12.5 Hz, 1H); $^{19}$F NMR (377 MHz, DMSO-d6) δ ppm=−203.02 (s, 1F); $^{31}$P NMR (162 MHz, DMSO-d6) δ ppm=4.20 (s, 1P).

Scheme C

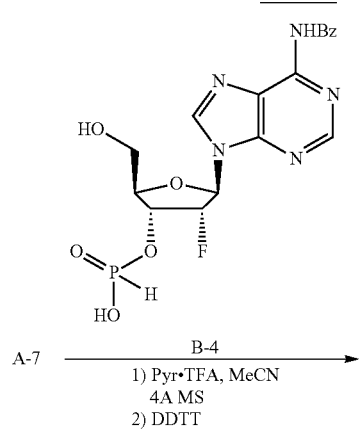

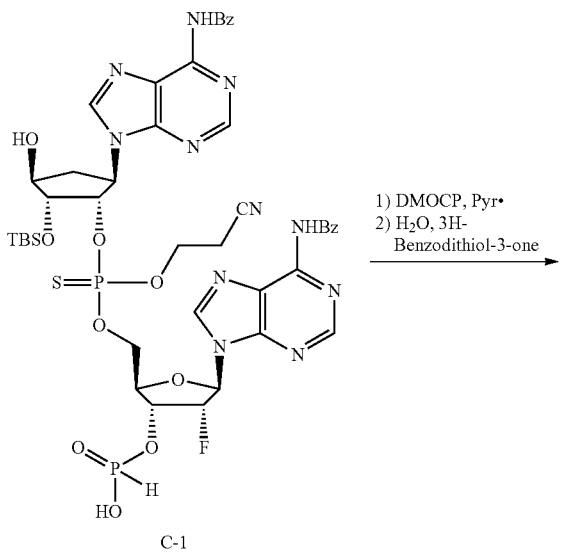

C-1

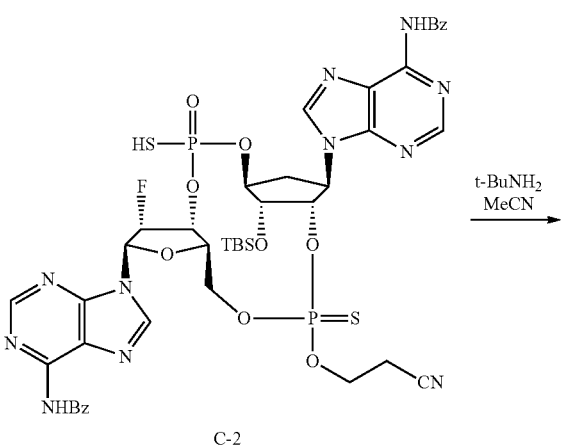

C-2

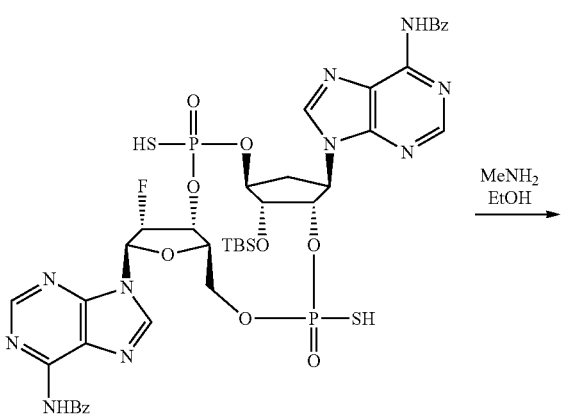

C-3

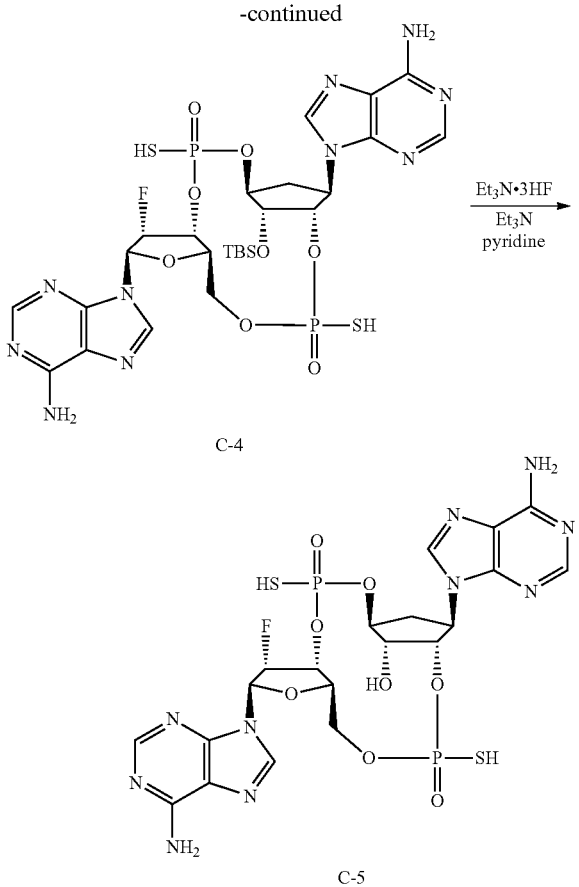

C-4

C-5

Step 1: Synthesis of (2R,3R,4R,5R)-5-(6-benzamido-9H-purin-9-yl)-2-((((((1S,2R,3S,5R)-5-(6-benzamido-9H-purin-9-yl)-2-((tert-butyldimethylsilyl)oxy)-3-hydroxycyclopentyl)oxy)(2-cyanoethoxy) phosphorothioyl)oxy)methyl)-4-fluorotetrahydrofuran-3-yl hydrogen phosphonate (C-1)

To a round bottom flask, equipped with a magnetic stirbar, was added the H-phosphonate B-4 (1.0 g, 2.29 mmol) and pyridinium trifluoroacetate (1.77 g, 9.15 mmol). The solids were taken up in anhydrous MeCN (10 mL×2) and concentrated under vacuum. The residue was re-dissolved in anhydrous MeCN (30 mL) and 3A molecular sieves (4.0 g) were added. The solution was stirred for 30 minutes at which point phosphoramidite A-7 (2.67 g, 2.74 mmol) was added. The reaction was stirred at rt for 1.5 hours during which a homogeneous solution was obtained. To the reaction was added DDTT (493 mg, 2.40 mmol) and the reaction was allowed to stir at rt overnight. The reaction was filtered and the solids washed with MeOH/DCM (1:1). The filtrate was concentrated under vacuum followed by trituration with n-hexane/TBME (1:1). The crude residue thus obtained was purified via preparatory high performance liquid chromatography (Phenomenex Synergi Max-RP 150×50 mm×10 µm, 20% MeCN/H$_2$O with 10 mM NH$_4$HCO$_3$ to 50% MeCN/H$_2$O with 10 mM NH$_4$HCO$_3$, 120 mL/min) to afford C-1 (390 mg, 13%) as a white solid. LCMS [M+H]=1038 observed; $^{31}$P NMR (162 MHz, METHANOL-d4) δ ppm=68.24 (s, 1P), 67.74 (s, 1P), 2.95 (s, 1P), 2.71 (s, 1P).

Step 2: Synthesis of N,N'-{[(4S,6R,7S,11aR,13R,14R,14aR,15R)-15-{[tert-butyl(dimethyl)silyl]oxy}-9-(2-cyanoethoxy)-4-fluoro-2-oxido-2-sulfanyl-9-sulfidooctahydro-11H-4,7-methanofuro[3,2-d][1,3,7,9,2,8]tetraoxadiphosphacyclotridecine-6,13-diyl]bis(9H-purine-9,6-diyl)}dibenzamide (C-2)

To an oven dried round bottom flask, equipped with a magnetic stirbar and cooled under N$_2$, was added C-1 (320 mg, 0.308 mmol) and anhydrous pyridine (10 mL). To the solution was added DMOCP (1.02 g, 5.55 mmol) at rt under N$_2$. The reaction was stirred under N$_2$ for 1 hour at which point the starting material had been consumed. To the reaction was added H$_2$O (333 mg, 18.5 mmol) and 3H-1,2-benzodithiol-3-one (130 mg, 0.770 mmol) at rt under N$_2$. The reaction was stirred under N$_2$ at rt for 30 minutes. The reaction was quenched with sat. NaHCO$_3$ and transferred to a separatory funnel with EtOAc. The phases were separated and the aqueous phase was extracted with 2 portions EtOAc (60 mL). The combined organic extracts were washed with brine, dried (Na$_2$SO$_4$), filtered and concentrated under vacuum. The crude residue was purified via flash column chromatography (SiO$_2$, Isco, 9% MeOH/DCM to 11% MeOH/DCM). The material obtained was further purified via preparatory thin layer chromatography (SiO$_2$, 11% MeOH/DCM) to afford C-2 (135 mg, 41%) as a white solid. LCMS [M+H]=1052 observed; $^{31}$P NMR (162 MHz, METHANOL-d4) δ ppm=68.90 (s, 1P), 68.33 (s, 1P), 64.75 (s, 1P), 64.68 (s, 1P), 55.42 (s, 1P), 53.26 (s, 1P), 52.98 (s, 1P).

Step 3: Synthesis of N,N'-{[(4S,6R,7S,11aR,13R,14R,14aR,15R)-15-{[tert-butyl(dimethyl)silyl]oxy}-14-fluoro-2,9-dioxido-2,9-disulfanyloctahydro-11H-4,7-methanofuro[3,2-d][1,3,7,9,2,8]tetraoxadiphosphacyclotridecine-6,13-diyl]bis(9H-purine-9,6-diyl)}dibenzamide (C-3)

To a flask containing C-2 (130 mg, 0.124 mmol) was added acetonitrile (9 mL). To the resulting suspension was added 4.5 mL tert-butylamine. The reaction mixture became a solution and was stirred at room temperature for 20 min. The reaction was concentrated to give crude C-3 as white solid, used for next step.

LCMS [M+H]=999.21

$^{31}$P NMR (162 MHz, METHANOL-d4) δ ppm 57.61 (s, 1P) 57.20 (s, 1P) 55.15 (s, 1P) 54.77 (s, 1P) 54.00 (s, 1P) 53.94 (s, 1P) 52.30 (s, 1P) 52.04 (s, 1P)

Step 4: Synthesis of 9,9'-[(4S,6R,7S,11aR,13R,14R,14aR,15R)-15-{[tert-butyl(dimethyl)silyl]oxy}-14-fluoro-2,9-dioxido-2,9-disulfanyloctahydro-11H-4,7-methanofuro[3,2-d][1,3,7,9,2,8]tetraoxadiphosphacyclotridecine-6,13-diyl]bis(9H-purin-6-amine) (C-4)

The crude material C-3 (123 mg, 0.123 mmol) was added to 6 mL of 33% methylamine in EtOH (0.02 M). The solution stirred at room temperature overnight. The reaction mixture was concentrated to give crude C-4 that was used for the next step.

LCMS [M+H]=791.15

$^{31}$P NMR (162 MHz, METHANOL-d4) δ ppm 58.63 (br. s., 1P) 55.08 (br. s., 1P) 54.57 (br. s., 1P) 52.50 (s, 1P) 52.26 (s, 1P)

<sup>19</sup>F NMR (376 MHz, METHANOL-d4) δ ppm −200.04 (s, 1F) −200.59 (s, 1F) −201.31 (br. s., 1F)

Step 5: Synthesis of (4S,6R,7S,11aR,13R,14R, 14aR,15R)-6,13-bis(6-amino-9H-purin-9-yl)-14-fluoro-2,9-disulfanyloctahydro-11H-4,7-methanofuro[3,2-d][1,3,7,9,2,8] tetraoxadiphosphacyclotridecin-15-ol 2,9-dioxide (C-5)

The material C-4 (97.4 mg, 0.123 mmol) was co-evaporated with 4 mL pyridine/Et₃N (v/v, 3/1) three times. The material was dissolved in 1.13 mL pyridine (0.1 M), charged with N₂, triethylamine (0.102 mL, c=0.1 M) and triethylamine trihydrofluoride (993 mg, 6.16 mmol) were added. The resulting reaction mixture was heated at 50° C. for overnight. The reaction mixture was quenched with NaHCO₃ solution to pH 6. The volatile components were removed in vacuo. The residue was purified by reverse phase prep-HPLC (Phenomenex Gemini C18 21.2×150 mm 5 u column) eluted with 10-40% MeCN in aq. NH₄HCO₃ (10 mM) to give two diastereomeric compounds as white solid, and a mixture of the other diastereomers. The other two diastereomers were separated on Phenomenex Luna Omega 5 u Polar C18 21.2×150 mm column eluted with 8-40% MeCN in aq. NH₄HCO₃ (10 mM).

Peak 1, 13.76 mg, 15.8%;
LCMS [M+H]=677.00
<sup>1</sup>H NMR (400 MHz, DEUTERIUM OXIDE) δ ppm 8.42 (s, 1H) 8.34 (s, 1H) 8.30 (s, 1H) 7.90 (s, 1H) 6.49 (d, J=16.51 Hz, 1H) 6.27 (dd, J=49.34, 4.28 Hz, 1H) 5.36-5.46 (m, 1H) 5.10-5.24 (m, 2H) 4.65-4.69 (m, 1H) 4.62 (br. s., 1H) 4.54 (d, J=8.93 Hz, 1H) 4.34 (d, J=12.84 Hz, 1H) 4.15 (dd, J=12.29, 5.69 Hz, 1H) 2.99-3.11 (m, 1H) 2.28 (dd, J=15.96, 6.05 Hz, 1H)
<sup>31</sup>P NMR (162 MHz, DEUTERIUM OXIDE) δ ppm 56.18 (br. s., 1P) 50.55 (s, 1P)
<sup>19</sup>F NMR (376 MHz, DEUTERIUM OXIDE) δ ppm −200.13 (s, 1F)

Peak 2, 9.97 mg, 9%;
LCMS [M+H]=677.00
<sup>1</sup>H NMR (400 MHz, DEUTERIUM OXIDE) δ ppm 8.39 (s, 1H) 8.27 (s, 1H) 8.27 (s, 1H) 7.85 (s, 1H) 6.47 (d, J=16.63 Hz, 1H) 6.27 (dd, J=50.25, 3.79 Hz, 1H) 5.32-5.42 (m, 1H) 5.11-5.27 (m, 2H) 5.74 (m, 1H) 4.68-4.73 (m, 1H) 4.60 (br. s., 1H) 4.51 (d, J=9.05 Hz, 1H) 4.31 (d, J=11.98 Hz, 1H) 4.07-4.15 (m, 1H) 3.02-3.11 (m, 1H) 2.31 (dd, J=15.96, 6.42 Hz, 1H)
<sup>31</sup>P NMR (162 MHz, DEUTERIUM OXIDE) δ ppm 57.60 (s, 1P) 53.47 (s, 1P)
<sup>19</sup>F NMR (376 MHz, DEUTERIUM OXIDE) δ ppm −199.70 (s, 1F)

Peak 3, 15.25 mg, 17.5%;
LCMS [M+H]=677.00
<sup>1</sup>H NMR (400 MHz, DEUTERIUM OXIDE) δ ppm 8.27 (s, 1H) 8.26 (s, 1H) 8.22 (s, 1H) 7.73 (s, 1H) 6.45 (d, J=16.75 Hz, 1H) 6.27 (dd, J=50.25, 3.79 Hz, 1H) 5.46-5.53 (m, 1H) 5.04-5.18 (m, 2H) 4.93-5.09 (m, 1H) 4.61-4.67 (m, 2H) 4.55 (d, J=9.66 Hz, 1H) 4.41 (d, J=12.23 Hz, 1H) 4.06-4.14 (m, 1H) 2.94-3.09 (m, 1H) 2.20 (dd, J=15.47, 6.30 Hz, 1H)
<sup>31</sup>P NMR (162 MHz, DEUTERIUM OXIDE) δ ppm 51.67 (br. s., 1P) 50.40 (s, 1P)
<sup>19</sup>F NMR (376 MHz, DEUTERIUM OXIDE) δ ppm −200.23 (s, 1F)

Peak 4, 5.73 mg, 6.6%;
LCMS (ES, m/z): 677.00 [M+H]
<sup>1</sup>H NMR (400 MHz, DEUTERIUM OXIDE) δ ppm 8.26 (s, 1H) 8.24 (s, 1H) 8.21 (s, 1H) 7.74 (s, 1H) 6.44 (d, J=17.24 Hz, 1H) 5.73 (m., 1H) 5.41-5.51 (m, 1H) 5.05-5.20 (m, 2H) 4.70 (m, 1H) 4.61 (br. s., 1H) 4.51 (d, J=8.19 Hz, 1H) 4.38 (d, J=11.86 Hz, 1H) 4.01-4.16 (m, 1H) 3.02 (m, 1H) 2.15-2.29 (m, 1H)
<sup>31</sup>P NMR (162 MHz, DEUTERIUM OXIDE) δ ppm 51.91 (s, 1P) 51.56 (s, 1P)
<sup>19</sup>F NMR (376 MHz, DEUTERIUM OXIDE) δ ppm −199.85 (s, 1F)

Example 2

9-[(4S,6R,7S,11aR,13R,14R,14aR,15R)-13-(6-amino-9H-purin-9-yl)-14-fluoro-15-hydroxy-2,9-dioxido-2,9-disulfanyloctahydro-11H-4,7-methanofuro[3,2-d][1,3,7,9,2,8] tetraoxadiphosphacyclotridecin-6-yl]-1-methyl-1,9-dihydro-6H-purin-6-one

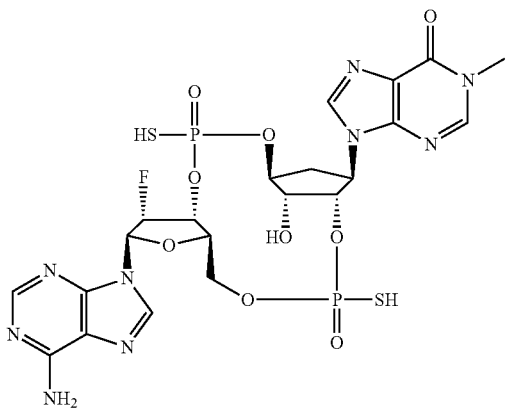 [SMILES: Cn1cnc2c(ncn2[C@@H]2C[C@@H]3OP(=O)(S)O[C@H]4[C@@H](F)[C@H](n5cnc6c(N)ncnc65)O[C@@H]4COP(=O)(S)O[C@@H]2[C@@H]3O)c1=O]

Scheme D

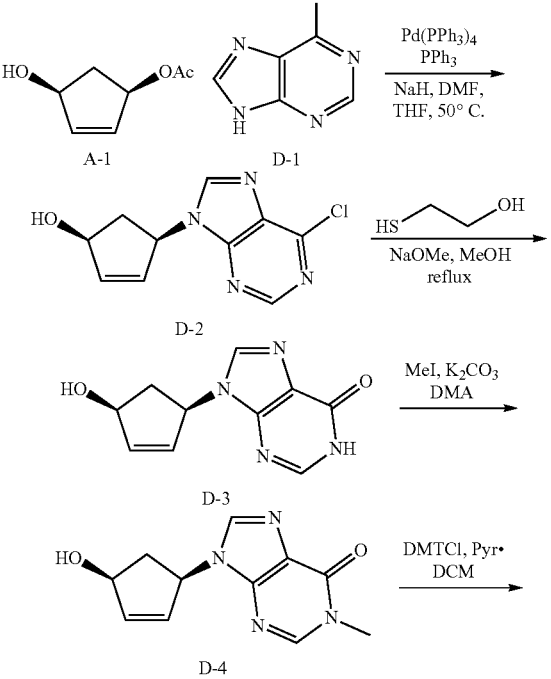

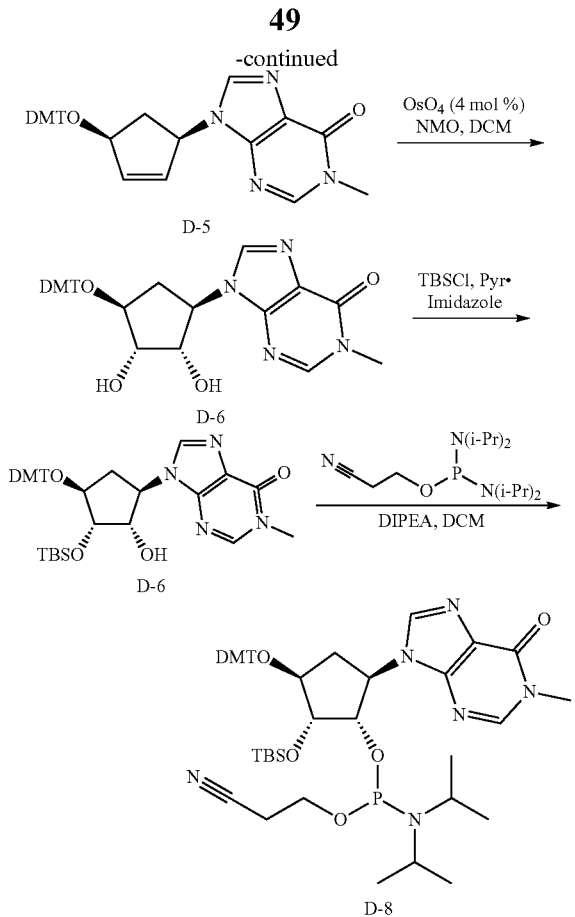

Step 1: Synthesis of (1S,4R)-4-(6-chloro-9H-purin-9-yl)cyclopent-2-en-1-ol (D-2)

A mixture of A-1 (1500 mg, 11 mmol), Pd(PPh$_3$)$_4$ (610 mg, 0.53 mmol), and PPh$_3$ (277 mg, 1.06 mmol), in THF (6 mL) was bubbled with N$_2$ for 15 min (flask A). In a separate flask (flask B), a suspension of D-1 in a mixture of THF (30 mL) and DMA (5 mL) was bubbled with N$_2$ for 15 min then NaH (60 wt % dispersion in mineral oil, 506 mg, 12.7 mmol) was added. After 1.5 hr, the contents of flask A were transferred to flask B (rinsed with 4 mL THF) and the reaction was heated at 50° C. overnight. The reaction mixture was concentrated; the residue was dissolved in EtOAc and washed with aq citric acid and brine. The combined aqueous phases were extracted with EtOAc (2x). The combined organic phases were dried over MgSO$_4$, filtered and concentrated. The crude residue was purified via flash chromatography (40 g SiO$_2$, Isco, 0-5% MeOH/DCM) to afford D-2 (1.45 g, 58%) as a foamy yellow solid. LCMS [M+H]=237 observed; $^1$H NMR (400 MHz, DMSO-d$_6$) δ ppm=8.79 (s, 1H) 8.60 (s, 1H) 6.24 (dt, J=5.53, 1.94 Hz, 1H) 6.00-6.11 (m, 1H) 5.60 (td, J=5.14, 1.96 Hz, 1H) 5.30 (d, J=6.24 Hz, 1H) 4.65-4.81 (m, 1H) 2.94 (ddd, J=14.00, 8.13, 7.34 Hz, 1H) 1.80 (dt, J=14.03, 4.48 Hz, 1H).

Step 2: Synthesis of 9-[(1R,4S)-4-hydroxycyclopent-2-en-1-yl]-1,9-dihydro-6H-purin-6-one (D-3)

To a solution of D-2 (1.45 g, 7.03 mmol) in MeOH (50 mL) was added mercaptoethanol (1.97 mL, 28.1 mmol) followed by sodium methoxide (1.52 g, 28.1 mmol). After refluxing for 8 hrs, the heat was turned off and the reaction was left standing overnight. The reaction was concentrated and used directly in the next step. LCMS [M+H]=219 observed.

Step 3: Synthesis of 9-[(1R,4S)-4-hydroxycyclopent-2-en-1-yl]-1-methyl-1,9-dihydro-6H-purin-6-one (D-4)

To a solution of D-3 (used crude from previous step) in DMF (47 mL) was added K$_2$CO$_3$ (3.39 g, 24.5 mmol) followed by methyl iodide (0.655 mL, 10.5 mmol). After stirring overnight, another 2 eq methyl iodide (0.873 mL, 14.0 mmol) was added. After 1 hr, the reaction was concentrated. The residue was slurried in DCM and filtered to remove solids. The mother liquor was concentrated and purified via flash chromatography (40 g SiO$_2$, Isco, 0-10% 7N NH$_3$ in MeOH/DCM) to afford D-4 (1.17 g, 72%) as a white solid. LCMS [M+H]=233 observed; $^1$H NMR (400 MHz, DMSO-d$_6$) δ ppm=8.39 (s, 1H), 8.00 (s, 1H), 6.19 (td, J=2.0, 5.5 Hz, 1H), 6.05-5.90 (m, 1H), 5.41 (dt, J=2.0, 5.2 Hz, 1H), 5.26 (d, J=6.4 Hz, 1H), 4.76-4.66 (m, 1H), 3.50 (s, 3H), 2.89 (ddd, J=7.3, 8.2, 13.9 Hz, 1H), 1.68 (td, J=4.5, 13.9 Hz, 1H).

Step 4: Synthesis of 9-{(1R,4S)-4-[bis(4-methoxyphenyl)(phenyl)methoxy]cyclopent-2-en-1-yl}-1-methyl-1,9-dihydro-6H-purin-6-one (D-5)

The compound D-4 (1.17 g, 5.04 mmol) was co-evaporated with anhydrous pyridine (3x). Dissolved residue a final time in anhydrous pyridine (34 mL), added DMTCl (1.96 g, 1.15 mmol) and stirred overnight. The pyridine was removed in vacuo then the residue was dissolved in EtOAc and washed with water and brine. The organics were dried over MgSO$_4$, filtered and concentrated. The crude residue was purified via flash chromatography (80 g SiO$_2$, Isco, 0-5% MeOH/DCM) to afford D-5 (2.50 g, 93%) as a yellow solid. LCMS [M+H]=535 observed; $^1$H NMR (400 MHz, DMSO-d$_6$) δ ppm=8.36 (s, 1H) 7.98 (s, 1H) 7.44 (d, J=8.07 Hz, 2H) 7.28-7.36 (m, 6H) 7.19-7.29 (m, 1H) 6.91 (d, J=8.31 Hz, 4H) 5.97 (d, J=5.62 Hz, 1H) 5.46 (d, J=5.50 Hz, 1H) 5.24 (br. s., 1H) 4.60 (br. s., 1H) 3.74 (s, 6H) 3.50 (s, 3H) 2.34-2.45 (m, 1H) 1.54 (dt, J=13.72, 4.69 Hz, 1H).

Step 5: Synthesis of 9-{(1R,2S,3S,4S)-4-[bis(4-methoxyphenyl)(phenyl)methoxy]-2,3-dihydroxycyclopentyl}-1-methyl-1,9-dihydro-6H-purin-6-one (D-6)

To a solution of D-5 (2.50 g, 4.68 mmol) in DCM (31.2 mL) was added water (3.12 mL), NMMO (1.64 g, 14.0 mml), and OsO$_4$ (2.5 wt % in $^t$BuOH, 3.33 mL, 0.327 mmol). After stirring overnight the reaction was diluted with EtOAc then washed with sat'd Na$_2$SO$_3$ and brine. The organics were dried over MgSO$_4$, filtered and concentrated. The crude residue was purified via flash chromatography (80 g SiO$_2$, Isco, 0-8% MeOH/DCM) to afford D-6 (2.37 g, 89%). LCMS [M+H]=569 observed; $^1$H NMR (400 MHz, DMSO-d$_6$) δ ppm=8.34 (s, 1H) 8.06 (s, 1H) 7.38-7.49 (m, 2H) 7.27-7.36 (m, 6H) 7.19-7.26 (m, 1H) 6.89 (dd, J=9.05, 2.32 Hz, 4H) 5.01 (d, J=6.11 Hz, 1H) 4.74 (d, J=3.79 Hz, 1H) 4.41-4.58 (m, 2H) 3.80-3.87 (m, 1H) 3.73 (d, J=2.20 Hz, 6H) 3.56-3.62 (m, 1H) 3.50 (s, 3H) 1.84-1.97 (m, 1H) 1.36-1.55 (m, 1H).

Step 6: Synthesis of 9-[(1R,2S,3S,4S)-4-[bis(4-methoxyphenyl)(phenyl)methoxy]-3-{[tert-butyl(dimethyl)silyl]oxy}-2-hydroxycyclopentyl]-1-methyl-1,9-dihydro-6H-purin-6-one (D-7)

The compound D-6 (1.88 g, 3.31 mmol) was co-evaporated with anhydrous pyridine (3×). Dissolved residue a DMF (33 mL), added imidazole (682 mg, 9.92 mmol) then TBSCl (747 mg, 4.96 mmol) and stirred overnight. The DMF was removed in vacuo then the residue was dissolved in EtOAc and washed with water and brine. The organics were dried over MgSO$_4$, filtered and concentrated. The crude residue was purified via flash chromatography (80 g SiO$_2$, Isco, 0-100% EtOAc/heptanes) to afford D-7 (793 mg, 35%) as a white solid. LCMS [M+H]=683 observed; $^1$H NMR (400 MHz, DMSO-d$_6$) δ ppm=8.34 (s, 1H) 8.01 (s, 1H) 7.42-7.49 (m, 2H) 7.28-7.37 (m, 6H) 7.20-7.27 (m, 1H) 6.85-6.93 (m, 4H) 5.12 (d, J=5.62 Hz, 1H) 4.63-4.71 (m, 1H) 4.46-4.56 (m, 1H) 3.78-3.84 (m, 2H) 3.73 (d, J=1.71 Hz, 6H) 3.51 (s, 3H) 2.08 (ddd, J=14.58, 10.30, 6.05 Hz, 1H) 1.29 (dd, J=14.37, 6.79 Hz, 1H) 0.82 (s, 9H) 0.04 (s, 3H) −0.06 (s, 3H)

Step 7: Synthesis of (1S,2R,3S,5R)-3-[bis(4-methoxyphenyl)(phenyl)methoxy]-2-{[tert-butyl(dimethyl)silyl]oxy}-5-(1-methyl-6-oxo-1,6-dihydro-9H-purin-9-yl)cyclopentyl 2-cyanoethyl dipropan-2-ylphosphoramidoite (D-8)

To a solution of D-7 (785 g, 1.15 mmol) in DCM (23 mL) was added DIEA (601 mL, 3.45 mmol) followed by 3-((chloro(diisopropylamino)phosphanyl)oxy)propanenitrile (385 uL, 1.72 mmol) drop-wise. After 1 hour, added an additional 0.75 eq 3-((chloro(diisopropylamino)phosphanyl)oxy)propanenitrile drop-wise. After another hour, the reaction was diluted with EtOAc and washed with saturated NaHCO$_3$ and brine. The organics were dried over MgSO$_4$, filtered and concentrated. The crude residue was purified via flash chromatography (40 g SiO$_2$, Isco, 0-100% EtOAc/heptanes) to afford D-8 (779 mg, 77%) as a white solid. LCMS [M+H]=800 observed; $^1$H NMR (400 MHz, DMSO-d$_6$) δ ppm=8.36 (d, J=1.83 Hz, 1H) 7.95 (d, J=14.18 Hz, 1H) 7.48 (d, J=7.95 Hz, 2H) 7.33 (td, J=5.84, 2.51 Hz, 6H) 7.22-7.29 (m, 1H) 6.87-6.95 (m, 4H) 4.69-4.92 (m, 2H) 3.85 (d, J=6.36 Hz, 1H) 3.74 (s, 6H) 3.70 (br. s., 1H) 3.56-3.67 (m, 1H) 3.51 (d, J=6.24 Hz, 3H) 3.33-3.48 (m, 3H) 2.54-2.76 (m, 2H) 2.09-2.48 (m, 1H) 1.21-1.53 (m, 1H) 0.95-1.08 (m, 9H) 0.71-0.85 (m, 12H) 0.06 (d, J=19.32 Hz, 3H) −0.11 (d, J=10.51 Hz, 3H); $^{31}$P NMR (162 MHz, DMSO-d$_6$, internal reference H$_3$PO$_4$) δ ppm=148.32 (s, 1P), 146.67 (s, 1P).

Scheme E

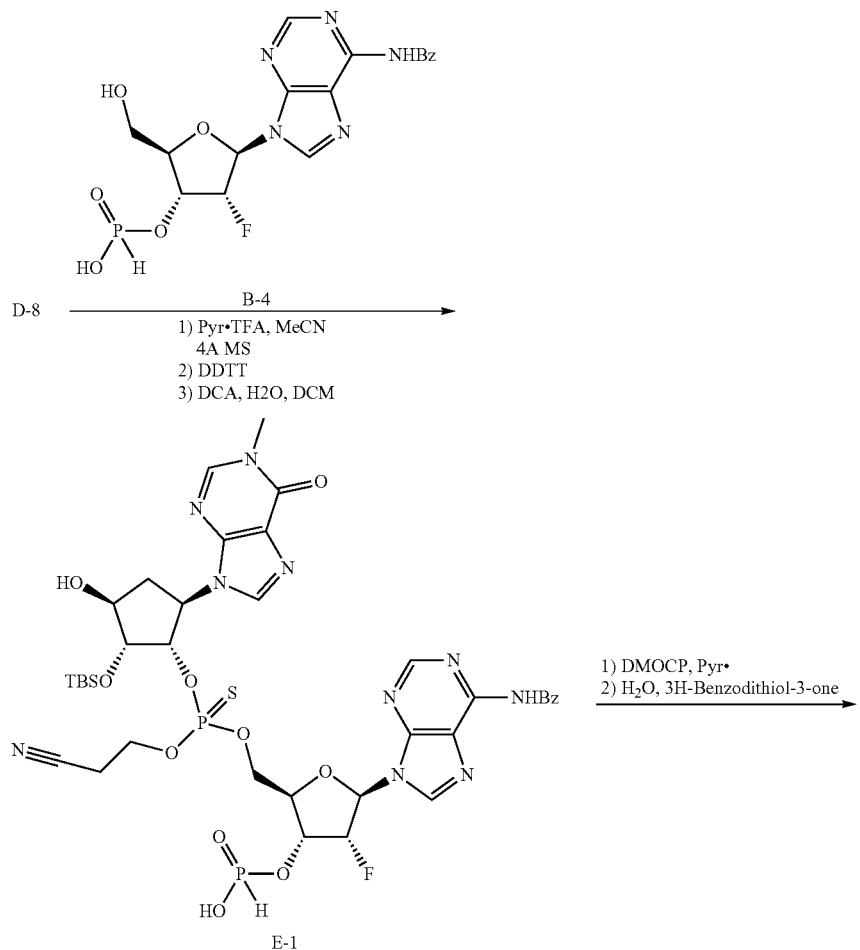

E-1

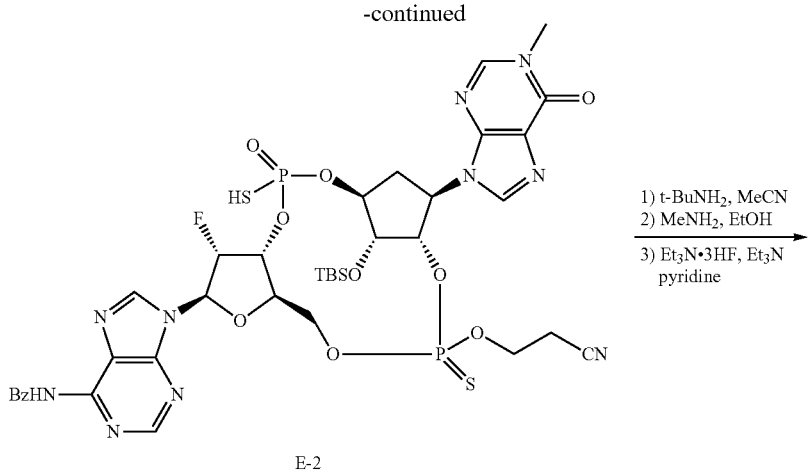

E-2

1) t-BuNH₂, MeCN
2) MeNH₂, EtOH
3) Et₃N·3HF, Et₃N pyridine

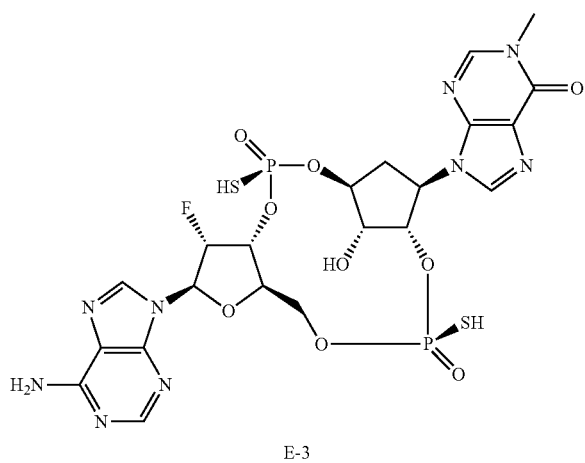 [SMILES: Cn1cnc2c(ncn2[C@@H]2C[C@@H]3O[P@](=O)(S)O[C@H]4[C@@H](F)[C@H](n5cnc6c(N)ncnc65)O[C@@H]4CO[P@](=O)(S)O[C@@H]2[C@@H]3O)c1=O ; "E-3"]

E-3

Step 1: Synthesis of N-benzoyl-5'-O-[{[(1S,2R,3S,5R)-2-{[tert-butyl(dimethyl)silyl]oxy}-3-hydroxy-5-(1-methyl-6-oxo-1,6-dihydro-9H-purin-9-yl)cyclopentyl]oxy}(2-cyanoethoxy)phosphorothioyl]-2'-deoxy-2'-fluoro-3'-O-[hydroxy(oxido)-I⁵-phosphanyl]adenosine (E-1)

The compound D-8 (709 mg, 0.803 mmol) was co-evaporated with THF (3×). Dissolved a final time in THF (20 mL) added powdered molecular sieves and stirred for 1 hour (flask A). A mixture of B-4 (351 mg, 0.803 mmol) and pyTFA (930 mg, 4.82 mol) was co-evaporated with THF (3×). Dissolved a final time in THF (20 mL) added powdered molecular sieves and stirred for 1 hour (flask B). The contents of flask B were then added to flask A. After 30 min, DDTT (330 mg, 1.61 mmol) was added. After another 30 min, the reaction mixture was concentrated and the residue was slurried in DCM. Filtered out molecular sieves and concentrated mother liquor. Dissolved residue in DCM (4 mL) added a few drops of water then a solution of DCA (662 uL, 8.03 mmol) in DCM (4 mL) resulting in a bright orange solution. After 30 min, pyridine was added until the orange color dissipated. The reaction mixture was concentrated and purified via flash chromatography (40 g SiO₂, Isco, 0-40% MeOH/DCM then 12 g SiO₂, Isco, 0-40% MeOH/DCM) to afford E-1 (227 mg, 30%). LCMS [M+H]=950 observed; ³¹P NMR (162 MHz, DMSO-d₆) δ ppm=67.93 (s., 1P), 65.55 (s, 1P), −0.34 (s, 1P), −0.68 (s, 1P); ¹⁹F NMR (376 MHz, DMSO-d₆) δ ppm=−200.59 (s, 1F), −201.37 (s, 1F).

Step 2: Synthesis of N-{9-[(4S,6R,7S,11aR,13R,14R,14aR,15R)-15-{[tert-butyl(dimethyl)silyl]oxy}-9-(2-cyanoethoxy)-4-fluoro-6-(1-methyl-6-oxo-1,6-dihydro-9H-purin-9-yl)-2-oxido-2-sulfanyl-9-sulfidooctahydro-11H-4,7-methanofuro[3,2-d][1,3,7,9,2,8]tetraoxadiphosphacyclotridecin-13-yl]-9H-purin-6-yl}benzamide (E-2)

The compound E-1 (227 mg, 0.239 mmol) was co-evaporated with anhydrous pyridine (3×). Dissolved residue a final time in anhydrous pyridine (12 mL) then added DMOCP (221 mg, 1.20 mmol). After 1 hour an additional 5 eq of DMOCP were added. After 4 hours, added water (1.0 mL) followed by 3H-1,2-benzodithiol-3-one (81 mg, 0.48 mmol). After 30 min the reaction was quenched with saturated NaHCO₃, concentrated and purified via flash chromatography (24 g SiO₂, Isco, 0-40% MeOH/DCM) to afford E-2 (155 mg, 67%). LCMS 4 peaks with [M+H]=964 observed; ³¹P NMR (162 MHz, DMSO-d₆) δ ppm=67.40 (s, 1P), 67.02 (s, 1P), 63.92 (s, 1P), 63.80 (s, 1P), 49.90 (s, 1P), 49.83 (s, 1P), 49.38 (s, 1P); ¹⁹F NMR (376 MHz, DMSO-d₆) δ ppm=−195.70 (s, 1F), −196.27 (s, 1F), −196.54 (s, 1F), −196.55 (s, 1F)

Step 3: Synthesis of 9-[(4S,6R,7S,11aR,13R,14R, 14aR,15R)-13-(6-amino-9H-purin-9-yl)-14-fluoro-15-hydroxy-2,9-dioxido-2,9-disulfanyloctahydro-11H-4,7-methanofuro[3,2-d][1,3,7,9,2,8]tetraoxadiphosphacyclotridecin-6-yl]-1-methyl-1,9-dihydro-6H-purin-6-one (E-3)

To a solution of E-2 (260 mg, 0.270 mmol) in ACN (6 mL) was added tBuNH$_2$. After 15 min, the reaction was concentrated and the residue was dissolved in 33% MeNH$_2$ in EtOH (6 mL). After 2 hrs, the reaction was concentrated and the residue was co-evaporated with 3:1 pyridine:TEA (2×). Dissolved the residue in pyridine (3 mL), added TEA (300 uL) followed by triethylamine trihydrofluoride (2.2 mL, 13.5 mmol) and heated to 50° C. overnight. Concentrated then adjusted pH to ~6 with saturated NaHCO$_3$. Concentrated, slurried residue in DCM, filtered out solids then concentrated mother liquor. The residue was purified by reverse phase prep-HPLC (Phenomenex Gemini C18 21.2× 150 mm 5 u column) eluted with 5-10% MeCN in aq. NH$_4$HCO$_3$ (10 mM) to give 4 diastereomers. Peaks 3 and 4 were re-purified using the same conditions.

Peak 1:
25 mg, 13%;
$^1$H NMR (400 MHz, DMSO-d$_6$) δ ppm=8.44 (s, 1H) 8.21 (s, 1H) 8.20 (s, 1H) 8.10 (s, 1H) 7.40 (br. s., 2H) 6.29 (d, J=17.85 Hz, 2H) 5.43-5.60 (m, 1H) 5.07-5.16 (m, 1H) 4.97 (td, J=9.93, 5.93 Hz, 2H) 4.51-4.61 (m, 2H) 4.23 (d, J=8.56 Hz, 1H) 4.00 (br. s., 2H) 3.50 (s, 3H) 2.83 (br. s., 1H) 1.66 (dd, J=14.49, 5.81 Hz, 1H);
$^{31}$P NMR (162 MHz, DMSO-d$_6$, internal reference H$_3$PO$_4$) δ ppm=53.68 (s, 1P), 50.53 (s, 1P);
$^{19}$F NMR (376 MHz, DMSO-d$_6$) δ ppm=−197.42 (s, 1F).

Peak 2:
32 mg, 16%;
$^1$H NMR (400 MHz, DMSO-d$_6$) δ ppm=8.44 (s, 1H) 8.22 (s, 1H) 8.18 (s, 1H) 8.13 (s, 1H) 7.40 (br. s., 2H) 6.28 (d, J=17.24 Hz, 1H) 6.02-6.20 (m, 1H) 5.06-5.15 (m, 1H) 4.95 (td, J=9.90, 5.50 Hz, 2H) 4.56 (br. s., 1H) 4.43 (t, J=5.26 Hz, 1H) 4.24 (d, J=8.44 Hz, 1H) 3.96-4.12 (m, 2H) 3.49 (s, 3H) 2.80 (br. s., 1H) 1.61 (dd, J=14.92, 5.50 Hz, 1H);
$^{31}$P NMR (162 MHz, DMSO-d$_6$, internal reference H$_3$PO$_4$) δ ppm=53.33 (s, 1P), 48.21 (s, 1P);
$^{19}$F NMR (376 MHz, DMSO-d$_6$) δ ppm=−198.33 (s, 1F).

Peak 3:
34 mg, 16%;
$^1$H NMR (400 MHz, DMSO-d$_6$) δ ppm=8.41 (s, 1H) 8.36 (br. s., 1H) 8.23 (s, 1H) 8.18 (s, 1H) 7.40 (br. s., 2H) 6.29 (d, J=16.38 Hz, 1H) 6.04-6.22 (m, 1H) 5.12-5.26 (m, 1H) 4.77-4.96 (m, 2H) 4.37-4.48 (m, 2H) 4.28 (d, J=8.80 Hz, 1H) 4.18 (d, J=11.98 Hz, 1H) 4.02 (dd, J=11.74, 5.50 Hz, 1H) 3.50 (s, 3H) 2.86 (br. s., 1H) 1.52 (dd, J=15.22, 5.81 Hz, 1H);
$^{31}$P NMR (162 MHz, DMSO-d$_6$, internal reference H$_3$PO$_4$) δ ppm=49.42 (s, 1P), 48.13 (s, 1P);
$^{19}$F NMR (376 MHz, DMSO-d$_6$) δ ppm=−199.27 (s, 1F).

Peak 4:
7 mg, 3.5%;
$^1$H NMR (400 MHz, DMSO-d$_6$) δ ppm=8.40 (s, 1H) 8.27 (s, 1H) 8.20 (s, 1H) 8.19 (s, 1H) 7.38 (br. s., 2H) 6.27 (d, J=16.63 Hz, 1H) 5.40-5.60 (m, 1H) 5.24 (d, J=3.42 Hz, 1H) 5.15-5.23 (m, 1H) 4.82-4.99 (m, 2H) 4.52 (t, J=6.36 Hz, 1H) 4.45 (br. s., 1H) 4.26 (d, J=9.29 Hz, 1H) 4.09-4.18 (m, 1H) 3.97-4.06 (m, 1H) 3.49 (s, 3H) 2.85 (t, J=16.08 Hz, 1H) 1.56 (dd, J=14.67, 5.99 Hz, 1H);

$^{31}$P NMR (162 MHz, DMSO-d$_6$, internal reference H$_3$PO$_4$) δ ppm=50.54 (s, 1P), 48.91 (s, 1P);
$^{19}$F NMR (376 MHz, DMSO-d$_6$) δ ppm=−198.50 (s, 1F).

Example 3

9-[(4S,6R,7S,11aR,13R,14R,14aR,15R)-13-(6-amino-9H-purin-9-yl)-14-fluoro-15-hydroxy-2,9-dioxido-2,9-disulfanyloctahydro-11H-4,7-methanofuro[3,2-d][1,3,7,9,2,8]tetraoxadiphosphacyclotridecin-6-yl]-1,9-dihydro-6H-purin-6-one

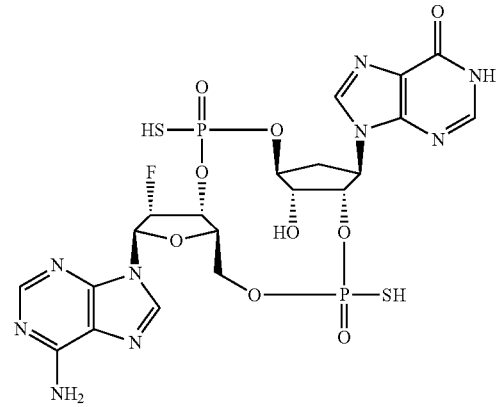 [SMILES: Nc1ncnc2c1ncn2[C@@H]1O[C@@H]2COP(=O)(S)O[C@@H]3[C@H](O)[C@H](C[C@H]3n3cnc4c(=O)[nH]cnc43)OP(=O)(S)O[C@H]2[C@H]1F]

Scheme F

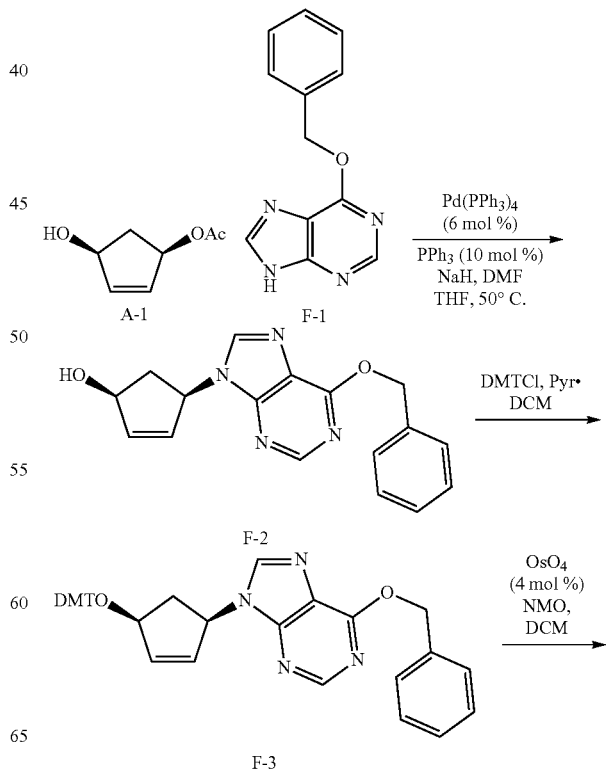

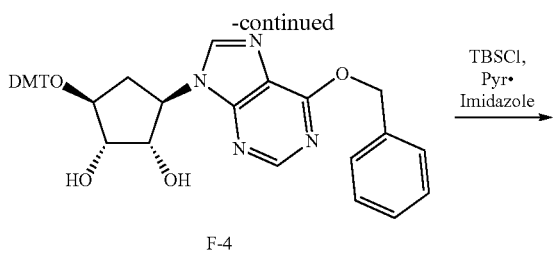

F-4

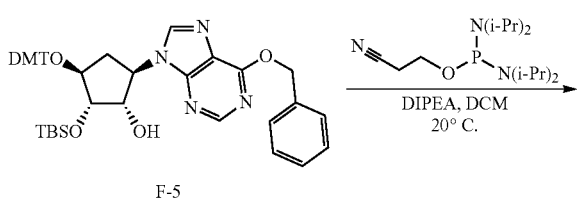

F-5

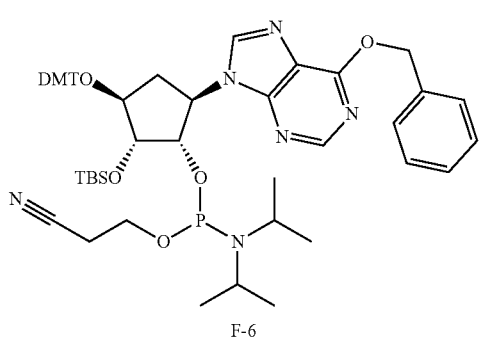

F-6

Step 1: Synthesis of (1S,4R)-4-(6-(benzyloxy)-9H-purin-9-yl)cyclopent-2-en-1-ol (F-2)

Compound F-2 was made in a similar fashion as A-3 using 6-(benzyloxy)-9H-purine (F-1) in place of A-2 in step 1 of Scheme A in 67% yield.

$^1$H NMR (400 MHz, DMSO-d$_6$) δ=8.56 (s, 1H), 8.32 (s, 1H), 7.55-7.48 (m, 2H), 7.45-7.31 (m, 3H), 6.21 (td, J=2.0, 5.5 Hz, 1H), 6.09-5.99 (m, 1H), 5.63 (s, 2H), 5.55 (dt, J=2.0, 5.2 Hz, 1H), 5.36 (d, J=6.4 Hz, 1H), 4.74 (td, J=1.5, 3.1 Hz, 1H), 3.00-2.84 (m, 1H), 1.75 (td, J=4.4, 13.9 Hz, 1H); LCMS [M+H]=309.0.

Step 2: Synthesis of 6-(benzyloxy)-9-((1R,4S)-4-(bis(4-methoxyphenyl)(phenyl)-14-oxidaneyl)cyclopent-2-en-1-yl)-9H-purine (F-3)

Compound F-3 was made in a similar fashion as A-4 in step 2 of Scheme A in 82% yield.

$^1$H NMR (400 MHz, DMSO-d$_6$) δ=8.54 (s, 1H), 8.29 (s, 1H), 7.51 (d, J=7.0 Hz, 2H), 7.47-7.35 (m, 5H), 7.35-7.28 (m, 6H), 7.26-7.20 (m, 1H), 6.90 (dd, J=2.1, 9.0 Hz, 4H), 6.00 (d, J=6.0 Hz, 1H), 5.63 (s, 2H), 5.48-5.42 (m, 1H), 5.38 (t, J=6.1 Hz, 1H), 4.61 (t, J=5.0 Hz, 1H), 3.73 (d, J=1.3 Hz, 6H), 2.48-2.39 (m, 1H), 1.61 (td, J=4.8, 13.8 Hz, 1H); LCMS [M+H]=610.8.

Step 3: Synthesis of (1S,2S,3R,5S)-3-(6-(benzyloxy)-9H-purin-9-yl)-5-(bis(4-methoxyphenyl)(phenyl)-14-oxidaneyl)cyclopentane-1,2-diol (F-4)

Compound F-4 was made in a similar fashion as A-5 in step 3 of Scheme A in 76% yield.

$^1$H NMR (400 MHz, DMSO-d$_6$) δ=8.55 (s, 1H), 8.37 (s, 1H), 7.53-7.44 (m, 4H), 7.40 (d, J=7.3 Hz, 3H), 7.36-7.27 (m, 6H), 7.26-7.18 (m, 1H), 6.88 (dd, J=3.1, 8.9 Hz, 4H), 5.63 (s, 2H), 5.04 (d, J=6.1 Hz, 1H), 4.77 (d, J=3.7 Hz, 1H), 4.68-4.55 (m, 2H), 3.86 (td, J=2.4, 4.6 Hz, 1H), 3.72 (d, J=2.8 Hz, 6H), 3.59 (br. s., 1H), 2.01-1.90 (m, 1H), 1.66-1.55 (m, 1H); LCMS [M+H]=645.8.

Step 4: Synthesis of (1S,2S,3S,5R)-5-(6-(benzyloxy)-9H-purin-9-yl)-3-(bis(4-methoxyphenyl)(phenyl)-14-oxidaneyl)-2-((tert-butyldimethylsilyl)oxy)cyclopentan-1-ol (F-5)

Compound F-5 was made in a similar fashion as A-6 in step 3 of Scheme A in 35% yield.

$^1$H NMR (400 MHz, DMSO-d$_6$) δ=8.56 (s, 1H), 8.32 (s, 1H), 7.49 (dd, J=7.2, 14.1 Hz, 4H), 7.40 (d, J=7.3 Hz, 3H), 7.36-7.28 (m, 6H), 7.26-7.19 (m, 1H), 6.88 (dd, J=3.2, 8.9 Hz, 4H), 5.64 (s, 2H), 5.14 (d, J=5.5 Hz, 1H), 4.86-4.76 (m, 1H), 4.71-4.57 (m, 1H), 3.87-3.75 (m, 2H), 3.72 (d, J=2.3 Hz, 6H), 2.13 (ddd, J=6.4, 10.3, 14.7 Hz, 1H), 1.44 (dd, J=6.9, 14.4 Hz, 1H), 0.82 (s, 9H), 0.04 (s, 3H), −0.07 (s, 3H); LCMS [M+H]=758.8.

Step 5: Synthesis of (1S,2R,3S,5R)-5-(6-(benzyloxy)-9H-purin-9-yl)-3-(bis(4-methoxyphenyl)(phenyl)-14-oxidaneyl)-2-((tert-butyldimethylsilyl)oxy)cyclopentyl (2-cyanoethyl) diisopropylphosphoramidite (F-6)

Compound F-6 was made in a similar fashion as A-7 in step 3 of Scheme A in 73% yield. $^{31}$P NMR (162 MHz, DMSO-d$_6$) δ=149.11 (br. s., 1P), 147.26 (s, 1P); LCMS [M+H]=959.0.

Scheme G

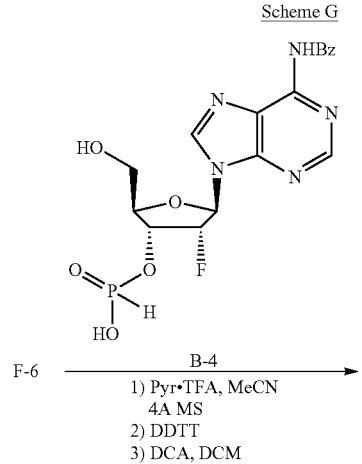

F-6 $\xrightarrow{\text{1) Pyr·TFA, MeCN, 4A MS; 2) DDTT; 3) DCA, DCM}}$

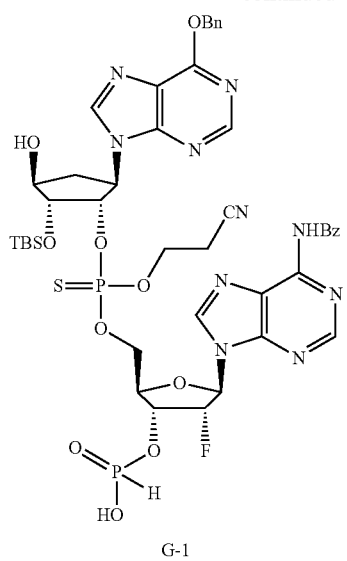

G-1

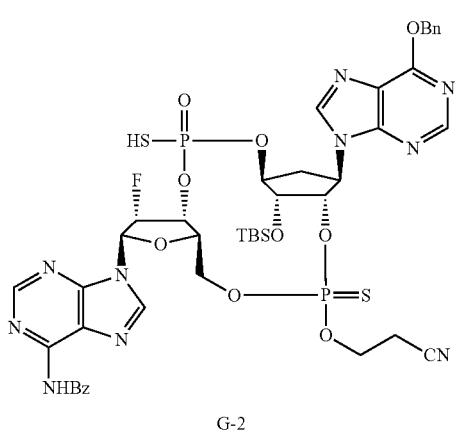

G-2

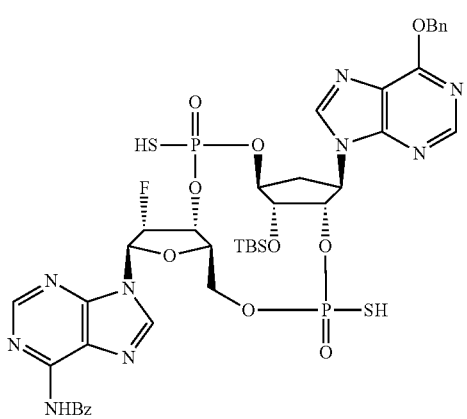

G-3

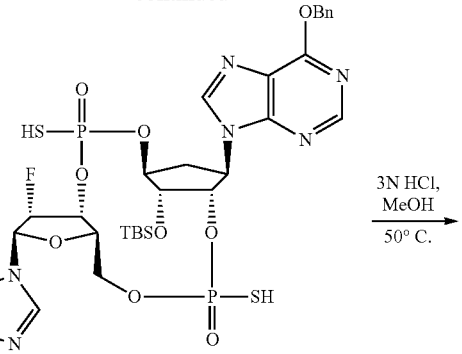

G-4

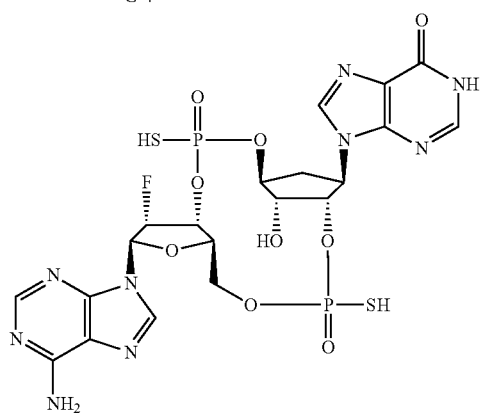

G-5

Step 1: Synthesis of (2R,3R,4R,5R)-5-(6-benzamido-9H-purin-9-yl)-2-((((((1S,2R,3S,5R)-5-(6-(benzyloxy)-9H-purin-9-yl)-2-((tert-butyldimethylsilyl)oxy)-3-hydroxycyclopentyl)oxy)(2-cyanoethoxy)phosphorothioyl)oxy)methyl)-4-fluorotetrahydrofuran-3-yl hydrogen phosphonate (G-1)

Compound G-1 was made in a similar fashion as E-1 in step 1 of Scheme E in 42% yield.

$^{19}$F NMR (376 MHz, DMSO-d$_6$) δ=−201.22 (s, 1F), −201.70 (s, 1F); $^{31}$P NMR (162 MHz, DMSO-d$_6$) δ=68.34 (s, 1P), 65.79 (s, 1P), −0.03 (s, 1P), −0.15 (s, 1P); LCMS [M+H]=1025.

Step 2: Synthesis of N-{9-[(4S,6R,7S,11aR,13R,14R,14aR,15R)-6-[6-(benzyloxy)-9H-purin-9-yl]-15-{[tert-butyl(dimethyl)silyl]oxy}-9-(2-cyanoethoxy)-14-fluoro-2-oxido-2-sulfanyl-9-sulfidooctahydro-11H-4,7-methanofuro[3,2-d][1,3,7,9,2,8]tetraoxadiphosphacyclotridecin-13-yl]-9H-purin-6-yl}benzamide (G-2)

Compound G-2 was made in a similar fashion as E-2 in step 2 of Scheme E in 29% yield. $^{19}$F NMR (376 MHz, DMSO-d$_6$) δ=−194.72 (s, 1F), −196.58 (s, 1F), −196.67 (s, 1F), −196.96 (s, 1F); $^{31}$P NMR (162 MHz, DMSO-d$_6$) δ=67.91 (s, 1P), 67.60 (br. s., 1P), 63.96 (br. s., 1P), 63.78 (br. s., 1P), 51.01 (s, 2P), 49.48 (s, 1P), 48.94 (s, 1P); LCMS [M+H]=1039.

Step 3: Synthesis of 9-[(4S,6R,7S,11aR,13R,14R,14aR,15R)-13-(6-amino-9H-purin-9-yl)-14-fluoro-15-hydroxy-2,9-dioxido-2,9-disulfanyloctahydro-11H-4,7-methanofuro[3,2-d][1,3,7,9,2,8]tetraoxadiphosphacyclotridecin-6-yl]-1,9-dihydro-6H-purin-6-one (G-5)

Compound G-2 was treated in a similar fashion as compound E-2 in step 3 of Scheme E to give G-3 followed by G-4. Finally, to a solution of G-4 (156 mg, 0.18 mmol) in MeOH (3.00 mL, c=0.06 M) was added 3N HCl (300 mg, 9 mmol, 3.00 mL, 3 M). Upon addition of HCl a white precipitate formed. The suspension was heated to 50° C. During heating the reaction became a homogeneous yellow solution. Stirring was continued at 50° C. for 4.5 h. The reaction was cooled to rt then neutralized to pH 6 with NaHCO$_3$(sat). The aqueous mixture was lyophilized then purified by Prep HPLC to give 4 diastereomers.

Peak 1: 41 mgs, 28% yield, 95% de, $^1$H NMR (400 MHz, DEUTERIUM OXIDE) δ=8.43 (s, 1H), 8.26 (s, 1H), 8.21 (s, 1H), 7.68 (s, 1H), 6.49 (d, J=16.1 Hz, 1H), 5.73-5.57 (m, 1H), 5.52-5.42 (m, 1H), 5.24-5.09 (m, 2H), 4.60 (br. s., 1H), 4.52 (d, J=8.8 Hz, 1H), 4.33 (d, J=11.6 Hz, 1H), 4.12 (dd, J=6.4, 11.7 Hz, 1H), 3.13-2.99 (m, 1H), 2.30 (dd, J=5.6, 16.1 Hz, 1H), One non-exchangeable proton is obscured by the solvent peak and is not tabulated. $^{19}$F NMR (376 MHz, DEUTERIUM OXIDE) δ=−199.99 (s, 1F); $^{31}$P NMR (162 MHz, DEUTERIUM OXIDE) δ=55.96 (br. s., 1P), 51.76 (s, 1P) (internal standard H$_3$PO$_4$); LCMS [M+H]=678.

Peak 2: 30 mgs, 19% yield, 95% de, $^1$H NMR (400 MHz, DEUTERIUM OXIDE) δ=8.45 (s, 1H), 8.27 (s, 1H), 8.21 (s, 1H), 7.68 (s, 1H), 6.49 (d, J=15.9 Hz, 1H), 6.33-6.14 (m, 1H), 5.55-5.43 (m, 1H), 5.13 (dd, J=10.9, 14.9 Hz, 2H), 4.64 (d, J=5.3 Hz, 1H), 4.61 (br. s., 1H), 4.55 (d, J=8.9 Hz, 1H), 4.36 (d, J=10.6 Hz, 1H), 4.16 (dd, J=5.9, 12.0 Hz, 1H), 3.10-2.97 (m, 1H), 2.25 (dd, J=5.8, 15.8 Hz, 1H); $^{19}$F NMR (376 MHz, DEUTERIUM OXIDE) δ=−200.31 (s, 1F); $^{31}$P NMR (162 MHz, DEUTERIUM OXIDE) δ=55.98 (s, 1P), 50.38 (s, 1P) (H$_3$PO$_4$ internal standard); LCMS [M+H]=678.

Peak 3: 8 mgs, 7% yield, 93% de, $^1$H NMR (400 MHz, DEUTERIUM OXIDE) δ=8.30 (s, 1H), 8.27 (s, 1H), 8.20 (s, 1H), 7.64 (s, 1H), 6.47 (d, J=16.5 Hz, 1H), 6.33-6.15 (m, 1H), 5.60-5.50 (m, 1H), 5.18-5.06 (m, 2H), 4.63 (d, J=2.6 Hz, 2H), 4.55 (d, J=9.7 Hz, 1H), 4.43 (d, J=12.3 Hz, 1H), 4.13-4.03 (m, 1H), 3.07-2.94 (m, 1H), 2.19 (dd, J=5.5, 15.8 Hz, 1H); $^{19}$F NMR (376 MHz, DEUTERIUM OXIDE) δ=−200.30 (s, 1F); $^{31}$P NMR (162 MHz, DEUTERIUM OXIDE) δ=51.72 (br. s., 1P), 50.31 (s, 1P) (H$_3$PO$_4$ internal standard); LCMS [M+H]=678.

Peak 4: 8 mgs, 6% yield, 93% de, $^1$H NMR (400 MHz, DEUTERIUM OXIDE) δ=8.29 (br. s., 1H), 8.27 (br. s., 1H), 8.19 (s, 1H), 7.65 (br. s., 1H), 6.47 (d, J=16.0 Hz, 1H), 5.75-5.46 (m, 2H), 5.13 (br. s., 2H), 4.69 (br. s., 1H), 4.62 (br. s., 1H), 4.53 (d, J=7.8 Hz, 1H), 4.40 (d, J=10.8 Hz, 1H), 4.11-4.02 (m, 1H), 3.04 (br. s., 1H), 2.23 (d, J=15.4 Hz, 1H); $^{19}$F NMR (376 MHz, DEUTERIUM OXIDE) δ=−199.96 (br. s., 1F); $^{31}$P NMR (162 MHz, DEUTERIUM OXIDE) b=53.04 (br. s., 1P)(only one peak observed, H3PO4 internal standard); LCMS [M+H]=678.

Example 4

(4S,6R,7S,11aR,13R,14R,14aR,15R)-6-(4-amino-7-methyl-1H-imidazo[4,5-c]pyridin-1-yl)-13-(6-amino-9H-purin-9-yl)-14-fluoro-2,9-disulfanyloctahydro-11H-4,7-methanofuro[3,2-d][1,3,7,9,2,8]tetraoxadiphosphacyclotridecin-15-ol 2,9-dioxide

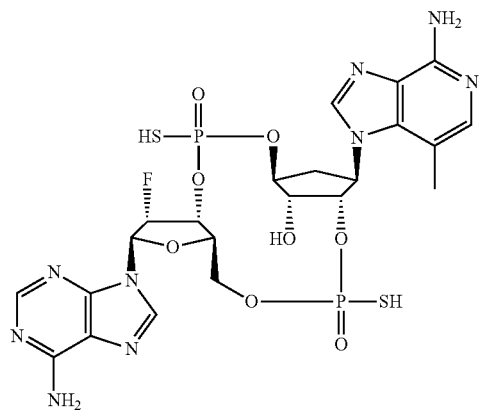 [SMILES: Cc1cnc(N)c2ncn([C@@H]3C[C@@H]4OP(=O)(S)O[C@H]5[C@@H](F)[C@H](n6cnc7c(N)ncnc76)O[C@@H]5COP(=O)(S)O[C@@H]3[C@@H]4O)c12]

Example 4 is made in a similar fashion as Example 1 using N-(7-methyl-1H-imidazo[4,5-c]pyridin-4-yl)benzamide in place of A-2 in step 1 of Scheme A.

Example 5

9-[(4S,6R,7S,11aR,13R,14R,14aR,15R)-13-(6-amino-9H-purin-9-yl)-14-fluoro-15-hydroxy-2,9-dioxido-2,9-disulfanyloctahydro-11H-4,7-methanofuro[3,2-d][1,3,7,9,2,8]tetraoxadiphosphacyclotridecin-6-yl]-3-methyl-3,9-dihydro-6H-purin-6-one

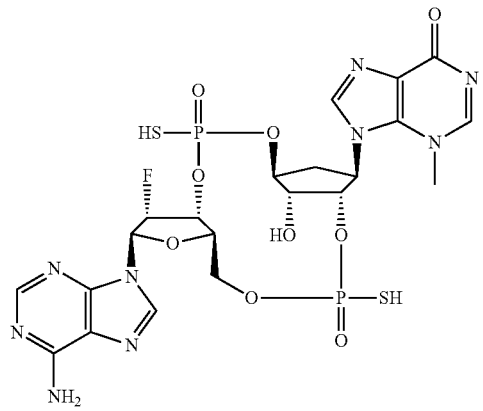 [SMILES: Cn1cnc(=O)c2ncn([C@@H]3C[C@@H]4OP(=O)(S)O[C@H]5[C@@H](F)[C@H](n6cnc7c(N)ncnc76)O[C@@H]5COP(=O)(S)O[C@@H]3[C@@H]4O)c21]

Example 5 is made in a similar fashion as Example 1 using 3-methyl-3,9-dihydro-6H-purin-6-one in place of A-2 in step 1 of Scheme A.

Example 6

3-[(4S,6R,7S,11aR,13R,14R,14aR,15R)-13-(6-amino-9H-purin-9-yl)-14-fluoro-15-hydroxy-2,9-dioxido-2,9-disulfanyloctahydro-11H-4,7-methanofuro[3,2-d][1,3,7,9,2,8]tetraoxadiphosphacyclotridecin-6-yl]-4-methyl-3,4-dihydro-7H-imidazo[4,5-b]pyridin-7-one

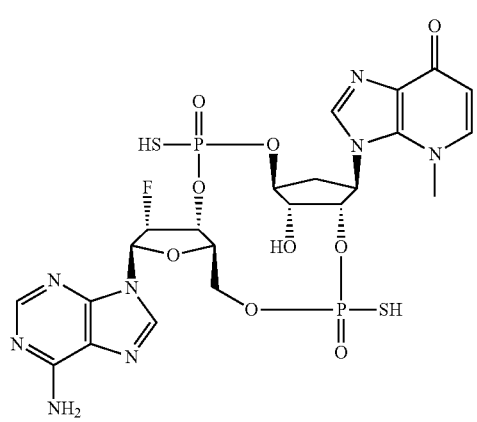 [SMILES: Cn1ccc(=O)c2ncn([C@@H]3C[C@@H]4OP(=O)(S)O[C@H]5[C@@H](F)[C@H](n6cnc7c(N)ncnc76)O[C@@H]5COP(=O)(S)O[C@@H]3[C@@H]4O)c21]

Example 6 is made in a similar fashion as Example 1 using 4-methyl-3,4-dihydro-7H-imidazo[4,5-b]pyridin-7-one in place of A-2 in step 1 of Scheme A.

Example 7

9-[(4S,6R,7S,11aR,13R,14R,14aR,15R)-13-(6-amino-9H-purin-9-yl)-14-fluoro-15-hydroxy-2,9-dioxido-2,9-disulfanyloctahydro-11H-4,7-methanofuro[3,2-d][1,3,7,9,2,8]tetraoxadiphosphacyclotridecin-6-yl]-2-methyl-1,9-dihydro-6H-purin-6-one

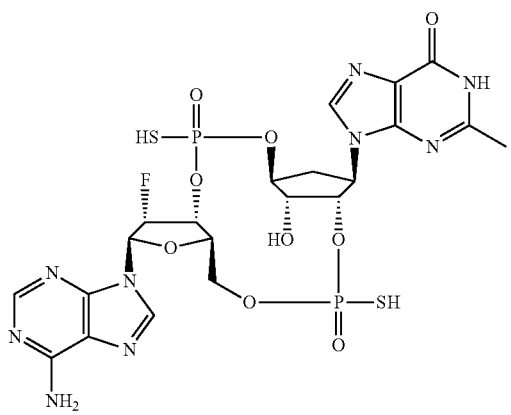 [SMILES: Cc1nc2c(ncn2[C@@H]2C[C@@H]3OP(=O)(S)O[C@H]4[C@@H](F)[C@H](n5cnc6c(N)ncnc65)O[C@@H]4COP(=O)(S)O[C@@H]2[C@@H]3O)c(=O)[nH]1]

Example 7 was made in a similar fashion as Example 3 using 6-(benzyloxy)-2-methyl-9H-purine in place of F-1 in step 1 of Scheme F.

Peak 1—$^1$H NMR (400 MHz, Methanol-$d_4$) δ 8.72 (s, 1H), 8.26 (s, 1H), 8.25 (s, 2H), 6.42 (d, J=15.8 Hz, 1H), 5.62 (dd, J=50.8, 3.7 Hz, 1H), 5.46 (ddd, J=13.1, 9.1, 2.8 Hz, 1H), 5.28-5.14 (m, 2H), 4.80 (t, J=6.2 Hz, 1H), 4.68 (s, 1H), 4.46 (d, J=9.0 Hz, 1H), 4.43-4.35 (m, 1H), 4.18 (dd, J=11.8, 5.7 Hz, 1H), 3.09-2.96 (m, 1H), 2.25 (s, 3H), 2.11 (dd, J=15.1, 6.0 Hz, 1H); $^{19}$F NMR (376 MHz, MeOD) δ −200.3; $^{31}$P NMR (162 MHz, MeOD) δ 59.20, 55.02; LCMS [M+H]=692.

Peak 2—$^1$H NMR (400 MHz, Methanol-$d_4$) δ 8.73 (s, 1H), 8.25 (s, 1H), 8.24 (s, 1H), 6.41 (d, J=15.5 Hz, 1H), 6.22 (dd, J=50.3, 3.6 Hz, 1H), 5.57-5.48 (m, 1H), 5.23-5.09 (m, 2H), 4.70 (s, 1H), 4.71-4.63 (m, 1H), 4.45 (dd, J=16.5, 10.9 Hz, 2H), 4.23 (dd, J=11.7, 5.6 Hz, 1H), 2.95 (ddd, J=11.8, 8.3, 4.7 Hz, 1H), 2.14 (dd, J=15.1, 6.0 Hz, 1H); $^{19}$F NMR (376 MHz, MeOD) 5-201.4; $^{31}$P NMR (162 MHz, MeOD) δ 59.33, 53.25; LCMS [M+H]=692.

Peak 3—$^1$H NMR (400 MHz, Methanol-$d_4$) δ 8.38 (s, 1H), 8.15 (s, 1H), 8.13 (s, 1H), 6.29 (d, J=16.2 Hz, 1H), 6.12 (dd, J=50.3, 3.4 Hz, 1H), 5.36 (t, J=9.4 Hz, 1H), 5.13-4.88 (m, 2H), 4.59 (d, J=5.8 Hz, 2H), 4.34 (t, J=10.5 Hz, 2H), 4.18 (dd, J=12.4, 6.4 Hz, 1H), 2.93-2.77 (m, 1H), 2.13 (s, 3H), 1.98 (d, J=15.0 Hz, 1H); $^{19}$F NMR (376 MHz, MeOD) δ −201.2; $^{31}$P NMR (162 MHz, MeOD) δ 54.06, 52.75; LCMS [M+H]=692.

Peak 4—$^1$H NMR (400 MHz, Methanol-$d_4$) δ 8.35 (s, 1H), 8.13 (s, 1H), 8.11 (s, 1H), 6.28 (d, J=16.5 Hz, 1H), 5.49 (dd, J=51.1, 3.6 Hz, 1H), 5.25 (td, J=9.2, 2.8 Hz, 1H), 5.11 (td, J=10.3, 9.8, 5.7 Hz, 1H), 4.96 (ddt, J=23.4, 9.3, 4.8 Hz, 1H), 4.70 (t, J=6.2 Hz, 1H), 4.58 (s, 1H), 4.37-4.27 (m, 2H), 4.17 (dd, J=12.3, 6.8 Hz, 1H), 2.92 (dddd, J=14.8, 10.4, 6.1, 3.3 Hz, 1H), 2.19 (s, 3H), 1.92-1.86 (m, 1H); $^{19}$F NMR (376 MHz, MeOD) δ −200.8; $^{31}$P NMR (162 MHz, MeOD) δ 55.16, 53.92; LCMS [M+H]=692.

Example 8

2-amino-9-[(4S,6R,7S,11aR,13R,14R,14aR,15R)-13-(6-amino-9H-purin-9-yl)-14-fluoro-15-hydroxy-2,9-dioxido-2,9-disulfanyloctahydro-11H-4,7-methanofuro[3,2-d][1,3,7,9,2,8]tetraoxadiphosphacyclotridecin-6-yl]-1,9-dihydro-6H-purin-6-one

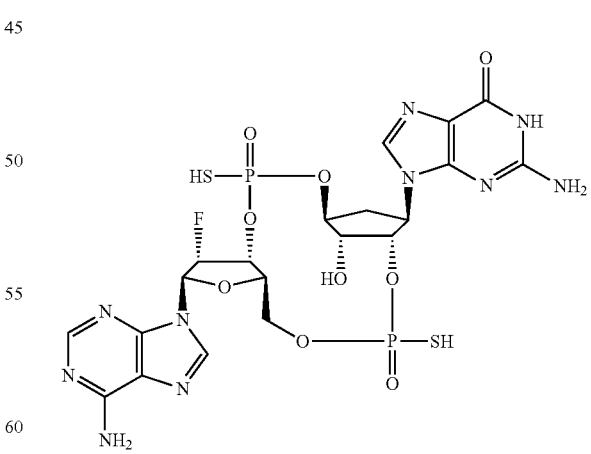

Example 8 is made in a similar fashion as Example 1 using N-(6-(benzyloxy)-9H-purin-2-yl)benzamide in place of A-2 in step 1 of Scheme A.

Example 9

5-amino-3-[(4S,6R,7S,11aR,13R,14R,14aR,15R)-13-(6-amino-9H-purin-9-yl)-14-fluoro-15-hydroxy-2,9-dioxido-2,9-disulfanyloctahydro-11H-4,7-methanofuro[3,2-d][1,3,7,9,2,8]tetraoxadiphosphacyclotridecin-6-yl]imidazo[4,5-d][1,3]oxazin-7(3H)-one

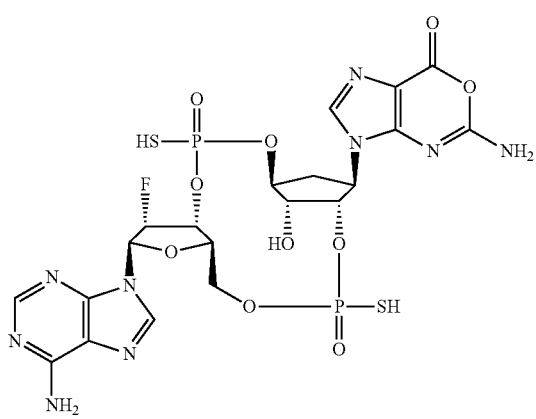 [SMILES: Nc1nc2c(ncn2[C@@H]2C[C@@H]3OP(=O)(S)O[C@H]4[C@@H](F)[C@H](n5cnc6c(N)ncnc65)O[C@@H]4COP(=O)(S)O[C@@H]2[C@@H]3O)c(=O)o1]

Example 9 is made in a similar fashion as Example 1 using N-(7-oxo-3,7-dihydroimidazo[4,5-d][1,3]oxazin-5-yl)benzamide in place of A-2 in step 1 of Scheme A.

Example 10

3-[(4S,6R,7S,1aR,13R,14R,14aR,15R)-13-(6-amino-9H-purin-9-yl)-14-fluoro-15-hydroxy-2,9-dioxido-2,9-disulfanyloctahydro-11H-4,7-methanofuro[3,2-d][1,3,7,9,2,8]tetraoxadiphosphacyclotridecin-6-yl]-3,5-dihydro-9H-imidazo[1,2-a]purin-9-one

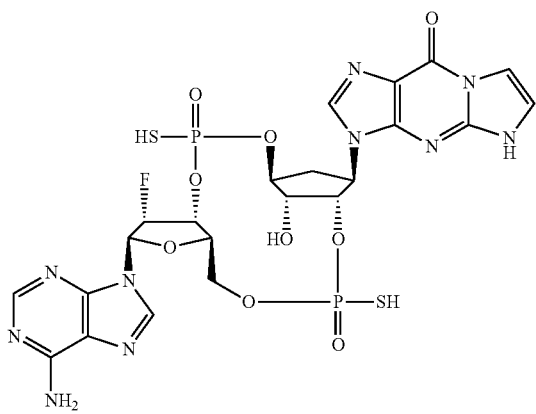 [SMILES: Nc1ncnc2c1ncn2[C@@H]1O[C@@H]2COP(=O)(S)O[C@@H]3[C@H](O)[C@H](C[C@H]3n3cnc4c(=O)n5cc[nH]c5nc43)OP(=O)(S)O[C@H]2[C@H]1F]

Example 10 is made in a similar fashion as Example 1 using N-(6-(benzyloxy)-9H-purin-2-yl)benzamide in place of A-2 in step 1 of Scheme A.

Example 11

(4S,6R,7S,11aR,13R,14R,14aR,15R)-6-(4-amino-3-methoxy-1H-pyrazolo[3,4-d]pyrimidin-1-yl)-13-(6-amino-9H-purin-9-yl)-14-fluoro-2,9-disulfanyloctahydro-11H-4,7-methanofuro[3,2-d][1,3,7,9,2,8]tetraoxadiphosphacyclotridecin-15-ol 2,9-dioxide

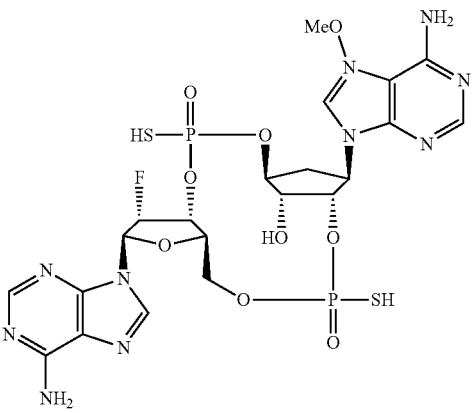

Example 11 is made in a similar fashion as Example 1 using N-(3-methoxy-1H-pyrazolo[3,4-d]pyrimidin-4-yl)benzamide in place of A-2 in step 1 of Scheme A.

Example 12

4-amino-1-[(4S,6R,7S,11aR,13R,14R,14aR,15R)-13-(6-amino-9H-purin-9-yl)-14-fluoro-15-hydroxy-2,9-dioxido-2,9-disulfanyloctahydro-11H-4,7-methanofuro[3,2-d][1,3,7,9,2,8]tetraoxadiphosphacyclotridecin-6-yl]-1,2-dihydro-3H-pyrazolo[3,4-d]pyrimidin-3-one

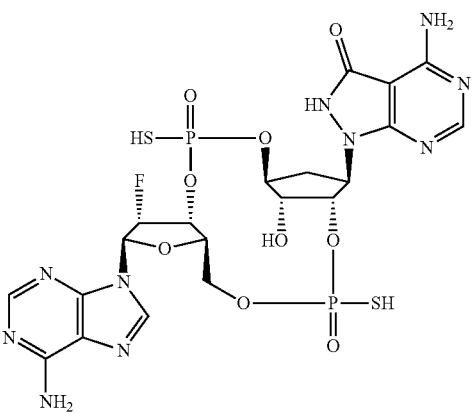 [SMILES: Nc1ncnc2c1ncn2[C@@H]1O[C@@H]2COP(=O)(S)O[C@@H]3[C@H](O)[C@H](C[C@H]3n3[nH]c(=O)c4c(N)ncnc43)OP(=O)(S)O[C@H]2[C@H]1F]

Example 12 is made in a similar fashion as Example 11 using an additional deprotection step after step 5 of Scheme C.

Example 13

(4S,6R,7S,11aS,13R,14R,14aR,15R)-6,13-bis(6-amino-9H-purin-9-yl)-14-fluoro-2-sulfanyloctahydro-11H-4,7-methanofuro[3,2-d][1,3,9,7,2,8]trioxathiadiphosphacyclotridecine-9,15-diol 2,9-dioxide

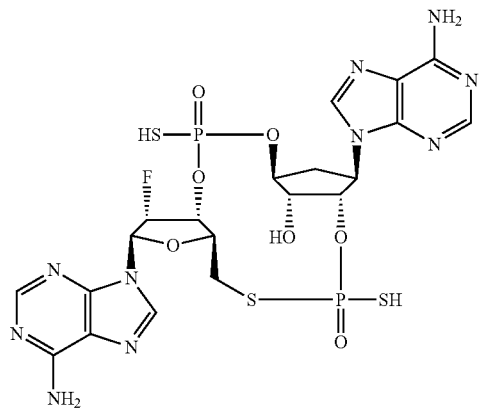 [SMILES: Nc1ncnc2c1ncn2[C@@H]1C[C@@H]2OP(=O)(S)O[C@H]3[C@@H](F)[C@H](n4cnc5c(N)ncnc54)O[C@@H]3CSP(=O)(S)O[C@@H]1[C@@H]2O]

Example 13 was made in a similar fashion as Example 1 using (2S,3R,4R,5R)-5-(6-benzamido-9H-purin-9-yl)-4-fluoro-2-(mercaptomethyl)tetrahydrofuran-3-yl hydrogen phosphonate (H-2, Scheme H) in place of B-4, tetrazole in place of pyridinium triflate (pyTFA), and tBuOOH in place of DDT in step 1 of Scheme C.

Peak 1: 30 mg, 24%; $^1$H NMR (400 MHz, DMSO-d6) δ ppm 8.33 (s, 1H) 8.23 (s, 1H) 8.15 (s, 1H) 8.13 (s, 1H) 6.15-6.26 (m, 1H) 5.66-5.85 (m, 1H) 5.08-5.24 (m, 2H) 4.98-5.07 (m, 1H) 4.77 (t, J=7.40 Hz, 1H) 4.35 (br. s., 2H) 3.42 (d, J=14.31 Hz, 1H) 3.16-3.20 (m, 1H) 2.84 (br. s., 1H) 2.57 (q, J=7.25 Hz, 1H) 1.79 (br. s., 1H); $^{31}$P NMR (162 MHz, DMSO-d6, internal reference H$_3$PO$_4$) δ ppm 51.14 (s, 1P) 9.89 (s, 1P); $^{19}$F NMR (376 MHz, DMSO-d6) δ ppm −194.39 (s, 1F).

Peak 2: 18 mg, 15%; $^1$H NMR (400 MHz, DMSO-d6) δ ppm 8.39 (s, 1H) 8.21 (s, 1H) 8.16 (s, 1H) 8.13 (s, 1H) 6.05-6.26 (m, 2H) 5.12-5.27 (m, 2H) 4.93-5.03 (m, 1H) 4.62 (t, J=6.30 Hz, 1H) 4.31-4.42 (m, 2H) 3.41 (d, J=15.04 Hz, 1H) 3.10 (t, J=11.68 Hz, 1H) 2.85 (br. s., 1H) 1.68 (d, J=5.99 Hz, 1H); $^{31}$P NMR (162 MHz, DMSO-d6 internal reference H$_3$PO$_4$) δ ppm 48.59 (s, 1P) 10.51 (s, 1P); $^{19}$F NMR (376 MHz, DMSO-d6) δ ppm −195.78 (s, 1F).

Scheme H

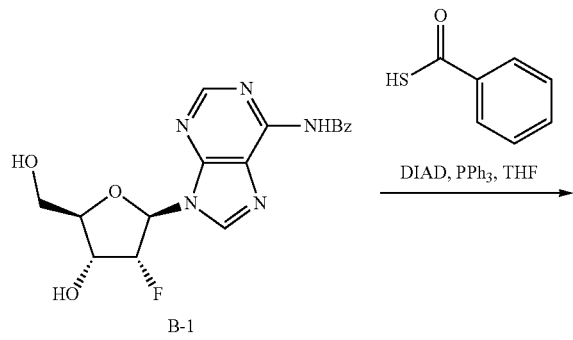

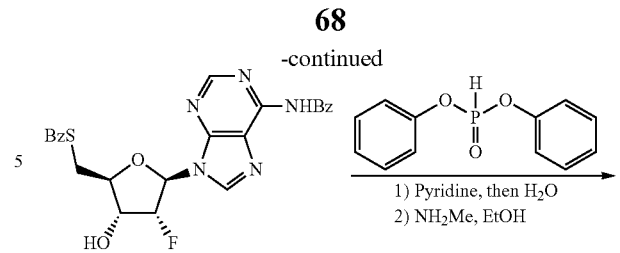

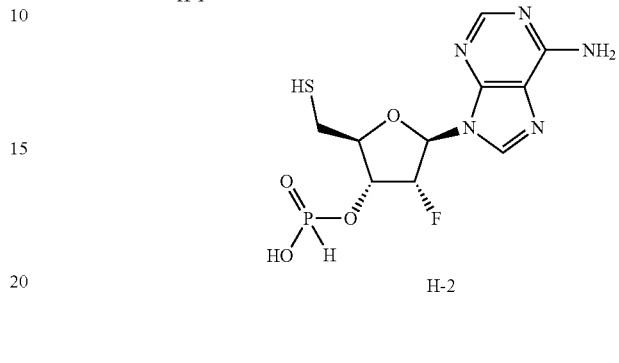

Step 1: Synthesis of N-benzoyl-5'-S-benzoyl-2'-deoxy-2'-fluoro-5'-thioadenosine (H-1)

To a suspension of B-1 (2.00 g, 5.36 mmol) and thiobenzoic acid (1.11 g, 8.04 mmol) in THF (50 mL) was added a solution of DIAD (1.48 mL, 7.50 mmol) and PPh$_3$ (1.97 g, 7.50 mmol) in THF (5 mL). After stirring overnight, the reaction was diluted with EtOAc and washed with water and brine. The organics were dried over MgSO$_4$, filtered and concentrated. The crude residue was purified via flash chromatography (80 g SiO$_2$, Isco, 0-100% EtOAc/heptanes) to afford H-1 (2.1 g, 79%). LCMS [M+H]=494 observed; $^1$H NMR (400 MHz, DMSO-d$_6$) δ ppm=11.21 (br. s., 1H) 8.74 (s, 1H) 8.65 (s, 1H) 7.98-8.10 (m, 2H) 7.83-7.93 (m, 2H) 7.62-7.72 (m, 2H) 7.50-7.61 (m, 4H) 6.39 (dd, J=19.20, 2.20 Hz, 1H) 5.97 (d, J=6.24 Hz, 1H) 5.61-5.79 (m, 1H) 4.61-4.76 (m, 1H) 4.11-4.22 (m, 1H) 3.67 (dd, J=14.06, 4.28 Hz, 1H) 3.44 (dd, J=13.94, 7.21 Hz, 1H)

Step 2: Synthesis of (2S,3R,4R,5R)-5-(6-benzamido-9H-purin-9-yl)-4-fluoro-2-(mercaptomethyl)tetrahydrofuran-3-yl hydrogen phosphonate (H-2)

H-1 (1.00 g, 2.03 mmol) was co-evaporated with anhydrous pyridine (3×) then the residue was dissolved a final time in anhydrous pyridine (20.0 mL). The solution was cooled in an ice-water bath followed by the addition of diphenyl phosphonate (770 uL, 4.05 mmol). The ice-bath was removed and the reaction was stirred for 2.5 hours. Another 1 eq diphenyl phosphonate was added and after 1 hour, the reaction was quenched with 1 M TEAB (gas evolved). Extracted with DCM (4×), dried organics over dried over MgSO$_4$, filtered and concentrated. The residue was dissolved in 33% MeNH$_2$ in EtOH (10 mL). After 30 min, the reaction was concentrated and the crude residue was purified via flash chromatography (40 g SiO$_2$, Isco, 0-100% MeOH/DCM) to afford H-2 (2.1 g, 79%). LCMS [M+H]=350 observed; $^1$H NMR (400 MHz, DMSO-d$_6$) δ ppm=8.35 (s, 1H), 8.16 (s, 1H), 7.36 (s, 2H), 6.24 (dd, J=2.6, 18.2 Hz, 1H), 5.68-5.49 (m, 1H), 4.95-4.81 (m, 1H), 4.16-4.09 (m, 1H), 3.01-2.93 (m, 1H), 2.86 (dd, J=6.1, 14.1 Hz, 1H); $^{31}$P NMR (162 MHz, DMSO-d$_6$) δ ppm=0.28 (s, 1P); $^{19}$F NMR (376 MHz, DMSO-d$_6$) δ ppm=−201.15 (s, 1F).

Example 14

9-[(4S,6R,7S,11aR,13R,14R,14aR,15R)-13-(6-amino-9H-purin-9-yl)-14-fluoro-2,9,15-trihydroxy-2,9-dioxidooctahydro-11H-4,7-methanofuro[3,2-d][1,3,7,9,2,8]tetraoxadiphosphacyclotridecin-6-yl]-1-methyl-1,9-dihydro-6H-purin-6-one

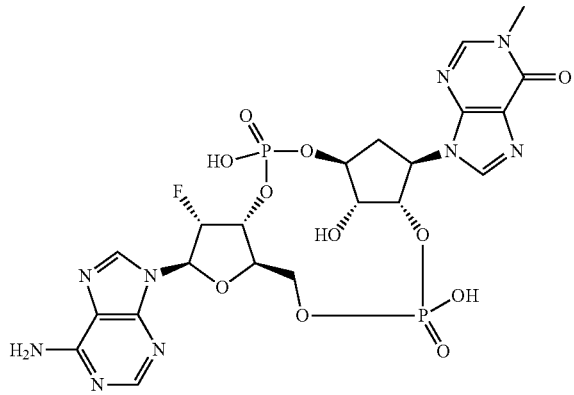 [SMILES: Cn1cnc2c(ncn2[C@@H]2C[C@@H]3OP(=O)(O)O[C@H]4[C@@H](F)[C@H](n5cnc6c(N)ncnc65)O[C@@H]4COP(=O)(O)O[C@@H]2[C@@H]3O)c1=O]

Example 14 was made in a similar fashion as Example 2 using ETT in place of pyTFA, DCM in place of THF, and tBuOOH in place of DDTT in step 1 and iodine in place of 3H-benzodithiol-3-one in step 2 of Scheme E. The crude material was purified by reverse phase chromatography (Phenomenex Luna Omega 5 um Polar column, Mobile phase A: H$_2$O w/10 mM NH$_4$OAc Mobile phase B: MeCN) to give the desired product. (11 mg, 13.8% yield)

$^1$H NMR (400 MHz, DMSO-d6) δ ppm 8.32 (s, 1H), 8.21 (s, 1H), 8.16 (s, 1H), 8.04 (s, 1H), 6.27 (d, J=18.5 Hz, 1H), 5.59-5.39 (m, 1H), 5.15-5.07 (m, 1H), 4.96-4.80 (m, 2H), 4.51-4.48 (m, 1H), 4.31-4.25 (m, 1H), 4.23-4.17 (m, 1H), 4.11-4.05 (m, 2H), 3.46 (s, 3H), 2.90-2.76 (m, 1H), 1.75-1.67 (m, 1H); $^{31}$P NMR (162 MHz, DMSO-d6, internal reference H$_3$PO$_4$) δ ppm −3.42 (s, 1P) −6.58 (s, 1P); $^{19}$F NMR (376 MHz, DMSO-d6) δ ppm −198.30 (s, 1F)

Example 15

9-[(4S,6R,7S,11aR,13R,14R,14aR,15R)-13-(6-amino-9H-purin-9-yl)-14-fluoro-2,15-dihydroxy-2,9-dioxido-9-sulfanyloctahydro-11H-4,7-methanofuro[3,2-d][1,3,7,9,2,8]tetraoxadiphosphacyclotridecin-6-yl]-1-methyl-1,9-dihydro-6H-purin-6-one

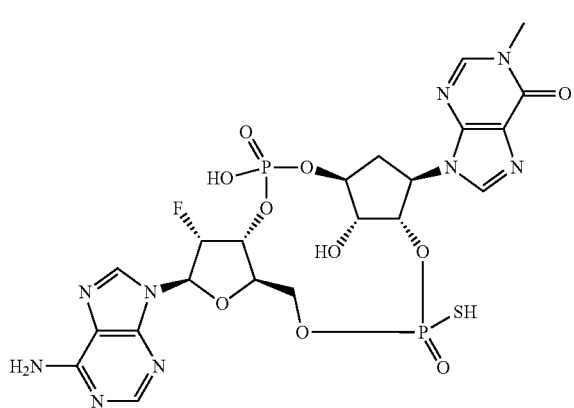

Example 15 was made in a similar fashion as Example 2 using ETT in place of pyTFA and DCM in place of THF in step 1 and iodine in place of 3H-benzodithiol-3-one in step 2 of Scheme E. The crude material was purified by reverse phase chromatography (Phenomenex Gemini NX-C18 3 um column, Mobile phase A: H$_2$O w/10 mM NH$_4$OAc Mobile phase B: MeCN) to give the two diastereomer products.

Peak 1

15 mg, 20% yield $^1$H NMR (400 MHz, D$_2$O) δ ppm 8.49 (s, 1H), 8.33 (s, 1H), 8.21 (s, 1H), 7.80 (s, 1H), 6.55 (d, J=16.0 Hz, 1H), 5.78-5.66 (m, 1H), 5.66-5.60 (m, 2H), 5.18-5.11 (m, 2H), 4.70-4.59 (m, 1H), 4.59-4.54 (m, 1H), 4.43-4.37 (m, 1H), 4.25-4.17 (m, 1H), 3.56 (s, 3H), 3.13-3.03 (m, 1H), 2.31-2.23 (m, 1H); $^{31}$P NMR (162 MHz, DMSO-d6, internal reference H$_3$PO$_4$) δ ppm 53.77 (s, 1P) −6.21 (s, 1P); $^{19}$F NMR (376 MHz, DMSO-d6) δ ppm −198.24 (s, 1F)

Peak 2

27 mg, 29% yield $^1$H NMR (400 MHz, DMSO-d6) δ ppm 8.33 (s, 1H), 8.18 (s, 1H), 8.18 (s, 1H), 8.02 (s, 1H), 6.28 (d, J=18.1 Hz, 1H), 5.55-5.38 (m, 1H), 5.35-5.24 (m, 1H), 4.95-4.86 (m, 2H), 4.86-4.79 (m, 1H), 4.51-4.47 (m, 1H), 4.29-4.22 (m, 2H), 4.12-4.08 (m, 1H), 3.46 (s, 3H), 2.87-2.76 (m, 1H), 1.75-1.71 (m, 1H); $^{31}$P NMR (162 MHz, DMSO-d6, internal reference H$_3$PO$_4$) δ ppm 49.60 (s, 1P) −6.27 (s, 1P); $^{19}$F NMR (376 MHz, DMSO-d6) δ ppm −199.37 (s, 1F)

Example 16

9-[(4S,6R,7S,11aR,13R,14R,14aR,15R)-13-(6-amino-9H-purin-9-yl)-14-fluoro-9,15-dihydroxy-2,9-dioxido-2-sulfanyloctahydro-11H-4,7-methanofuro[3,2-d][1,3,7,9,2,8]tetraoxadiphosphacyclotridecin-6-yl]-1-methyl-1,9-dihydro-6H-purin-6-one

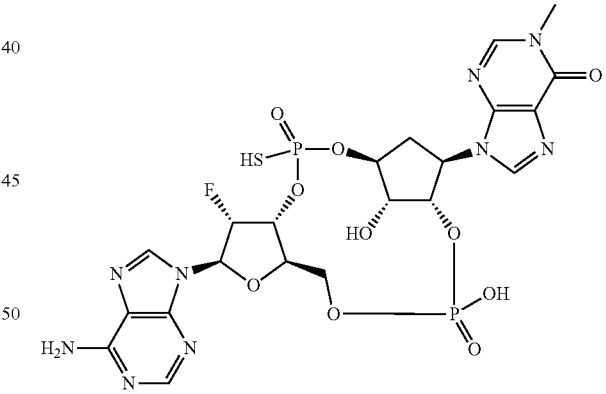

Example 16 was made in a similar fashion as Example 2 using ETT in place of pyTFA, DCM in place of THF, and tBuOOH in place of DDTT in step 1 of Scheme E. The crude material was purified by reverse phase chromatography (Phenomenex Gemini NX-C18 3 um column, Mobile phase A: H$_2$O w/10 mM NH$_4$OAc Mobile phase B: MeCN) to give the two diastereomer products.

Peak 1

11 mg, 8.5% yield $^1$H NMR (400 MHz, D$_2$O) δ ppm 8.36 (s, 1H), 8.33 (s, 1H), 8.19 (s, 1H), 7.71 (s, 1H), 6.53 (d, J=16.4 Hz, 1H), 5.80-5.60 (m, 3H), 5.25-5.11 (m, 2H), 4.68 (m, 1H), 4.59-4.53 (m, 1H), 4.43 (m, 1H), 4.20-4.13 (m, 1H), 3.55 (s, 3H), 3.14-3.02 (m, 1H), 2.26-2.18 (m, 1H); $^{31}$P NMR (162 MHz, DMSO-d6, internal reference H$_3$PO$_4$) δ ppm 50.40 (s, 1P) −3.59 (s, 1P); $^{19}$F NMR (376 MHz, DMSO-d6) ppm −197.41 (s, 1F)

Peak 2

32 mg, 24.3% yield $^1$H NMR (400 MHz, DMSO-d6) δ ppm 8.35 (s, 1H), 8.28 (s, 1H), 8.15 (s, 1H), 8.13 (s, 1H), 6.27 (d, J=17.4 Hz, 1H), 6.20-6.01 (m, 1H), 5.07-4.99 (m, 1H), 4.98-4.83 (m, 2H), 4.48-4.37 (m, 2H), 4.26-4.19 (m, 1H), 4.17-4.09 (m, 1H), 4.08-3.99 (m, 1H), 3.47 (s, 3H), 2.90-2.79 (m, 1H), 1.68-1.60 (m, 1H); $^{31}$P NMR (162 MHz, DMSO-d6, internal reference H$_3$PO$_4$) δ 48.53 (s, 1P) −3.30 (s, 1P); $^{19}$F NMR (376 MHz, DMSO-d6) −198.19 (s, 1F)

Example 17

9-[(4S,6R,7S,11aR,13R,14R,14aR,15R)-13-(6-amino-9H-purin-9-yl)-14-fluoro-15-hydroxy-9-oxido-2,9-disulfanyl-2-sulfidooctahydro-11H-4,7-methanofuro[3,2-d][1,3,7,9,2,8]tetraoxadiphosphacyclotridecin-6-yl]-1-methyl-1,9-dihydro-6H-purin-6-one

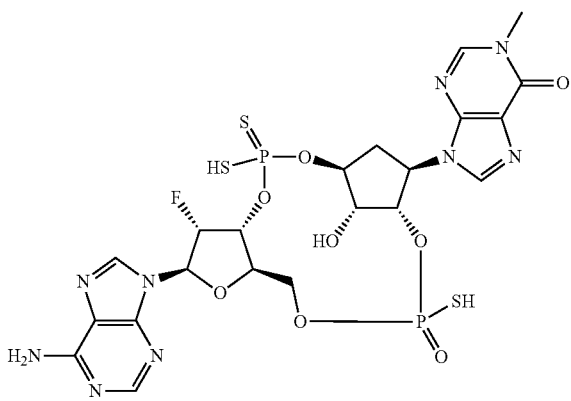

Example 17 was made in a similar fashion as Example 1 using compound I-1 (N-benzoyl-2'-deoxy-2'-fluoro-3'-O-[hydroxy(sulfido)-l$^5$-phosphanyl]adenosine) in place of B-4, ETT in place of pyTFA, DCM in place of THF in step 1 and DPPCI in place of DMOCP in step 2 of Scheme C.

Purification: Phenomenex Gemini NX-C18 3 um column, Mobile phase A: H$_2$O w/10 mM NH$_4$OAc Mobile phase B: MeCN Peak 1

7.4 mg, 7.7% yield $^1$H NMR (400 MHz, D$_2$O) δ ppm 8.51 (s, 1H), 8.33 (s, 1H), 8.21 (s, 1H), 7.74 (s, 1H), 6.56 (d, J=15.6 Hz, 1H), 6.47-6.28 (m, 1H), 5.80-5.69 (m, 1H), 5.40-5.26 (m, 1H), 5.22-5.10 (m, 2H), 4.65-4.62 (m, 1H), 4.62-4.56 (m, 1H), 4.46-4.39 (m, 1H), 4.24-4.16 (m, 1H), 3.52 (s, 3H), 3.17-3.03 (m, 1H), 2.33-2.22 (m, 1H); $^{31}$P NMR (162 MHz, D$_2$O, internal reference H$_3$PO$_4$) δ 108.39 (s, 1P) 56.07 (s, 1P); $^{19}$F NMR (376 MHz, D$_2$O) −199.57 (s, 1F)

Peak 2

9.4 mg, 8.5% yield $^1$H NMR (400 MHz, D$_2$O) δ ppm 8.36 (s, 1H), 8.32 (s, 1H), 8.20 (s, 1H), 7.69 (s, 1H), 6.54 (d, J=16.0 Hz, 1H), 6.46-6.30 (m, 1H), 5.86-5.75 (m, 1H), 5.34-5.20 (m, 2H), 5.16-5.10 (m, 1H), 4.68-4.64 (m, 1H), 4.63-4.58 (m, 1H), 4.53-4.45 (m, 1H), 4.17-4.08 (m, 1H), 3.52 (s, 3H), 3.16-2.99 (m, 1H), 2.27-2.17 (m, 1H); $^{31}$P NMR (162 MHz, D$_2$O, internal reference H$_3$PO$_4$) δ 108.06 (s, 1P) 51.78 (s, 1P); $^{19}$F NMR (376 MHz, D$_2$O) −199.73 (s, 1F)

Compound I-1

N-benzoyl-2'-deoxy-2'-fluoro-3'-O-[hydroxy(sulfido)-l$^5$-phosphanyl]adenosine

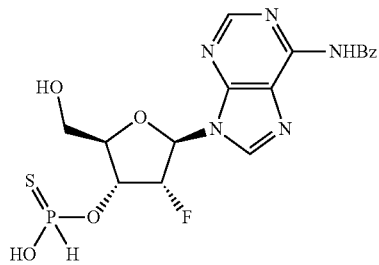

Compound I-1 was made in a similar fashion as example B-4 according to literature proceedures (Jones et al. Nucleosides, Nucleotides and Nucleic Acids 2009, 28, 352-378) using diphenyl phosphonate in place of ditbutyl phosphonate and Li$_2$S in place of water in step 2 of Scheme B.

Example 18

9-((4S,6R,7S,11aR,13R,14R,14aR,15R)-13-(6-amino-9H-purin-9-yl)-14-fluoro-15-hydroxy-2,9-dimercapto-2,9-disulfidooctahydro-11H-4,7-methanofuro[3,2-d][1,3,7,9]tetraoxa[2,8]diphosphacyclotridecin-6-yl)-1-methyl-1,9-dihydro-6H-purin-6-one (J-5)

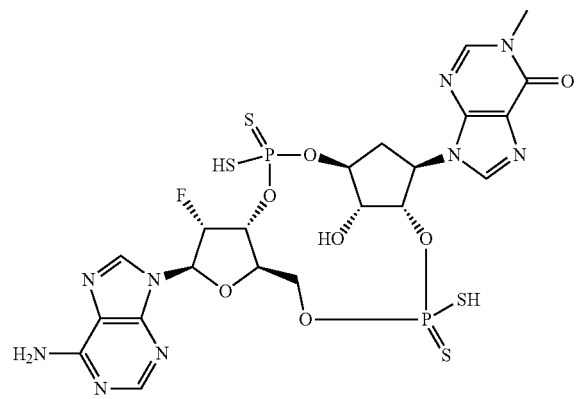 [SMILES: Cn1cnc2c(ncn2[C@@H]2C[C@@H]3OP(=S)(S)O[C@H]4[C@@H](F)[C@H](n5cnc6c(N)ncnc65)O[C@@H]4COP(=S)(S)O[C@@H]2[C@@H]3O)c1=O]

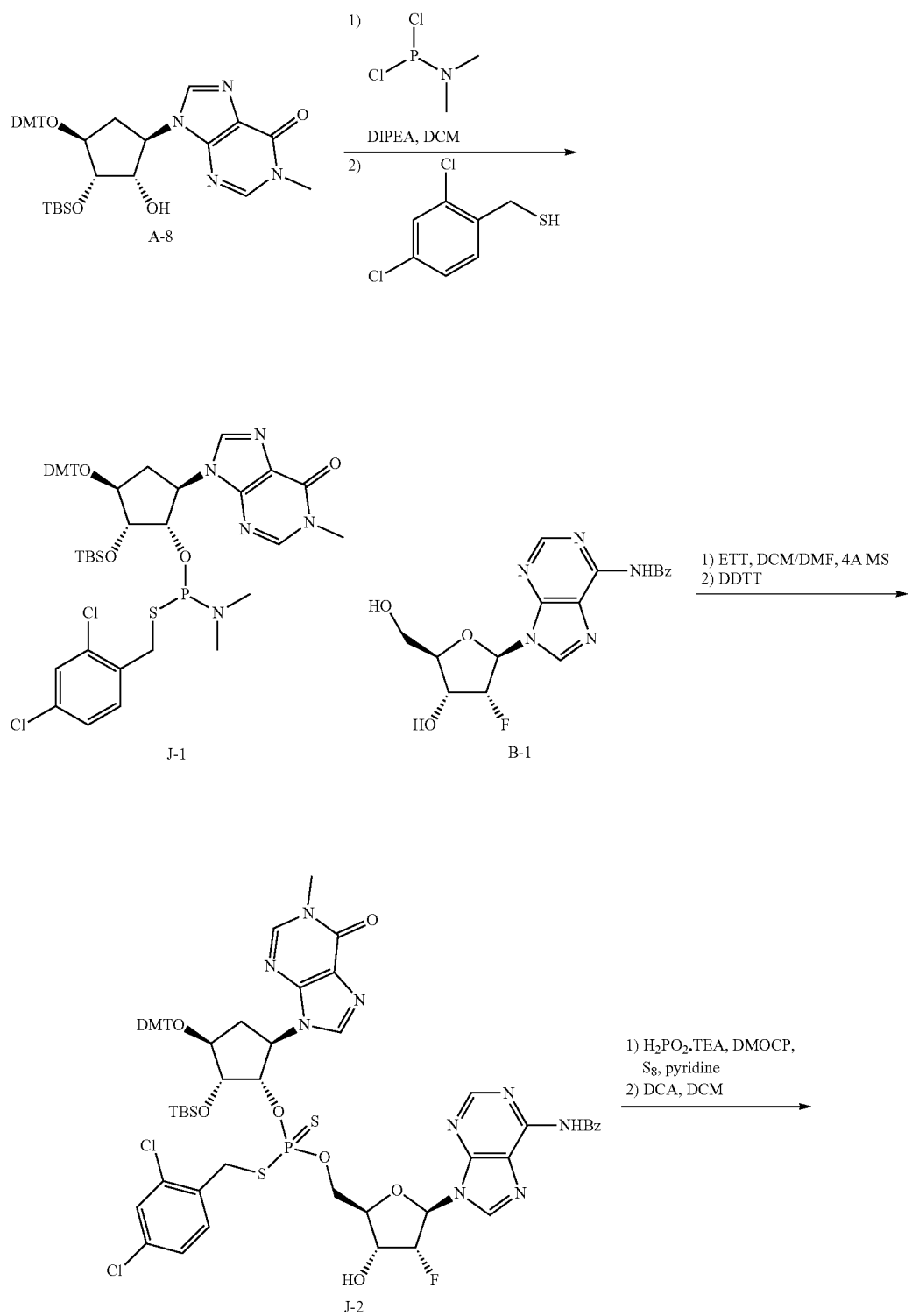

-continued
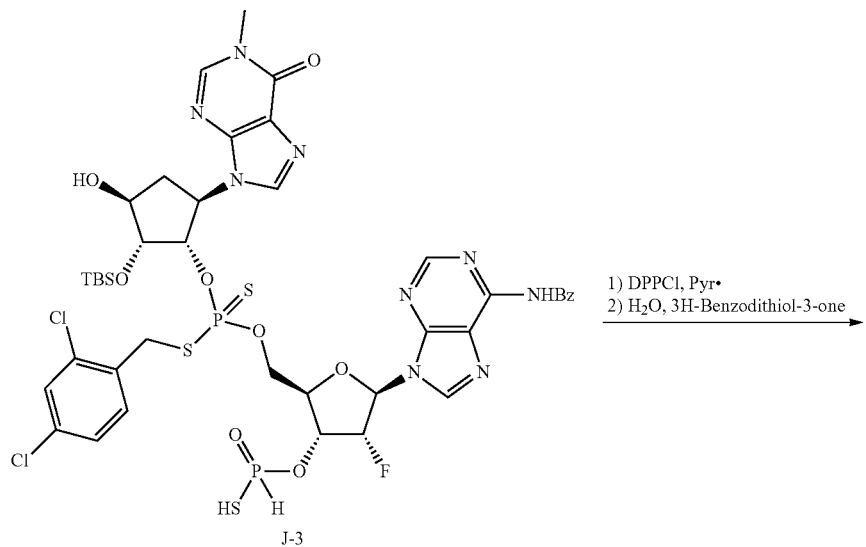
J-3
1) DPPCl, Pyr•
2) H₂O, 3H-Benzodithiol-3-one
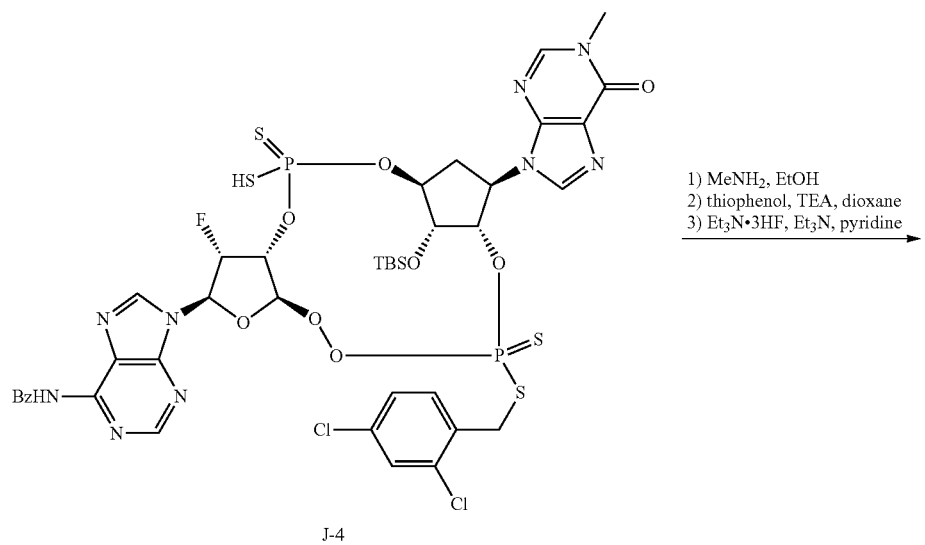
J-4
1) MeNH₂, EtOH
2) thiophenol, TEA, dioxane
3) Et₃N•3HF, Et₃N, pyridine
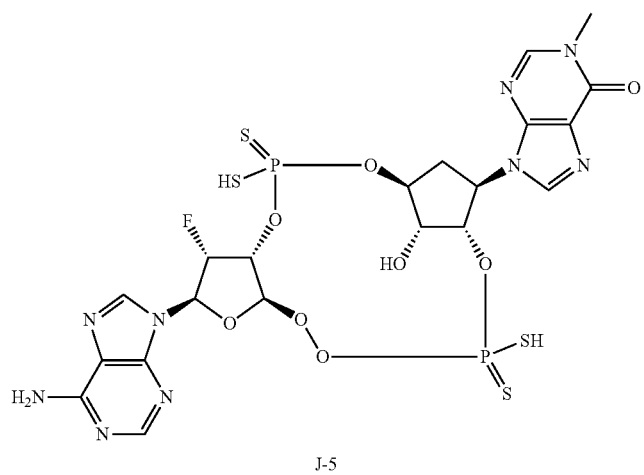
J-5

Step 1: Synthesis of O-[(1 S,2R,3S,5R)-3-[bis(4-methoxyphenyl)(phenyl)methoxy]-2-{[tert-butyl(dimethyl)silyl]oxy}-5-(1-methyl-6-oxo-1,6-dihydro-9H-purin-9-yl)cyclopentyl] S-[(2,4-dichlorophenyl)methyl] N,N-dimethylphosphoramidothioite (J-1)

All solutions contained powdered molecular sieves. To a cooled (ice-water bath) solution of N,N-dimethylphosphoramidous dichloride (0.34 mL, 2.9 mmol) in DCM (10 mL) was added a solution of A-8 (1.0 g, 1.5 mmol) and DIEA (2.0 mL, 12 mmol) in DCM (10 mL). After 1 hr, a solution of (2,4-dichlorophenyl)methanethiol (0.83 mL, 5.9 mmol) in DCM (5 mL) was added and the ice-bath was removed. After 1 hr, the molecular sieves were removed by filtration and the filtrate was concentrated then purified via flash chromatography (40 g SiO$_2$, Isco, 0-100% EtOAc/heptanes) to afford J-1 (790 mg, 57%) as a white solid. $^{31}$P NMR (162 MHz, DMSO-d$_6$) δ ppm=174.1 2, 169.6

Step 2: Synthesis of N-benzoyl-5'-O-(({[(1 S,2R,3S,5R)-3-[bis(4-methoxyphenyl)(phenyl)methoxy]-2-{[tert-butyl(dimethyl)silyl]oxy}-5-(1-methyl-6-oxo-1,6-dihydro-9H-purin-9-yl)cyclopentyl]oxy}{[(2,4-dichlorophenyl)methyl]sulfanyl}phosphorothioyl)oxy){[(2,4-dichlorophenyl)methyl]sulfanyl}phosphorothioyl)-2'-deoxy-2'-fluoroadenosine (J-2)

A mixture of J-1 (1.3 g, 1.3 mmol) and powdered molecular sieves in DCM (13 mL) was stirred for 20 min (flask A). In a separated flask a mixture of B-1 (540 mg, 1.5 mmol), ETT (1.3 g, 9.9 mmol) and powdered molecular sieves in DMF (13 mL) was stirred for 20 min (flask B). The contents of flask B were then added to flask A. After 30 min, DDTT (310 mg, 1.5 mmol) was added. After 15 min, the molecular sieves were removed by filtration and the filtrate was concentrated then purified via flash chromatography (40 g SiO$_2$, Isco, 0-100% EtOAc/heptanes) to afford J-2 (436 mg, not pure). LCMS [M+H]=1308 observed; $^{31}$P NMR (162 MHz, DMSO-d$_6$) b ppm=95.8, 94.3; $^{19}$F NMR (376 MHz, DMSO-d$_6$) δ ppm=201.49, 201.51

Step 3: Synthesis of O-((2R,3R,4R,5R)-5-(6-benzamido-9H-purin-9-yl)-2-((((((1S,2R,3S,5R)-2-((tert-butyldimethylsilyl)oxy)-3-hydroxy-5-(1-methyl-6-oxo-1,6-dihydro-9H-purin-9-yl)cyclopentyl)oxy)((2,4-dichlorobenzyl)thio)phosphorothioyl)oxy)methyl)-4-fluorotetrahydrofuran-3-yl) S-hydrogen phosphonothioate (J-3)

A mixture of J-2 (180 mg, 0.14 mmol, not pure) sulfur (13 mg, 0.42 mmol) and N,N-diethylethanaminium phosphinate (0.120 mL, 0.83 mmol) was co-evaporated with pyridine. The residue was dissolved in pyridine (1.4 mL) then DMOCP (77 mg, 0.42 mmol) was added. After ~1 hr, the reaction was diluted with EtOAc, washed with water and brine and concentrated. To the residue was added DCM (2 mL) followed by dichloroacetic acid (120 uL) resulting in a bright orange solution. After 15 min, quenched with pyridine until orange color dissipated, concentrated and purified via flash chromatography (12 g SiO$_2$, Isco, 0-30% MeOH/DCM) to afford J-3 (64 mg). LCMS [M+H]=1086 observed; $^{31}$P NMR (162 MHz, DMSO-d$_6$) δ ppm=96.9, 94.2, 49.4; 48.7; $^{19}$F NMR (376 MHz, DMSO-d$_6$) δ ppm=199.6, 199.7, 199.8, 200.1

Step 4: Synthesis of N-(9-((4S,6R,7S,11aR,13R,14R,14aR,15R)-15-((tert-butyldimethylsilyl)oxy)-9-((2,4-dichlorobenzyl)thio)-14-fluoro-2-mercapto-6-(1-methyl-6-oxo-1,6-dihydro-9H-purin-9-yl)-2,9-disulfidooctahydro-11H-4,7-methanofuro[3,2-d][1,3,7,9]tetraoxa[2,8]diphosphacyclotridecin-13-yl)-9H-purin-6-yl)benzamide (J-4)

J-4 was made in a similar fashion as C-2 using DPPCI in place of DMOCP. LCMS [M+H]=1100 observed; $^{31}$P NMR (162 MHz, DMSO-d$_6$) δ ppm=110.4, 110.3, 97.1, 95.5; $^{19}$F NMR (376 MHz, DMSO-d$_6$) δ ppm=196.0, 196.5

Step 5: Synthesis of 9-((4S,6R,7S,11aR,13R,14R,14aR,15R)-13-(6-amino-9H-purin-9-yl)-14-fluoro-15-hydroxy-2,9-dimercapto-2,9-disulfidooctahydro-11H-4,7-methanofuro[3,2-d][1,3,7,9]tetraoxa[2,8]diphosphacyclotridecin-6-yl)-1-methyl-1,9-dihydro-6H-purin-6-one (J-5)

To a flask containing J-4 (24 mg, 0.022 mmol) was added a 1:1 solution (0.5 mL) of ACN and 33% methyl amine in EtOH. After 3 hrs, the reaction was concentrated and the residue was dissolved in a 1:1:2 solution (0.2 mL) of thiophenol, TEA, and dioxane. After 5 hrs, the reaction was concentrated. To the residue was added a 1:1 solution (0.4 mL) of TEA:pyridine followed by triethylamine trihydrofluoride (150 uL). The reaction was heated to 70° C. for 12 hrs then quenched with saturated solution of sodium bicarbonate and concentrated. The residue was triturated with 10% MeOH/DCM then Et$_2$O (2×) then purified by reverse phase prep-HPLC [Phenomenex Gemini NX-C18 5 um 21×150 mm column eluting with 0-80% MeCN/H$_2$O containing NH$_4$HCO$_3$ (10 mM)] to give 5 mg of J-5.
$^1$H NMR (400 MHz, DMSO-d6) δ ppm 8.54 (s, 1H) 8.19 (s, 1H) 8.17 (s, 1H) 8.04 (s, 1H) 6.30 (d, J=16.02 Hz, 1H) 6.03-6.20 (m, 1H) 5.24-5.35 (m, 1H) 4.94-5.10 (m, 2H) 4.75-4.81 (m, 1H) 4.36-4.40 (m, 1H) 4.29-4.35 (m, 1H) 4.17-4.25 (m, 1H) 3.88-3.95 (m, 1H) 3.49 (s, 3H) 2.80-2.91 (m, 1H) 1.61-1.68 (m, 1H); $^{31}$P NMR (162 MHz, DMSO-d6) δ ppm 113.20, 110.74; $^{19}$F NMR (376 MHz, DMSO-d6) δ ppm −198.74 LCMS [M+H]=724 observed

Example 19

9,9'-((4S,6R,7S,11aR,13R,14R,14aR,15R)-14-fluoro-15-hydroxy-2,9-dimercapto-2,9-dioxidooctahydro-11H-4,7-methanofuro[3,2-d][1,3,7,9]tetraoxa[2,8]diphosphacyclotridecine-6,13-diyl)bis(1-methyl-1,9-dihydro-6H-purin-6-one

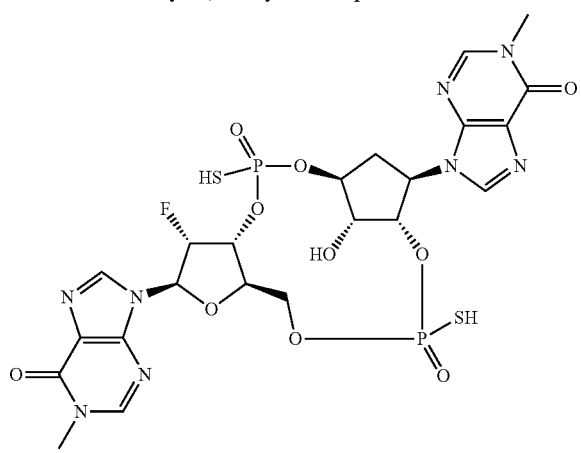

Example 19 was made in a similar fashion as Example 17 using (2R,3R,4R,5R)-4-fluoro-2-(hydroxymethyl)-5-(1-methyl-6-oxo-1,6-dihydro-9H-purin-9-yl)tetrahydrofuran-3-yl hydrogen phosphonate K-4 in place of B-4. The crude material was purified by reverse phase chromatography (Phenomenex Luna Omega 5 um Polar C18 4.6×50 mm column; Mobile phase A: H2O w/10 mM NH4OAc, Mobile phase B: MeCN; elution with a gradient of 0-10% B in 2.0 minutes, then ramp 10-80% at 5.5 min, hold 80% for 0.5 minutes then re-equilibrate; Flow 2.25 mL/min) to give the four diastereomer products.

Peak 1:38 mg, 10.6%; $^1$H NMR (400 MHz, DMSO-d6) δ ppm 8.45 (s, 1H) 8.26 (s, 1H) 8.18 (s, 1H) 8.16 (s, 1H) 6.27 (d, J=18.58 Hz, 1H) 5.51-5.68 (m, 1H) 5.48 (d, J=2.57 Hz, 1H) 5.01-5.10 (m, 1H) 4.95 (td, J=9.75, 5.69 Hz, 2H) 4.60 (br. s., 1H) 4.55 (t, J=5.62 Hz, 1H) 4.20 (br. s., 1H) 3.95-4.02 (m, 1H) 3.86-3.94 (m, 1H) 3.52 (s, 3H) 3.51 (s, 3H) 2.82 (d, J=11.62 Hz, 1H) 1.69-1.75 (m, 1H); $^{31}$P NMR (162 MHz, DMSO-d6) δ ppm 53.70 (s, 1P) 49.98 (s, 1P); $^{19}$F NMR (376 MHz, DMSO-d6) δ ppm −196.72 (s., 1F); LCMS [M+H]=707.0.

Peak 2: 35 mg, 9.3%; $^1$H NMR (400 MHz, DMSO-d6) δ ppm 8.44 (s, 1H) 8.27 (s, 1H) 8.22 (s, 1H) 8.21 (s, 1H) 6.10-6.26 (m, 2H) 4.89-5.06 (m, 3H) 4.61 (br. s., 1H) 4.44 (t, J=5.32 Hz, 1H) 4.20 (d, J=8.80 Hz, 1H) 3.97 (d, J=2.32 Hz, 2H) 3.52 (s, 3H) 3.51 (s, 3H) 2.75-2.84 (m, 1H) 1.67 (dd, J=14.73, 5.07 Hz, 1H); $^{31}$P NMR (162 MHz, DMSO-d6) δ ppm 53.60 (br. s., 1P) 48.19 (br. s., 1P); $^{19}$F NMR (376 MHz, DMSO-d6) δ ppm −197.17 (s., 1F); LCMS [M+H]=707.0.

Peak 3: 8 mg, 2%; $^1$H NMR (400 MHz, DMSO-d6) δ ppm 8.47 (s, 1H) 8.24 (s, 1H) 8.21 (s, 1H) 8.10 (s, 1H) 6.52 (s, 1H) 6.26 (d, J=17.61 Hz, 1H) 5.45-5.65 (m, 1H) 5.12-5.25 (m, 2H) 4.81-4.97 (m, 2H) 4.51 (t, J=6.30 Hz, 1H) 4.45 (br. s., 1H) 4.23 (d, J=8.56 Hz, 1H) 3.98-4.13 (m, 2H) 3.53 (s, 3H) 3.50 (s, 3H) 2.74-2.87 (m, 1H) 1.67 (dd, J=14.67, 6.11 Hz, 1H); $^{31}$P NMR (162 MHz, DMSO-d6) δ ppm 50.04 (s, 1P) 48.32 (br. s., 1P); $^{19}$F NMR (376 MHz, DMSO-d6) δ ppm −198.02 (s., 1F); LCMS [M+H]=707.0.

Peak 4: 40 mg, 10.9%; $^1$H NMR (400 MHz, DMSO-d6) δ ppm 8.46 (s, 1H) 8.32 (s, 1H) 8.24 (s, 1H) 8.16 (s, 1H) 6.27 (d, J=17.48 Hz, 1H) 6.07-6.23 (m, 1H) 5.19 (td, J=9.51, 2.63 Hz, 1H) 4.81-4.96 (m, 3H) 4.45 (br. s., 1H) 4.40 (t, J=5.62 Hz, 1H) 4.24 (d, J=9.41 Hz, 1H) 4.12 (d, J=11.98 Hz, 1H) 4.01 (dd, J=11.68, 5.32 Hz, 1H) 3.53 (s, 3H) 3.50 (s, 3H) 2.81 (d, J=7.46 Hz, 1H) 1.61 (dd, J=14.55, 6.24 Hz, 2H); $^{31}$P NMR (162 MHz, DMSO-d6) δ ppm 49.20 (br. s., 1P) 48.19 (br. s., 1P); $^{19}$F NMR (376 MHz, DMSO-d6) δ ppm −198.36 (s., 1F); LCMS [M+H]=707.0.

Scheme K

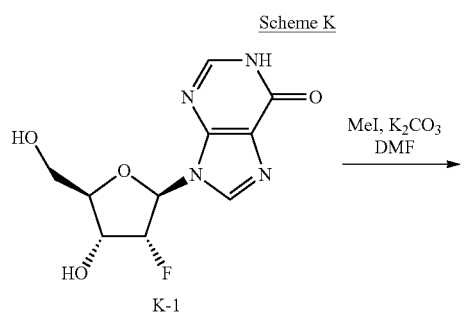

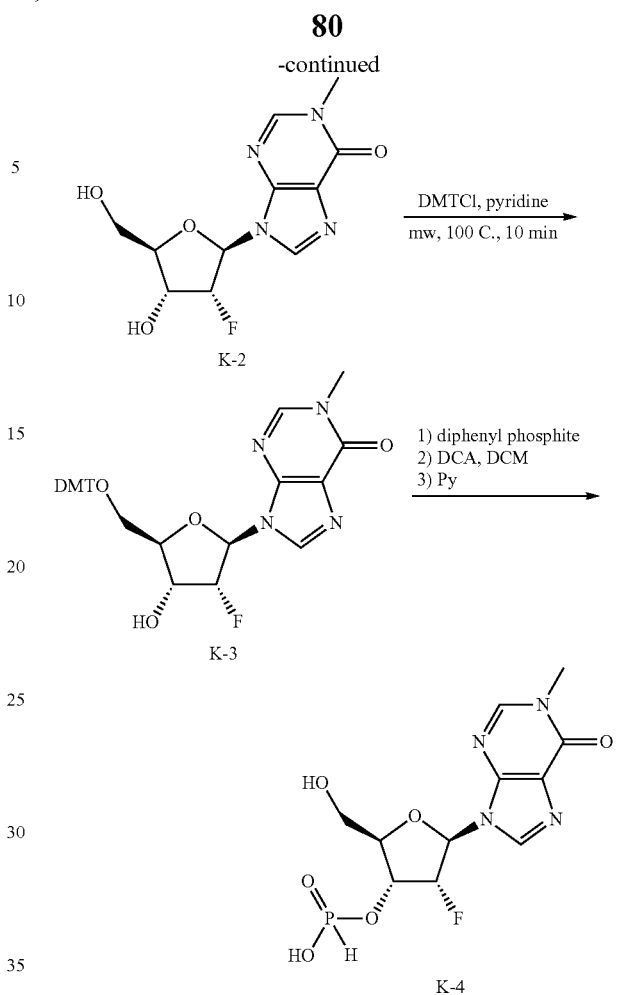

Step 1: Synthesis of 2'-deoxy-2'-fluoro-1-methylinosine (K-2)

Compound K-2 was made in a similar fashion as D-4 using 2'-deoxy-2'-fluoroinosine (K-1) in place of D-3 in step 3 of Scheme D in 98% yield.

$^1$H NMR (400 MHz, DMSO-d6) δ ppm 8.44 (s, 1H) 8.35 (s, 1H) 6.21 (dd, J=16.75, 2.69 Hz, 1H) 5.73 (d, J=6.11 Hz, 1H) 5.25-5.47 (m, 1H) 5.14 (t, J=5.44 Hz, 1H) 4.36-4.52 (m, 1H) 3.93-4.04 (m, 1H) 3.75 (ddd, J=12.32, 5.17, 2.81 Hz, 1H) 3.59 (ddd, J=12.32, 5.65, 4.03 Hz, 1H) 3.52 (s, 3H); 19F NMR (376 MHz, DMSO-d6) δ ppm −204.63 (s, 1F); LCMS [M+H]=285.1.

Step 2: Synthesis of 5'-O-[bis(4-methoxyphenyl)(phenyl)methyl]-2'-deoxy-2'-fluoro-1-methylinosine (K-3)

Compound K-3 was made in a similar fashion as B-2 using microwave at 100° C. for 10 min instead of 25° C. for 12 h in step 1 of Scheme B in 60% yield.

$^1$H NMR (400 MHz, DMSO-d6) δ ppm 8.39 (s, 1H) 8.24 (s, 1H) 7.29-7.36 (m, 2H) 7.15-7.28 (m, 7H) 6.81 (dd, J=8.86, 7.64 Hz, 4H) 6.27 (dd, J=19.44, 1.47 Hz, 1H) 5.72 (d, J=6.85 Hz, 1H) 5.38-5.59 (m, 1H) 4.55-4.72 (m, 1H) 4.10 (dt, J=7.76, 3.94 Hz, 1H) 3.72 (d, J=1.71 Hz, 6H) 3.51 (s, 3H) 3.20-3.28 (m, 2H); $^{19}$F NMR (376 MHz, DMSO-d6) δ ppm −199.30 (s, 1F); LCMS [M+H]=587.2.

Step 3: Synthesis of (2R,3R,4R,5R)-4-fluoro-2-(hydroxymethyl)-5-(1-methyl-6-oxo-1,6-dihydro-9H-purin-9-yl)tetrahydrofuran-3-yl hydrogen phosphonate (K-4)

K-3 (1.28 g, 2.19 mmol) was co-evaporated with anhydrous pyridine (3×) then the residue was dissolved a final time in anhydrous pyridine (22.0 mL). The solution was added dropwise to a solution of diphenyl phosphonate (3.6 g, 15.4 mmol) in anhydrous pyridine (22.0 mL) in an oven dried flask. The reaction was stirred at rt for 15 min under $N_2$, triethylamine-water (12 mL, 1:1, v/v) was added, continued to stir at rt for 15 min, The reaction mixture was concentrated by vacuum, dissolved in DCM (22.0 mL), DCA (5.66 g, 43.9 mmol) was added, stirred at rt for 15 min, then quenched by pyridine (22.0 mL). The reaction was concentrated, purified via flash chromatography (40 g $SiO_2$, Isco, 50% MeOH/DCM) to afford K-4 (0.71 g, 93%) as 0.8 eq. $Et_3N$ salt.

$^1$H NMR (400 MHz, DMSO-d6) δ ppm 8.60 (br. s., 1H) 8.44 (s, 1H) 8.34 (s, 1H) 7.84 (t, J=7.58 Hz, 0.36H) 7.61 (s, 0.5H) 7.38-7.49 (m, 0.75H) 6.25 (d, J=15.89 Hz, 1H) 6.01 (s, 0.5H) 5.75 (s, 0.2H) 5.43-5.66 (m, 1H) 4.92-5.09 (m, 1H) 4.14 (br. s., 1H) 3.75 (d, J=11.13 Hz, 1H) 3.64 (d, J=12.72 Hz, 1H) 3.51 (br. s., 3H) 3.04-3.13 (m, 1.7H) 1.17 (t, J=7.15 Hz, 2.5H); $^{31}$P NMR (162 MHz, DMSO-d6) δ ppm 1.88 (br. s., 1P); $^{19}$F NMR (376 MHz, DMSO-d6) δ ppm −200.26 (br. s., 1F). LCMS [M+H]=350 observed; LCMS [M+H]=349.0.

Example 20

9,9'-((4S,6R,7S,11aR,13R,14R,14aR,15R)-14-fluoro-2,15-dihydroxy-9-mercapto-2,9-dioxidooctahydro-11H-4,7-methanofuro[3,2-d][1,3,7,9]tetraoxa[2,8]diphosphacyclotridecine-6,13-diyl)bis(1-methyl-1,9-dihydro-6H-purin-6-one)

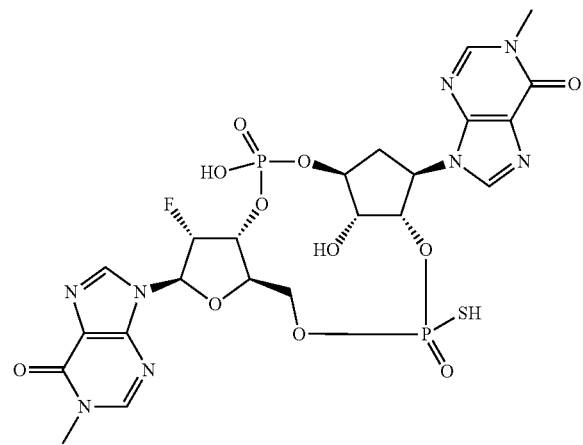 [SMILES: Cn1cnc2c(ncn2[C@@H]2C[C@@H]3OP(=O)(S)O[C@H]4[C@@H](F)[C@H](n5cnc6c(=O)n(C)cnc65)O[C@@H]4COP(=O)(S)O[C@@H]2[C@@H]3O)c1=O]

Example 20 was made in a similar fashion as Example 15. The crude material was purified by reverse phase chromatography (Phenomenex Gemini NX-C18 4.6×50 mm 5 um column; Mobile phase A: H2O w/10 mM NH4OAc, Mobile phase B: MeCN; elution with a gradient of 0-80% B in 5.0 minutes, hold 80% for 0.5 minutes then re-equilibrate; Flow 2.25 mL/min) to give the two diastereomer products.

Peak 1:33 mg, 23%; $^1$H NMR (400 MHz, DMSO-d6) δ ppm 8.44 (s, 1H) 8.27 (s, 1H) 8.21 (s, 1H) 8.15 (s, 1H) 6.25 (d, J=18.58 Hz, 1H) 5.43-5.67 (m, 2H) 4.99-5.07 (m, 1H) 4.89-4.98 (m, 1H) 4.76-4.88 (m, 1H) 4.68 (br. s., 1H) 4.26 (br. s., 1H) 4.17 (br. s., 1H) 3.95-4.03 (m, 1H) 3.87-3.95 (m, 1H) 3.52 (s, 3H) 3.52 (s, 3H) 2.76 (br. s., 1H) 1.67 (dd, J=14.79, 5.38 Hz, 1H); $^{31}$P NMR (162 MHz, DMSO-d6) δ ppm 53.57 (s, 1P) −5.78 (br. s., 1P); $^{19}$F NMR (376 MHz, DMSO-d6) δ ppm −197.49 (br. s., 1F); LCMS [M+H]=691.0.

Peak 2: 33 mg, 23%; $^1$H NMR (400 MHz, DMSO-d6) δ ppm 8.47 (s, 1H) 8.25 (s, 1H) 8.24 (s, 1H) 8.15 (s, 1H) 7.11 (br. s., 2H) 6.52 (s, 3H) 6.25 (d, J=17.36 Hz, 1H) 5.42-5.62 (m, 1H) 5.19 (d, J=3.42 Hz, 2H) 4.88 (td, J=9.96, 6.36 Hz, 1H) 4.68-4.81 (m, 1H) 4.52 (br. s., 1H) 4.17-4.27 (m, 2H) 3.97-4.14 (m, 2H) 3.53 (s, 3H) 3.51 (s, 3H) 2.72-2.84 (m, 1H) 1.61 (dd, J=14.49, 6.05 Hz, 1H); $^{31}$P NMR (162 MHz, DMSO-d6) δ ppm 48.70 (br. s., 1P) −5.56 (br. s., 1P); $^{19}$F NMR (376 MHz, DMSO-d6) δ ppm −196.64 (br. s., 1F); LCMS [M+H]=691.0.

Example 21

9,9'-((4S,6R,7S,11aR,13R,14R,14aR,15R)-14-fluoro-9,15-dihydroxy-2-mercapto-2,9-dioxidooctahydro-11H-4,7-methanofuro[3,2-d][1,3,7,9]tetraoxa[2,8]diphosphacyclotridecine-6,13-diyl)bis(1-methyl-1,9-dihydro-6H-purin-6-one)

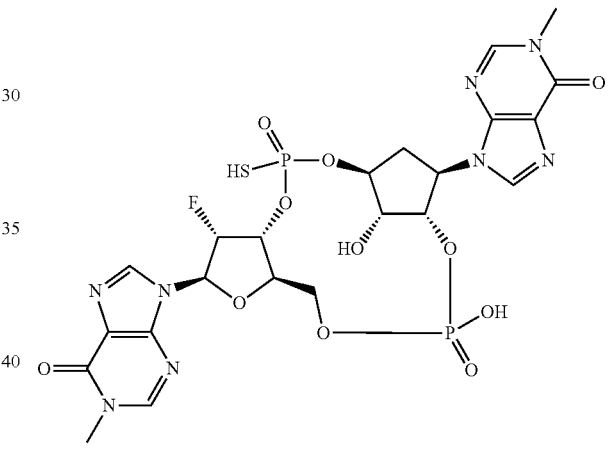

Example 21 was made in a similar fashion as Example 16. The crude material was purified by reverse phase chromatography (Phenomenex Gemini NX-C18 3 um 4.6×50 mm column; Mobile phase A: H2O w/10 mM NH4OAc, Mobile phase B: MeCN; elution with a gradient of 0-80% B in 5.0 minutes, hold 80% for 0.5 minutes then re-equilibrate; Flow 2.25 mL/min) to give the two diastereomer products.

Peak 1: 7.8 mg, 20%; $^1$H NMR (400 MHz, DMSO-d6) δ ppm 8.38 (s, 1H) 8.31 (s, 1H) 8.21 (s, 2H) 6.10-6.30 (m, 2H) 5.83 (br. s., 1H) 4.88 (br. s., 3H) 4.47 (d, J=9.54 Hz, 2H) 4.16 (d, J=9.17 Hz, 1H) 3.96-4.11 (m, 2H) 3.52 (s., 3H) 3.51 (s., 3H) 2.80 (m, 1H) 1.67 (m, 1H); $^{31}$P NMR (162 MHz, DMSO-d6) δ ppm 47.81 (s, 1P) −3.08 (br. s., 1P); $^{19}$F NMR (376 MHz, DMSO-d6) δ ppm −200.26 (br. s., 1F); LCMS [M+H]=691.0.

Peak 2: 4 mg; 10%; $^1$H NMR (400 MHz, DMSO-d6) δ ppm 8.38 (s, 1H) 8.19 (s, 2H) 8.15 (s, 1H) 6.24 (d, J=18.22 Hz, 1H) 5.78 (d, J=2.69 Hz, 1H) 5.49-5.65 (m, 1H) 4.80-4.92 (m, 3H) 4.55 (s, 1H) 4.48 (br. s., 1H) 4.15 (d, J=8.44 Hz, 1H) 4.08 (d, J=12.35 Hz, 1H) 3.97 (d, J=8.68 Hz, 1H) 3.52 (s, 3H) 3.51 (s, 3H) 2.78 (m, 1H) 1.72 (d, J=11.13 Hz, 1H); $^{31}$P NMR (162 MHz, DMSO-d6) δ ppm 49.78 (s, 1P) −3.06 (s, 1P); $^{19}$F NMR (376 MHz, DMSO-d6) δ ppm −195.17 (s, 1F); LCMS [M+H]=691.0.

Example 22

9,9'-((4S,6R,7S,11aR,13R,14R,14aR,15R)-14-fluoro-2,9,15-trihydroxy-2,9-dioxidooctahydro-11H-4,7-methanofuro[3,2-d][1,3,7,9]tetraoxa[2,8]diphosphacyclotridecine-6,13-diyl)bis(1-methyl-1,9-dihydro-6H-purin-6-one)

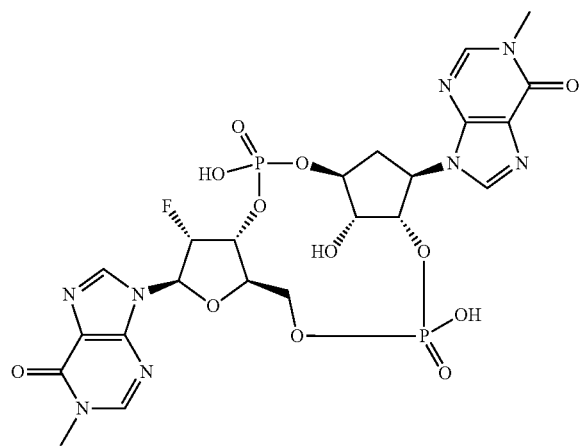 [SMILES: Cn1cnc2c(ncn2[C@@H]2C[C@@H]3OP(=O)(O)O[C@H]4[C@@H](F)[C@H](n5cnc6c(=O)n(C)cnc65)O[C@@H]4COP(=O)(O)O[C@@H]2[C@@H]3O)c1=O]

Example 22 was made in a similar fashion as Example 14 using the H-phosphonate K-4 in place of B-4. The crude material was purified by reverse phase chromatography (Phenomenex Gemini NX-C18 3 um 4.6×50 mm column; Mobile phase A: H2O w/10 mM NH4OAc, Mobile phase B: MeCN; elution with a gradient of 0-80% B in 5.0 minutes, hold 80% for 0.5 minutes, then re-equilibrate; Flow 2.25 mL/min) to give the desired product.

$^1$H NMR (400 MHz, DMSO-d6) δ ppm 8.40 (s, 1H) 8.21 (s, 1H) 8.21 (s, 1H) 8.19 (s, 1H) 6.24 (d, J=17.97 Hz, 1H) 5.74 (br. s., 1H) 5.44-5.64 (m, 1H) 4.83-4.96 (m, 2H) 4.66-4.81 (m, 1H) 4.57 (br. s., 1H) 4.27 (d, J=4.77 Hz, 1H) 4.06-4.18 (m, 2H) 3.96-4.04 (m, 1H) 3.52 (s, 3H) 3.52 (s, 3H) 2.71-2.82 (m, 1H) 1.67 (dd, J=13.94, 5.26 Hz, 1H); $^{31}$P NMR (162 MHz, DMSO-d6) δ ppm −3.03 (s, 1P) −5.74 (br. s., 1P); $^{19}$F NMR (376 MHz, DMSO-d6) δ ppm −196.01 (br. s., 1F); LCMS [M+H]=675.0.

Example 23

(4S,6R,7S,11aR,13R,14R,14aR,15R)-6,13-bis(6-amino-9H-purin-9-yl)-14-fluoro-2,9,15-trihydroxyoctahydro-11H-4,7-methanofuro[3,2-d][1,3,7,9]tetraoxa[2,8]diphosphacyclotridecine 2,9-dioxide

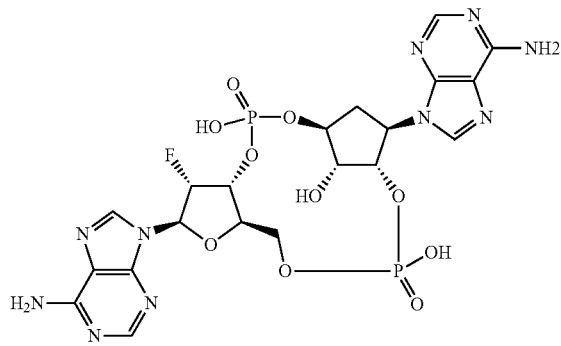 [SMILES: Nc1ncnc2c1ncn2[C@@H]1C[C@@H]2OP(=O)(O)O[C@H]3[C@@H](F)[C@H](n4cnc5c(N)ncnc54)O[C@@H]3COP(=O)(O)O[C@@H]1[C@@H]2O]

Example 23 was made in a similar fashion as Example 14 using the phosphoramidite A-7 in place of D-8. The crude material was purified by reverse phase chromatography using an Agela Durashell C18 25×150 mm column eluting with 0-10% MeCN/H2O containing NH4CO3 (10 mM). LCMS TOF (ESI+) [M+H]$^+$=645 observed; 1H NMR (400 MHz, D2O) δ ppm=8.31-8.24 (m, 3H), 7.86 (s, 1H), 6.47 (d, J=16.8 Hz, 1H), 5.76-5.55 (m, 1H), 5.42-5.29 (m, 1H), 5.22-5.12 (m, 1H), 5.10-4.97 (m, 1H), 4.68 (d, J=0.8 Hz, 1H), 4.52 (d, J=7.0 Hz, 2H), 4.37 (d, J=12.3 Hz, 1H), 4.13 (dd, J=5.5, 12.3 Hz, 1H), 3.12-2.98 (m, 1H), 2.21 (dd, J=4.9, 15.4 Hz, 1H); $^{31}$P NMR (162 MHz, D2O) δ ppm=−4.21 (s, 2P); $^{19}$F NMR (376 MHz, D2O) δ ppm=−200.68 (br s, 1F).

Biological Examples

Biochemical Assay Methods

Surface Plasmon Resonance (SPR) Binding

Surface plasmon resonance (SPR) STING agonist binding studies were carried out using a Biacore T200 instrument (GE Healthcare) at 4° C. in a 150 mM KCl, 25 mM Hepes (pH 7.5), 1 mM TCEP, 2.5 mM MgCl2, 5% (v/v) glycerol, 0.005% (v/v) P20, 1% (v/v) DMSO running buffer. The recombinant protein immobilized on the streptavidin chip was either human WT or H232R STING. A truncated construct of STING was used in all studies. The STING constructs were comprised of residues 155-341 with both N- and C-terminal truncations; the N-terminal transmembrane domains were removed (1-154), as well as the C-terminal tail (342-379). A highly specific N-terminal biotinylation was achieved enzymatically with the E. coli biotin ligase (BirA) and inclusion of the high-affinity biotinylation peptide AviTag™. A Carboxymethylated dextran pre-immobilized with streptavidin (series S Streptavidin CM5 Sensor Chip) was used to capture the biotinylated STING protein. Test compound injections were made at a flow rate of 100 μl per minute with a 60 second association time and variable dissociation time. A three-fold dilution series from a 10 μM starting concentration was used for all test compounds. Data analysis was performed using the BiacoreT200 data evaluation software package (GE Healthcare). Compound injections were referenced to both a blank surface and a buffer blank. Processed data were fit to an equilibrium or kinetic model to obtain the observed dissociation constant $K_D$. SPR binding data is provided in Table 1.

TABLE 1

| Scintillation Proximity Assay (SPA) Competitive Binding | | |
|---|---|---|
| SPR binding | H232R STING $K_D$ Mean (μM) (N) | WT STING $K_D$ Mean (μM) (N) |
| Example 1 Peak 1 | 4.1 (2) | 4.7 (2) |
| Example 1 Peak 2 | 3.25 (2) | 2.75 (2) |
| Example 1 Peak 3 | 1.5 (3) | 0.48 (3) |
| Example 1 Peak 4 | 0.58 (3) | 0.24 (3) |
| Example 2 Peak 1 | 0.116 (1) | 0.023 (1) |
| Example 2 Peak 2 | 0.091 (1) | 0.093 (1) |
| Example 2 Peak 3 | .006 (1) | .00044 (1) |
| Example 2 Peak 4 | 0.011 (1) | 0.00078 (1) |
| Example 3 Peak 1 | 0.032 (1) | 0.008 (1) |
| Example 3 Peak 2 | 0.039 (1) | 0.014 (1) |
| Example 3 Peak 3 | 0.003 (1) | 0.001 (1) |
| Example 3 Peak 4 | 0.001 (1) | 0.0003 (1) |
| Example 7 Peak 1 | 1.04 (1) | 0.098 (1) |
| Example 7 Peak 2 | 1.89 (1) | 0.416 (1) |
| Example 7 Peak 3 | 0.009 (1) | 0.004 (1) |
| Example 7 Peak 4 | 0.003 (1) | 0.003 (1) |
| Example 13 Peak 1 | 1.21 (2) | 1.29 (3) |
| Example 13 Peak 2 | 4.57 (2) | 5.98 (3) |
| Example 14 | 0.216 (2) | 0.015 (2) |

TABLE 1-continued

Scintillation Proximity Assay (SPA) Competitive Binding

| SPR binding | H232R STING $K_D$ Mean (µM) (N) | WT STING $K_D$ Mean (µM) (N) |
|---|---|---|
| Example 15 Peak 1 | 0.102 (2) | 0.045 (2) |
| Example 15 Peak 2 | 0.006 (2) | 0.003 (2) |
| Example 16 Peak 1 | 0.003 (2) | 0.057 (2) |
| Example 16 Peak 2 | 0.132 (2) | 0.020 (2) |
| Example 17 Peak 1 | 0.004 (1) | 0.0015 (2) |
| Example 17 Peak 2 | 0.0005 (2) | 0.0003 (2) |
| Example 18 | 0.001 (1) | 0.0002 (1) |
| Example 19 Peak 1 | 0.102 (1) | 0.086 (1) |
| Example 19 Peak 2 | 0.750 (1) | 0.740 (1) |
| Example 19 Peak 3 | 0.002 (1) | 0.003 (1) |
| Example 19 Peak 4 | 0.010 (1) | 0.019 (1) |
| Example 20 Peak 1 | 0.447 (1) | 0.256 (1) |
| Example 20 Peak 2 | 0.029 (2) | 0.046 (2) |
| Example 21 Peak 1 | 0.198 (1) | 0.127 (1) |
| Example 21 Peak 2 | 0.048 (1) | 0.016 (1) |
| Example 22 | 0.117 (1) | 0.449 (1) |
| Example 23 | 5.05 (1) | 0.993 (1) |

A radioligand binding assay was developed to determine compound interactions were competitive with a tritium-labeled version of the native STING ligand, $^3$H-cyclic guanine (2',5') monophosphate adenine (3',5') monophosphate ($^3$H-cGAMP). The STING constructs (WT and H232R) were comprised of residues 155-341 with both N- and C-terminal truncations; the N-terminal transmembrane domains were removed (1-154), as well as the C-terminal tail (342-379). A highly specific N-terminal biotinylation was achieved enzymatically with the *E. coli* biotin ligase (BirA) and inclusion of the high-affinity biotinylation peptide AviTag™. 100 nM STING protein was immobilized on 20 µg streptavidin polyvinyl toluene (SA-PVT) beads in 150 mM NaCl, 25 mM Hepes (pH 7.5), 0.1 mM EDTA, 1 mM DTT, 0.005% (v/v) Tween-20, 1% (v/v) DMSO. 100 nM $^3$H-cGAMP and compounds were added and allowed to come to equilibrium at room temperature (20 min). Compounds were tested in three-fold dilution series from a 100 µM starting concentration and normalized to a positive control compound that completely blocked $^3$H-cGAMP binding and the negative control DMSO. The $K_I$ for competitive binding was determined from the $IC_{50}$ with the Cheng-Prusoff equation (Cheng & Prusoff, Biochemical Pharmacology, 22 (1973), pp. 3099-3108). The $K_D$ values for $^3$H-cGAMP used in the Cheng-Prusoff equation were determined empirically to be 1 nM for WT STING, and 750 nM for R232H STING. SPA competitive binding data is provided in Table 2.

TABLE 2

| SPA competitive binding | WT STING $K_I$ Mean (µM) (N) |
|---|---|
| Example 1 Peak 3 | 0.107 (8) |
| Example 1 Peak 4 | 0.042 (8) |
| Example 2 Peak 1 | 0.007 (5) |
| Example 2 Peak 2 | 0.073 (5) |
| Example 2 Peak 3 | 0.002 (9) |
| Example 2 Peak 4 | 0.0002 (9) |
| Example 3 Peak 1 | 0.004 (2) |
| Example 3 Peak 2 | 0.018 (2) |
| Example 3 Peak 3 | 0.001 (1) |
| Example 3 Peak 4 | 0.0002 (4) |
| Example 7 Peak 1 | 0.044 (1) |
| Example 7 Peak 2 | 0.107 (1) |

TABLE 2-continued

| SPA competitive binding | WT STING $K_I$ Mean (µM) (N) |
|---|---|
| Example 7 Peak 3 | 0.013 (1) |
| Example 7 Peak 4 | 0.003 (1) |
| Example 13 Peak 1 | >1 (2) |
| Example 13 Peak 2 ( | >1 (2) |
| Example 14 | 0.008 (3) |
| Example 15 Peak 1 | 0.037 (3) |
| Example 15 Peak 2 | 0.001 (3) |
| Example 16 Peak 1 | 0.001 (3) |
| Example 16 Peak 2 | 0.009 (3) |
| Example 17 Peak 1 | 0.002 (1) |
| Example 17 Peak 2 | 0.0003 (2) |
| Example 18 | 0.00019 (1) |
| Example 19 Peak 1 | 0.022 (1) |
| Example 19 Peak 2 | >1 (1) |
| Example 19 Peak 3 | 0.002 (1) |
| Example 19 Peak 4 | 0.054 (1) |
| Example 20 Peak 1 | 0.294 (1) |
| Example 20 Peak 2 | 0.038 (2) |
| Example 21 Peak 1 | 0.142 (2) |
| Example 21 Peak 2 | 0.008 (2) |
| Example 22 | 0.222 (2) |
| Example 23 ( | 1.26 (1) |

Interferon-β Induction: THP-1 ISG Reporter Cell Line

THP-1 Lucia™ ISG cells (InvivoGen) express the secreted luciferase "Lucia" reporter gene under the control of an IRF-inducible composite promotor comprised of five interferon response elements. THP-1 Lucia™ ISG cells were grown in RPMI media plus 2 mM L-glutamine, 10% fetal bovine serum, and 0.5% Pen-Strep. Hygromycin B and Zeocin were present to maintain stable transfection. $10^4$ cells were seeded in 96-well plates and incubated overnight 37° C., 5% $CO_2$. 50 µL of serial diluted compounds in media (final 0.5% DMSO) was and incubated for an additional 24 hours. After incubation, the plates were centrifuged at 2000 rpm for 10 min. 50 µl of cell culture supernatant of each well was transferred to a white, opaque 96-well plate. One pouch of QUANTI-Luc™ (InvivoGen) powder was prepared in 25 mL of endotoxin-free water and 100 µL of prepared warm QUANTI-Luc solution were added to each well containing the supernatant. The luminescence signal was measured using a Perkin-Elmer Envision microplate reader. Data were normalized to "% effect" with a positive control STING agonist that was known to maximize the luciferase signal and the negative control DMSO. Interferon-13 induction data is provided in Table 3.

TABLE 3

| IFN-β THP-1 reporter | IFN-β induction EC50 Mean µM (N) |
|---|---|
| Example 1 Peak 3 | 10.12 (6) |
| Example 1 Peak 4 | 8.49 (6) |
| Example 2 Peak 1 ( | 3..08 (4) |
| Example 2 Peak 2 | 7.9 (4) |
| Example 2 Peak 3 | 0.93 (9) |
| Example 2 Peak 4 | 3.02 (7) |
| Example 3 Peak 1 | 6.52 (3) |
| Example 3 Peak 2 | 22.9 (3) |
| Example 3 Peak 3 | 2.1 (2) |
| Example 3 Peak 4 | 4.5 (3) |
| Example 7 Peak 1 | 13.8 (1) |
| Example 7 Peak 2 | >30 (1) |
| Example 7 Peak 3 | 4.6 (2) |
| Example 7 Peak 4 | 7.4 (2) |
| Example 13 Peak 1 | >100 (2) |
| Example 13 Peak 2 | >100 (2) |

TABLE 3-continued

| IFN-β THP-1 reporter | IFN-β induction EC50 Mean μM (N) |
|---|---|
| Example 14 | 31.17 (4) |
| Example 15 Peak 1 | 9.89 (4) |
| Example 15 Peak 2 | 5.19 (4) |
| Example 16 Peak 1 | 31.41 (3) |
| Example 16 Peak 2 | 14.88 (4) |

C. and 5% $CO_2$ for 24 hours. After incubation, the plates were centrifuged at 2000 rpm for 10 min. 50 μl of cell culture supernatant of each well was transferred to a white, opaque 96 well plate. QUANTI-Luc™ (InvivoGen) powder was prepared in 25 mL of endotoxin-free water and 100 uL of prepared warm QUANTI-Luc solution were added to each well containing culture supernatant and the luminescence signal was measured immediately using a Perkin Elmer Enspire microplate reader (0.2 sec). RLU was obtained by raw value. THP-1 cell reporter assay date is provided in Table 4.

TABLE 4

| Compound | THP-1 ISG WT EC50 (μM) | THP-1 ISG R232H EC50 (μM) | THP-1 ISG HAQ EC50 (μM) | THP-1 ISG AQ EC50 (μM) | THP-1 ISG R293Q EC50 (μM) |
|---|---|---|---|---|---|
| Example 1 Peak 3 | >50 (N = 2) | >50 (N = 3) | 32.56 (N = 2) | 15.38 (N = 2) | >50 (N = 2) |
| Example 1 Peak 4 | >50 (N = 2) | >50 (N = 3) | 25.47 (N = 2) | 23.93 (N = 2) | >50 (N = 2) |
| Example 2 Peak 2 | >50 (N = 2) | >50 (N = 3) | >50 (N = 1) | >50 (N = 1) | >50 (N = 1) |
| Example 2 Peak 3 | 7.58 (N = 3) | 12.67 (N = 3) | 16.56 (N = 3) | 6.52 (N = 3) | 7.16 (N = 3) |
| Example 2 Peak 4 | 5.79 (N = 4) | 12.92 (N = 4) | 12.58 (N = 4) | 5.33 (N = 4) | 7.57 (N = 4) |
| Example 2 Peak 1 | 5.83 (N = 2) | 3.26 (N = 2) | >50 (N = 1) | 7.32 (N = 2) | 6.63 (N = 2) |
| Example 14 | 27.62 (N = 3) | >50 (N = 3) | 27.13 (N = 3) | 26.10 (N = 3) | >50 (N = 2) |
| Example 16 Peak 1 | 23.63 (N = 3) | >50 (N = 3) | 29.32 (N = 3) | 30.69 (N = 3) | >50 (N = 2) |
| Example 16 Peak 2 | 16.37 (N = 3) | >50 (N = 3) | 16.84 (N = 3) | 12.96 (N = 3) | 27.14 (N = 3) |
| Example 15 Peak 2 | 6.48 (N = 3) | >50 (N = 3) | 9.75 (N = 3) | 6.51 (N = 3) | 14.40 (N = 3) |
| Example 15 Peak 1 | 25.77 (N = 2) | >50 (N = 3) | 18.37 (N = 3) | 12.58 (N = 3) | 24.66 (N = 3) |
| Example 17 Peak 1 | 9.97 (N = 3) | >50 (N = 3) | 12.80 (N = 3) | 6.80 (N = 3) | 19.39 (N = 3) |
| Example 17 Peak 2 | 2.22 (N = 3) | 7.34 (N = 3) | 4.86 (N = 3) | 2.67 (N = 3) | 4.17 (N = 3) |

TABLE 3-continued

| IFN-β THP-1 reporter | IFN-β induction EC50 Mean μM (N) |
|---|---|
| Example 17 Peak 1 | 10.43 (2) |
| Example 17 Peak 2 | 3.43 (4) |
| Example 18 | 0.98 (1) |
| Example 19 Peak 1 | 5.33 (2) |
| Example 19 Peak 2 | >100 (1) |
| Example 19 Peak 3 | 4.39 (1) |
| Example 19 Peak 4 | 8.82 (2) |
| Example 20 Peak 1 | 80.84 (2) |
| Example 20 Peak 2 | 7.54 (4) |
| Example 21 Peak 1 | >30 (1) |
| Example 21 Peak 2 | 28.5 (1) |
| Example 22 | >30 (1) |
| Example 23 | >100 (1) |

THP-1 Cell Reporter Assay with Different Human STING Polymorphisms to Measure Type I Interferon Activity The wild-type (WT) STING allele has been reported to have an additional 4 different single nucleotide polymorphisms (SNPs) in the human population that can affect its response. These SNPs are known as R71H-G230A-R293Q (HAQ), R232H, G230A-R293Q (AQ), and R293Q. In order to test whether indicated compounds can activate all five human STING alleles representing >98% of the human population, THP-1-Dual KO-STING cells (InvivoGen) were individually transduced with a lentivirus containing one of the human STING alleles (Genecopoeia). Transduced cells were selected and expression of STING was confirmed by western blot (data not shown). Selected cells were cultured and harvested in 50 mL conical tubes, counted using a BC Vi-flow and diluted to concentration of $7.4 \times 10^5$ cell/ml. 135 μl of diluted cells were transferred to a 96 well plate (100,000 cells/well) and incubated at 37° C. in a $CO_2$ incubator for 3 to 4 hours. Next, 15 uL of serially diluted test compound were added to each well for stimulation, the plate containing cells and compounds was further incubated at 37°

Phosphorylation of IRF3: THP-1 or OVCAR4 Cell ELISA

STING activation results in recruitment of TBK1 and phosphorylation of IRF3 transcription factor before induction of type I interferons. THP-1 cells (InvivoGen) or OVCAR4 cells (Pfizer Cell Bank) were grown in RPMI media plus 2 mM L-glutamine, 10% fetal bovine serum, and 0.5% Pen-Strep. $10^4$ cells were seeded in 96-well plates and incubated overnight 37° C., 5% CO2. Compounds serial diluted compounds in media (final 0.5% DMSO) were added to the cells and incubated for an additional 3 hours. After incubation, the plates were centrifuged at 2000 rpm for 5 min. The cells were then lysed in 100 μl RIPA buffer and vortexed for 30 minutes at room temperature. 25 μl of lysate was then transferred to clear polystyrene High Bind plates that had been previously coated with mouse anti-human IRF-3 capture antibody (BD Pharmigen), and allowed to incubate at 4° C. for 16 hours. The plates were then washed and incubated with rabbit anti-phospho-IRF3 detection antibody (Cell Signaling Technologies) for 1.5 hours at room temperature. Finally, an HRP-linked secondary antibody (Cell Signaling Technologies) was added for 30 min before the Glo Substrate Reagent (R&D Systems) was used generate the luminescent signal. The signal was measured using a Perkin-Elmer Envision microplate reader. Data were normalized to "% effect" with a positive control STING agonist that was known to maximize the phosphorylated IRF3 signal and the negative control was DMSO. IRF3 Phosphorylation data is provided in Tables 5 and 6.

TABLE 5

| pIRF3 ELISA THP-1 | pIRF EC50 Mean μM (N) |
|---|---|
| Example 1 Peak 3 | 25.6 (5) |
| Example 1 Peak 4 | 39.2 (5) |
| Example 2 Peak 1 | 58.4 (3) |
| Example 2 Peak 2 | >100 (3) |

TABLE 5-continued

| pIRF3 ELISA THP-1 | pIRF EC50 Mean μM (N) |
|---|---|
| Example 2 Peak 3 | 13.66 (10) |
| Example 2 Peak 4 | 23.68 (5) |
| Example 3 Peak 1 | >100 (2) |
| Example 3 Peak 2 | >100 (2) |
| Example 3 Peak 3 | 20.5 (2) |
| Example 3 Peak 4 | 30.69 (3) |
| Example 7 Peak 1 | ND |
| Example 7 Peak 2 | ND |
| Example 7 Peak 3 | ND |
| Example 7 Peak 4 | ND |
| Example 13 Peak 1 | >100 (2) |
| Example 13 Peak 2 | >100 (2) |
| Example 14 | >100 (3) |
| Example 15 Peak 1 | >100 (3) |
| Example 15 Peak 2 | 31.6 (3) |
| Example 16 Peak 1 | >100 (3) |
| Example 16 Peak 2 | >100 (3) |
| Example 17 Peak 1 | 92.8 (1) |
| Example 17 Peak 2 | 18.54 (3) |
| Example 18 | 9.04 (1) |
| Example 19 Peak 1 | 56.8 (1) |
| Example 19 Peak 2 | >100 (1) |
| Example 19 Peak 3 | 30.9 (1) |
| Example 19 Peak 4 | 66.0 (1) |
| Example 20 Peak 1 | >100 (1) |
| Example 20 Peak 2 | 62.55 (3) |
| Example 21 Peak 1 | ND |
| Example 21 Peak 2 | ND |
| Example 22 | ND |
| Example 23 | >100 (2) |

TABLE 6

| pIRF3 ELISA OVCAR4 | pIRF EC50 Mean μM (N) |
|---|---|
| Example 14 | 39.27 (3) |
| Example 15 Peak 1 | 51.5 (2) |
| Example 15 Peak 2 | 2.76 (3) |
| Example 16 Peak 1 | 57.0 (3) |
| Example 16 Peak 2 | 71.46 (3) |
| Example 17 Peak 1 | 46.37 (2) |
| Example 17 Peak 2 | 8.06 (3) |

We claim:

1. A method of treating breast cancer in a mammal, the method comprising administering to the mammal a therapeutically effective amount of the compound:

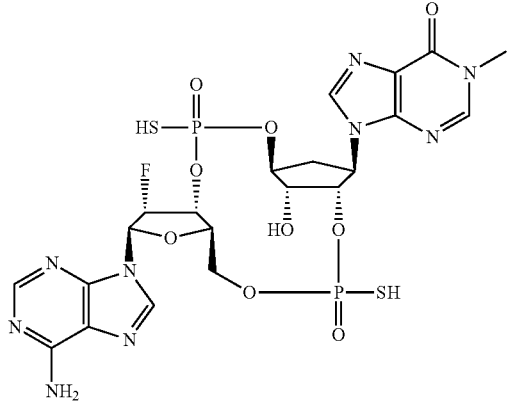 [SMILES: Cn1cnc2c(ncn2[C@@H]2C[C@@H]3OP(=O)(S)O[C@H]4[C@@H](F)[C@H](n5cnc6c(N)ncnc65)O[C@@H]4COP(=O)(S)O[C@@H]2[C@@H]3O)c1=O]

or a pharmaceutically acceptable salt thereof.

2. The method of claim 1, wherein said compound or salt is a component of an antibody-drug conjugate.

3. The method of claim 1, wherein said compound or salt is a component of a particle-based delivery system.

4. The method of claim 1, wherein the compound is

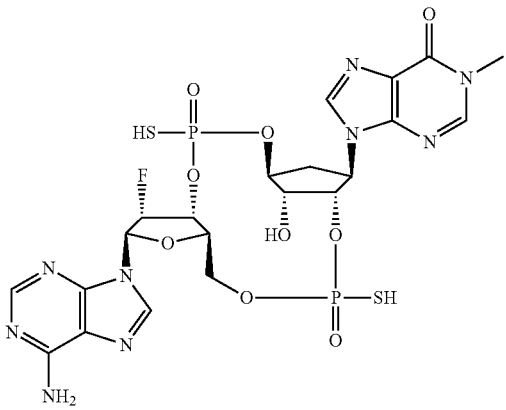

5. The method of claim 1, wherein the compound is a pharmaceutically acceptable salt of

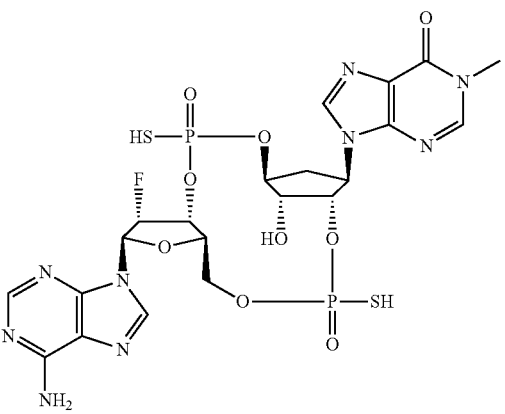 [SMILES: Cn1cnc2c(ncn2[C@@H]2C[C@@H]3OP(=O)(S)O[C@H]4[C@@H](F)[C@H](n5cnc6c(N)ncnc65)O[C@@H]4COP(=O)(S)O[C@@H]2[C@@H]3O)c1=O]

6. The method of claim 1, wherein the compound is a single diastereoisomer of the compound

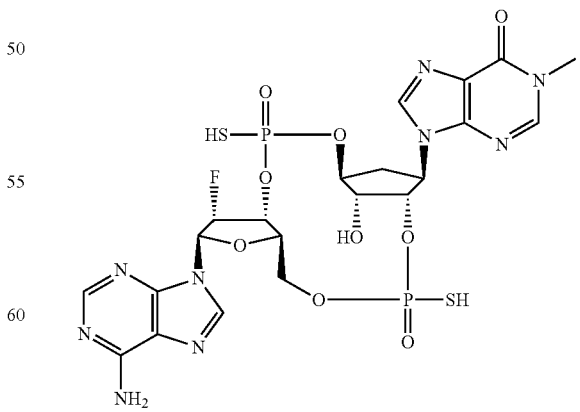

or a pharmaceutically acceptable salt thereof.

* * * * *